(12) United States Patent
Newberry

(10) Patent No.: US 11,737,690 B2
(45) Date of Patent: *Aug. 29, 2023

(54) SYSTEM AND METHOD FOR MONITORING NITRIC OXIDE LEVELS USING A NON-INVASIVE, MULTI-BAND BIOSENSOR

(71) Applicant: Trilinear BioVentures, LLC, Huntsville, AL (US)

(72) Inventor: Robert Steven Newberry, New Hope, AL (US)

(73) Assignee: TRILINEAR BIOVENTURES, LLC, Huntsville, AL (US)

( * ) Notice: Subject to any disclaimer, the term of this patent is extended or adjusted under 35 U.S.C. 154(b) by 674 days.

This patent is subject to a terminal disclaimer.

(21) Appl. No.: 16/711,038

(22) Filed: Dec. 11, 2019

(65) Prior Publication Data
US 2020/0129101 A1 Apr. 30, 2020

Related U.S. Application Data

(63) Continuation of application No. 15/718,721, filed on Sep. 28, 2017, now Pat. No. 10,517,515, which is a
(Continued)

(51) Int. Cl.
*A61B 5/1455* (2006.01)
*A61B 5/145* (2006.01)
(Continued)

(52) U.S. Cl.
CPC ........ *A61B 5/14546* (2013.01); *A61B 5/0004* (2013.01); *A61B 5/0022* (2013.01);
(Continued)

(58) Field of Classification Search
CPC .......................... A61B 5/1455; A61B 5/14532
See application file for complete search history.

(56) References Cited

U.S. PATENT DOCUMENTS

| 4,913,150 A | 4/1990 | Cheung et al. |
| 5,115,133 A | 5/1992 | Knudson |

(Continued)

FOREIGN PATENT DOCUMENTS

| CN | 102609627 A | 7/2012 |
| EP | 2017001250 A1 | 1/2017 |

(Continued)

OTHER PUBLICATIONS

EP Ser. No. 18758516.1. Extended Search Report (dated Nov. 12, 2020).

(Continued)

*Primary Examiner* — Marjan Fardanesh
(74) *Attorney, Agent, or Firm* — Polsinelli PC

(57) ABSTRACT

A device includes an optical circuit that obtains a first signal at a first wavelength using light reflected from skin tissue of a patient, wherein the first wavelength has a high absorption coefficient for nitric oxide (NO) in blood flow and a second PPG signal at a second wavelength using light reflected from skin tissue of the patient, wherein the second wavelength has a low absorption coefficient for NO in blood flow. A measurement of a level of NO in blood flow is determined using the first PPG signal and the second PPG signal. A health condition is determined using the measurement of the level of NO, such as hyperglycemia or hypoglycemia.

18 Claims, 32 Drawing Sheets

Related U.S. Application Data continuation of application No. 15/622,941, filed on Jun. 14, 2017, now Pat. No. 9,788,767, which is a continuation-in-part of application No. 15/490,813, filed on Apr. 18, 2017, now Pat. No. 9,980,676, and a continuation-in-part of application No. 15/489,391, filed on Apr. 17, 2017, now Pat. No. 9,974,451, and a continuation-in-part of application No. 15/485,816, filed on Apr. 12, 2017, now Pat. No. 10,155,087, and a continuation-in-part of application No. 15/462,700, filed on Mar. 17, 2017, now Pat. No. 10,500,354, said application No. 15/622,941 is a continuation-in-part of application No. 15/404,117, filed on Jan. 11, 2017, now Pat. No. 10,932,727, and a continuation-in-part of application No. 15/400,916, filed on Jan. 6, 2017, now Pat. No. 10,750,981, and a continuation-in-part of application No. 14/866,500, filed on Sep. 25, 2015, now Pat. No. 10,321,860.

(60) Provisional application No. 62/463,104, filed on Feb. 24, 2017, provisional application No. 62/457,138, filed on Feb. 9, 2017.

(51) Int. Cl.
*A61B 5/00* (2006.01)
*G16H 40/67* (2018.01)

(52) U.S. Cl.
CPC .......... *A61B 5/1455* (2013.01); *A61B 5/6817* (2013.01); *A61B 5/7235* (2013.01); *A61B 5/743* (2013.01); *G16H 40/67* (2018.01); *A61B 5/681* (2013.01); *A61B 5/6826* (2013.01); *A61B 2560/0223* (2013.01); *A61B 2560/0228* (2013.01); *Y02A 90/10* (2018.01)

(56) References Cited

U.S. PATENT DOCUMENTS

| | | | |
|---|---|---|---|
| 5,269,310 A | 12/1993 | Jones et al. |
| 5,358,703 A | 10/1994 | Ching |
| 5,515,847 A | 5/1996 | Braig et al. |
| 5,582,170 A | 12/1996 | Soller |
| 5,673,692 A | 10/1997 | Schulze et al. |
| 5,823,966 A | 10/1998 | Buchert |
| 5,885,842 A | 3/1999 | Lai |
| 5,947,911 A | 9/1999 | Wong et al. |
| 5,983,121 A | 11/1999 | Tsuchiya |
| 6,087,087 A | 7/2000 | Yonetani et al. |
| 6,280,390 B1 | 8/2001 | Akselrod et al. |
| 6,285,896 B1 | 9/2001 | Tobler et al. |
| 6,305,804 B1 | 10/2001 | Rice et al. |
| 6,537,225 B1 | 3/2003 | Mills |
| 6,694,180 B1 | 2/2004 | Boesen |
| 6,719,705 B2 | 4/2004 | Mills |
| 6,819,950 B2 | 11/2004 | Mills |
| 6,921,367 B2 | 7/2005 | Mills |
| 6,985,763 B2 | 1/2006 | Boas et al. |
| 7,154,592 B2 | 12/2006 | Reynolds et al. |
| 7,167,736 B2 | 1/2007 | Winther |
| 7,171,251 B2 | 1/2007 | Sarussi et al. |
| 7,179,228 B2 | 2/2007 | Banet |
| 7,209,775 B2 | 4/2007 | Bae et al. |
| 7,291,497 B2 | 11/2007 | Holmes et al. |
| 7,371,562 B2 | 5/2008 | Cunningham et al. |
| 7,608,045 B2 | 10/2009 | Mills |
| 7,647,083 B2 | 1/2010 | Al-Ali et al. |
| 7,761,127 B2 | 7/2010 | Al-Ali et al. |
| 7,763,472 B2 | 7/2010 | Doctor et al. |
| 7,764,982 B2 | 7/2010 | Dalke et al. |
| 7,941,199 B2 | 5/2011 | Kiani |
| 8,224,411 B2 | 7/2012 | Al-Ali et al. |
| 8,255,027 B2 | 8/2012 | Al-Ali et al. |
| 8,328,420 B2 | 12/2012 | Abreu |
| 8,385,996 B2 | 2/2013 | Smith et al. |
| 8,401,605 B2 | 3/2013 | Huiku |
| 8,483,787 B2 | 7/2013 | Al-Ali et al. |
| 8,494,507 B1 | 7/2013 | Tedesco et al. |
| 8,597,274 B2 | 12/2013 | Sloan et al. |
| 8,652,040 B2 | 2/2014 | Leboeuf et al. |
| 8,676,284 B2 | 3/2014 | He |
| 8,730,047 B2 | 5/2014 | Ridder et al. |
| 8,868,149 B2 | 10/2014 | Eisen et al. |
| 8,888,701 B2 | 11/2014 | Leboeuf et al. |
| 8,906,693 B2 | 12/2014 | Schultz et al. |
| 8,923,918 B2 | 12/2014 | Kreger et al. |
| 8,961,932 B2 | 2/2015 | Silverman |
| 9,022,973 B2 | 5/2015 | Sexton et al. |
| 9,131,882 B2 | 9/2015 | Al-Ali et al. |
| 9,149,216 B1 | 10/2015 | Eisen et al. |
| 9,149,646 B2 | 10/2015 | Keswarpu et al. |
| 9,387,033 B2 | 7/2016 | Yodfat et al. |
| 9,442,092 B2 | 9/2016 | Lane |
| 9,521,970 B2 | 12/2016 | Hoppe et al. |
| 9,554,738 B1 | 1/2017 | Gulati et al. |
| 9,562,913 B2 | 2/2017 | Stamler |
| 9,642,578 B2 | 5/2017 | Newberry |
| 9,668,701 B2 | 6/2017 | Maarek |
| 9,713,428 B2 | 7/2017 | Chon et al. |
| 9,739,663 B2 | 8/2017 | Halder et al. |
| 9,820,656 B2 | 11/2017 | Olivier |
| 9,839,381 B1 | 12/2017 | Weber et al. |
| 9,924,895 B2 | 3/2018 | Rawicz et al. |
| 9,949,675 B2 | 4/2018 | Miller |
| 9,999,355 B2 | 6/2018 | Kirenko |
| 10,028,682 B2 | 7/2018 | Thiele |
| D824,937 S | 8/2018 | Sparandara et al. |
| 10,099,554 B2 | 10/2018 | Steeg et al. |
| 10,130,285 B1 | 11/2018 | Singamsetty et al. |
| 10,153,796 B2 | 12/2018 | Fung et al. |
| 10,181,021 B2 | 1/2019 | Venkatraman et al. |
| 10,206,619 B1 | 2/2019 | Lee et al. |
| 10,215,698 B2 | 2/2019 | Han et al. |
| 10,227,063 B2 | 3/2019 | Abreu |
| 10,232,156 B2 | 3/2019 | Netzel et al. |
| 10,278,591 B2 | 5/2019 | Gil |
| D850,316 S | 6/2019 | Ennis et al. |
| 10,314,500 B2 | 6/2019 | Olivier |
| 10,322,728 B1 | 6/2019 | Porikli et al. |
| 10,342,495 B2 | 7/2019 | Melkoniemi et al. |
| 10,349,847 B2 | 7/2019 | Kwon et al. |
| 10,420,470 B2 | 9/2019 | Kwon et al. |
| 10,420,491 B2 | 9/2019 | Rajan et al. |
| 10,433,726 B2 | 10/2019 | Ramesh et al. |
| 10,433,738 B2 | 10/2019 | Thomas et al. |
| 10,433,739 B2 | 10/2019 | Weekly et al. |
| 10,463,283 B2 | 11/2019 | Ferber et al. |
| 2002/0049389 A1 | 4/2002 | Abreu |
| 2003/0229276 A1 | 12/2003 | Sarussi et al. |
| 2004/0078219 A1 | 4/2004 | Kaylor et al. |
| 2004/0100376 A1 | 5/2004 | Lye et al. |
| 2004/0157341 A1 | 8/2004 | Reynolds et al. |
| 2005/0101841 A9 | 5/2005 | Kaylor et al. |
| 2005/0209516 A1 | 9/2005 | Fraden |
| 2005/0228244 A1 | 10/2005 | Banet |
| 2005/0228299 A1 | 10/2005 | Banet |
| 2005/0245831 A1 | 11/2005 | Banet |
| 2006/0009698 A1 | 1/2006 | Banet |
| 2006/0094942 A1 | 5/2006 | Winther |
| 2006/0287589 A1 | 12/2006 | Wobermin et al. |
| 2007/0202605 A1 | 8/2007 | Doctor et al. |
| 2007/0203405 A1 | 8/2007 | Shimomura |
| 2007/0260132 A1 | 11/2007 | Sterling |
| 2008/0146890 A1 | 6/2008 | Leboeuf et al. |
| 2008/0165017 A1 | 7/2008 | Schwartz |
| 2008/0208019 A1 | 8/2008 | Nitzan |
| 2008/0241199 A1 | 10/2008 | Silverman |
| 2009/0043178 A1 | 2/2009 | Belotserkovsky |
| 2009/0156988 A1 | 6/2009 | Ferren et al. |
| 2009/0187167 A1 | 7/2009 | Sexton et al. |
| 2009/0287120 A1 | 11/2009 | Ferren et al. |
| 2010/0049020 A1 | 2/2010 | Dalke et al. |

(56) References Cited

U.S. PATENT DOCUMENTS

| | | |
|---|---|---|
| 2010/0191080 A1 | 7/2010 | Mills |
| 2010/0274101 A1 | 10/2010 | Lin et al. |
| 2010/0331631 A1 | 12/2010 | Maclaughlin |
| 2011/0082355 A1 | 4/2011 | Eisen et al. |
| 2011/0106050 A1 | 5/2011 | Yodfat et al. |
| 2011/0137141 A1 | 6/2011 | Razoumov et al. |
| 2011/0160697 A1 | 6/2011 | Yodfat et al. |
| 2011/0166553 A1 | 7/2011 | Holmes et al. |
| 2011/0224518 A1 | 9/2011 | Tindi |
| 2011/0237464 A1 | 9/2011 | Cunningham et al. |
| 2011/0275978 A1 | 11/2011 | Hyde |
| 2012/0010683 A1 | 1/2012 | Keswarpu et al. |
| 2012/0029363 A1 | 2/2012 | Lund |
| 2012/0095302 A1 | 4/2012 | Adhikari |
| 2012/0131507 A1 | 5/2012 | Sparandara et al. |
| 2012/0136054 A1 | 5/2012 | Schultz et al. |
| 2012/0156933 A1 | 6/2012 | Kreger et al. |
| 2012/0203077 A1 | 8/2012 | He et al. |
| 2012/0238844 A1 | 9/2012 | Grata et al. |
| 2012/0330126 A1 | 12/2012 | Hoppe et al. |
| 2013/0030259 A1 | 1/2013 | Thomsen et al. |
| 2013/0060098 A1 | 3/2013 | Thomsen et al. |
| 2013/0066176 A1 | 3/2013 | Addison et al. |
| 2013/0110311 A1 | 5/2013 | Ver Steeg et al. |
| 2013/0310669 A1 | 11/2013 | Nitzan |
| 2014/0046160 A1 | 2/2014 | Terashima et al. |
| 2014/0100432 A1 | 4/2014 | Golda et al. |
| 2014/0112940 A1 | 4/2014 | Lane |
| 2014/0194342 A1 | 7/2014 | Zhang et al. |
| 2014/0243648 A1 | 8/2014 | Dubielczyk |
| 2014/0253709 A1 | 9/2014 | Bresch et al. |
| 2014/0275852 A1 | 9/2014 | Hong et al. |
| 2014/0297313 A1 | 10/2014 | Condurso et al. |
| 2014/0316226 A1 | 10/2014 | Ferber et al. |
| 2015/0066238 A1 | 3/2015 | Todd et al. |
| 2015/0088007 A1 | 3/2015 | Bardy et al. |
| 2015/0094914 A1 | 4/2015 | Abreu |
| 2015/0105633 A1* | 4/2015 | LeBoeuf ............ A61B 5/6803 600/301 |
| 2015/0105638 A1 | 4/2015 | Eisen et al. |
| 2015/0109617 A1 | 4/2015 | Gilbert et al. |
| 2015/0148622 A1 | 5/2015 | Moyer et al. |
| 2015/0148635 A1 | 5/2015 | Benaron |
| 2015/0150453 A1 | 6/2015 | Abreu |
| 2015/0182172 A1 | 7/2015 | Shelley et al. |
| 2015/0229341 A1 | 8/2015 | Fung et al. |
| 2015/0250404 A1 | 9/2015 | Maarek |
| 2015/0282747 A1 | 10/2015 | Thiele |
| 2015/0366471 A1 | 12/2015 | Leboeuf et al. |
| 2016/0018257 A1 | 1/2016 | Mirov et al. |
| 2016/0058308 A1 | 3/2016 | Robinson |
| 2016/0058347 A1 | 3/2016 | Reichgott et al. |
| 2016/0066863 A1 | 3/2016 | Thaveeprungsrporn et al. |
| 2016/0100781 A1 | 4/2016 | Bechtel et al. |
| 2016/0262707 A1 | 9/2016 | Devries |
| 2016/0345912 A1 | 12/2016 | Maarek |
| 2016/0367154 A1 | 12/2016 | Gladshtein et al. |
| 2017/0014035 A1 | 1/2017 | Newberry |
| 2017/0027521 A1 | 2/2017 | Geva et al. |
| 2017/0050518 A1 | 2/2017 | Steeg et al. |
| 2017/0071550 A1 | 3/2017 | Newberry |
| 2017/0091436 A1 | 3/2017 | Cao et al. |
| 2017/0172477 A1 | 6/2017 | Adusumilli et al. |
| 2017/0215811 A1 | 8/2017 | Newberry |
| 2017/0256110 A1 | 9/2017 | Divincent et al. |
| 2017/0347894 A1 | 12/2017 | Bhushan et al. |
| 2017/0347899 A1 | 12/2017 | Bhushan et al. |
| 2018/0117291 A1 | 5/2018 | Netzel et al. |
| 2018/0140210 A1 | 5/2018 | Jelfs et al. |
| 2018/0140237 A1 | 5/2018 | Rajan et al. |
| 2018/0177416 A1 | 6/2018 | Church et al. |
| 2018/0177440 A1 | 6/2018 | Jelfs et al. |
| 2018/0200433 A1 | 7/2018 | Cirit |
| 2018/0264242 A1 | 9/2018 | Hoffman et al. |
| 2018/0353137 A1 | 12/2018 | Balajadia et al. |
| 2018/0358119 A1 | 12/2018 | Bhushan et al. |
| 2019/0046039 A1 | 2/2019 | Ramesh et al. |
| 2019/0050622 A1 | 2/2019 | Cabibihan et al. |
| 2019/0086331 A1 | 3/2019 | Han |
| 2019/0099114 A1 | 4/2019 | Radian et al. |
| 2019/0110745 A1 | 4/2019 | Linnes et al. |
| 2019/0125963 A1 | 5/2019 | Mou et al. |
| 2019/0125964 A1 | 5/2019 | Mou et al. |
| 2019/0133471 A1 | 5/2019 | Olson et al. |
| 2019/0192085 A1 | 6/2019 | Krishna et al. |
| 2019/0192086 A1 | 6/2019 | Krishna et al. |
| 2019/0251238 A1 | 8/2019 | Venkatraman et al. |
| 2019/0358387 A1 | 11/2019 | Elbadry et al. |

FOREIGN PATENT DOCUMENTS

| | | |
|---|---|---|
| EP | 3488776 A1 | 5/2019 |
| WO | 2004047630 A1 | 6/2004 |
| WO | 2007013054 A1 | 2/2007 |
| WO | 2008006150 A1 | 1/2008 |
| WO | 2010128852 A3 | 11/2010 |
| WO | 2010147968 A1 | 12/2010 |
| WO | 2012108895 A1 | 8/2012 |
| WO | 2013052318 A1 | 4/2013 |
| WO | 2013127564 A1 | 9/2013 |
| WO | 2014163583 A1 | 10/2014 |
| WO | 2015143197 A1 | 9/2015 |
| WO | 2015200148 A1 | 12/2015 |
| WO | 2017001249 A1 | 1/2017 |
| WO | 2018025257 A1 | 2/2018 |
| WO | 2018206875 A1 | 11/2018 |
| WO | 2019030700 A1 | 2/2019 |
| WO | 2019118053 A1 | 6/2019 |

OTHER PUBLICATIONS

Ignarro et al. "Endothelium-derived relaxing factor produced and released from artery and vein is nitric oxide." Proc. Natl. Acad. Sci. USA vol. 84, pp. 9265,9269 (Dec. 1987).

Noack et al. "Spectrophotometric determination of nitric oxide using hemoglobin." Neuroprotocols: A Companion to Methods in Neurosciences, vol. 1, No. 2,. pp. 133-139 (Oct. 1992).

Alonso et al. "The nitric oxide-endothelin-1 connection." Heart Failure Review, 8, 107-115 (2003).

PCT/US2018/0019273. International Search Report & Written Opinion (dated May 15, 2018).

Titheradge, "Nitric oxide in septic shock." Biochimica et Biophysica acta 1411, pp. 437-455 (1998).

Ogurek et al. "Carbon monoxide poisoning, smoke inhalation, cyanide poisoning." Condell EMS System CE, pp. 1-102 (Mar. 2009).

Archer, "Measurement of nitric oxide in biological models." The FASEB Journal, vol. 7, pp. 349-360 (Feb. 1993).

Oosthuizen et al., "Nitric oxide as inflammatory mediator in post-traumatic stress disorder (PTSD): evidence from an animal model." Neuropsychiatr Dis Treat. (2), pp. 109-123 (Jun. 2005).

Prasad et al. "Common biochemical defects linkage between post-traumatic stress disorders, mild traumatic brain injury (TBI) and penetrating TBI." Brain Res. 1599, UC Irvine (Jan. 2015).

Sudarma et al. "Effect of dark chocolate on nitric oxide serum levels and blood pressure in prehypertension subjects." Acta Med Indones-Indones J Intern. Med. vol. 43:4 (Oct. 2011).

* cited by examiner

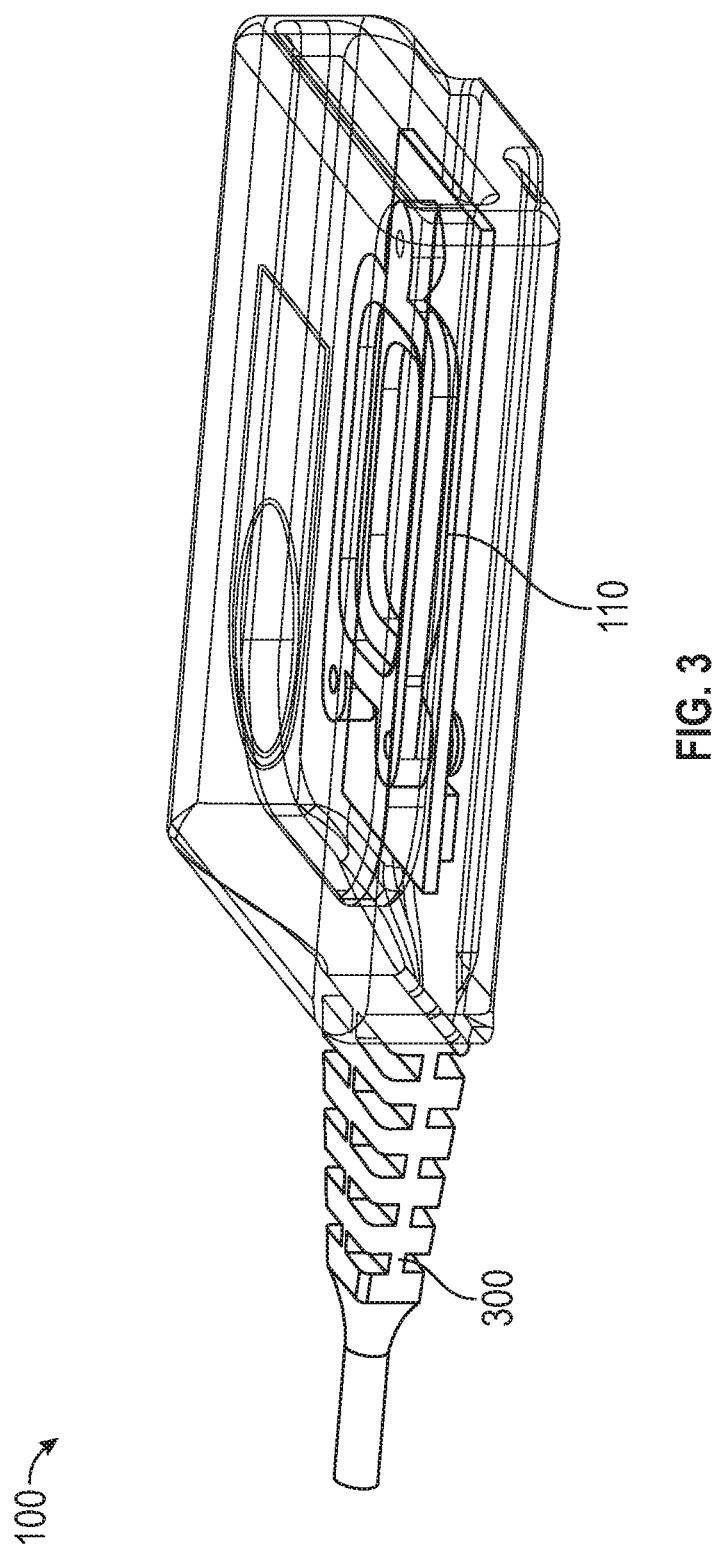

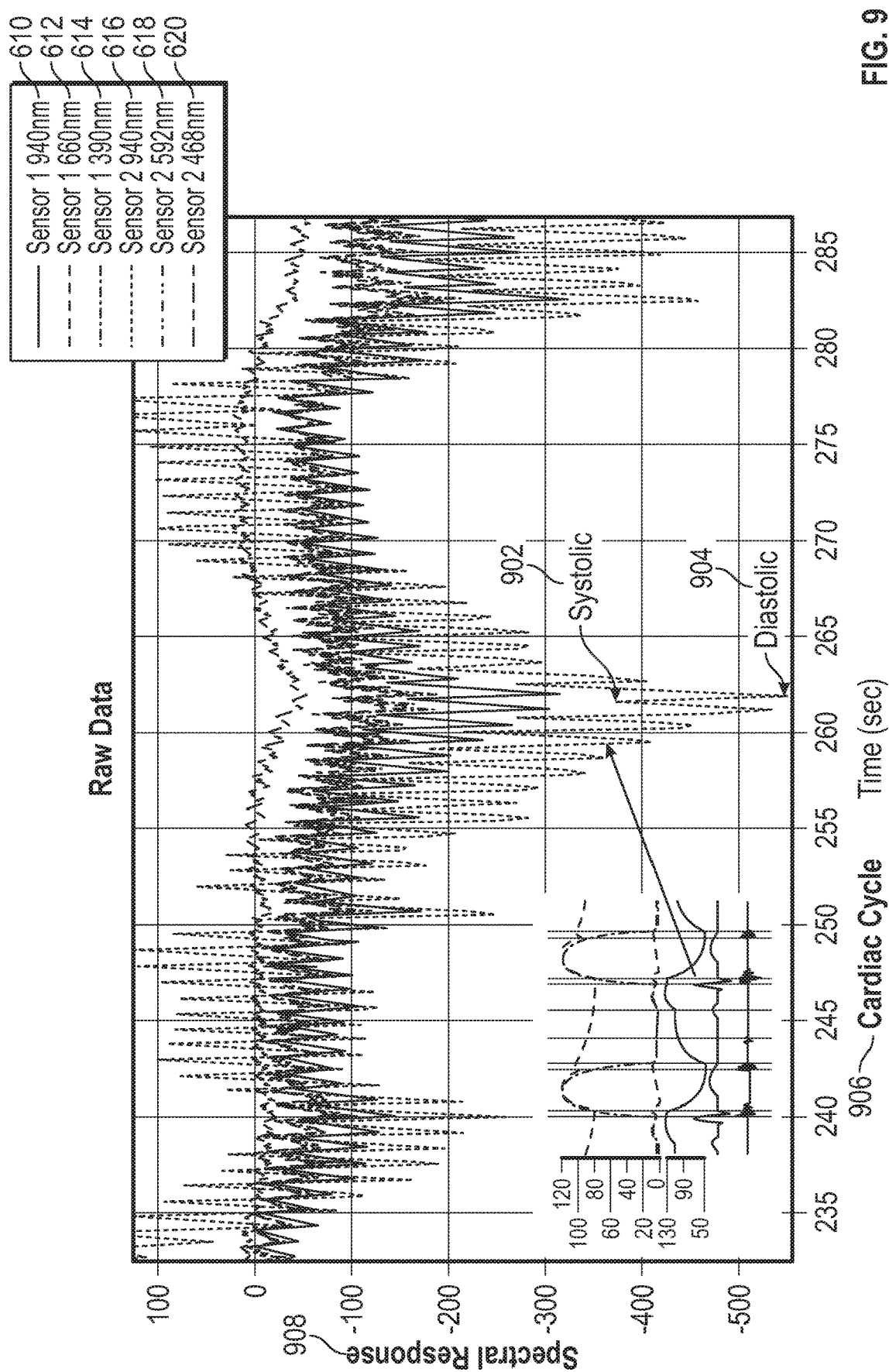

SYSTEM AND METHOD FOR MONITORING NITRIC OXIDE LEVELS USING A NON-INVASIVE, MULTI-BAND BIOSENSOR

CROSS REFERENCE TO RELATED APPLICATIONS

The present application claims priority under 35 U.S.C. § 120 as a continuation to U.S. patent application Ser. No. 15/718,721 entitled "SYSTEM AND METHOD FOR MONITORING NITRIC OXIDE LEVELS USING A NON-INVASIVE, MULTI-BAND BIOSENSOR," filed Sep. 28, 2017 and U.S. patent application Ser. No. 15/622,941 entitled, "SYSTEM AND METHOD FOR MONITORING NITRIC OXIDE LEVELS USING A NON-INVASIVE, MULTI-BAND BIOSENSOR," filed Jun. 14, 2017, which are hereby expressly incorporated by reference herein, which claims priority under 35 U.S.C. § 119 to U.S. Provisional Application No. 62/463,104 entitled, "SYSTEM AND METHOD FOR MONITORING NITRIC OXIDE LEVELS USING A NON-INVASIVE, MULTI-BAND BIOSENSOR," filed Feb. 24, 2017, and hereby expressly incorporated by reference herein.

FIELD

This application relates to a system and methods of non-invasive, autonomous health monitoring, and in particular a health monitoring sensor that non-invasively monitors Nitric Oxide (NO) levels in blood vessels.

BACKGROUND

Various invasive methods have been developed for measurement of Nitric Oxide (NO) levels using one or more types of techniques to remove cells from various types of bodily fluids. The methods usually require drawing blood from a blood vessel using a needle and syringe. The blood sample is then transported to a lab for analysis to determine NO levels using physical or chemical measurements. For example, in one current method, a blood sample is inserted into a semi-permeable vessel including an NO reacting substance that traps NO diffusing thereinto. A simple physical or chemical detection method is then used to measure the levels of the NO.

These known in vitro measurements of NO levels have disadvantages. The process of obtaining blood samples is time consuming, inconvenient and painful to a patient. It may also disrupt sleep of the patient. The measurements of the NO levels are not continuous and may only be updated by taking another blood sample. The measurements must often then be manually recorded into the patient's electronic medical record.

One current non-invasive method is known for measuring oxygen saturation in blood vessels using pulse oximeters. Pulse oximeters detect oxygen saturation of hemoglobin by using, e.g., spectrophotometry to determine spectral absorbencies and determining concentration levels of oxygen based on Beer-Lambert law principles. In addition, pulse oximetry may use photoplethysmography (PPG) methods for the assessment of oxygen saturation in pulsatile arterial blood flow. The subject's skin at a 'measurement location' is illuminated with two distinct wavelengths of light and the relative absorbance at each of the wavelengths is determined. For example, a wavelength in the visible red spectrum (for example, at 660 nm) has an extinction coefficient of hemoglobin that exceeds the extinction coefficient of oxihemoglobin. At a wavelength in the near infrared spectrum (for example, at 940 nm), the extinction coefficient of oxihemoglobin exceeds the extinction coefficient of hemoglobin. The pulse oximeter filters the absorbance of the pulsatile fraction of the blood, i.e. that due to arterial blood (AC components), from the constant absorbance by nonpulsatile venous or capillary blood and other tissue pigments (DC components), to eliminate the effect of tissue absorbance to measure the oxygen saturation of arterial blood. Such PPG techniques are heretofore been limited to determining oxygen saturation.

As such, there is a need for a patient monitoring system and method that includes a continuous and non-invasive biosensor configured to monitor concentration levels of NO in blood flow in vivo.

SUMMARY

According to a first aspect, a device includes an optical circuit configured to obtain a first photoplethysmography (PPG) signal at a first wavelength using light reflected from skin tissue of a patient, wherein the first wavelength has a high absorption coefficient for nitric oxide (NO) in blood flow; and obtain a second PPG signal at a second wavelength using light reflected from skin tissue of the patient, wherein the second wavelength has a low absorption coefficient for NO in blood flow. The device also includes at least one processing circuit configured to determine a measurement using the first PPG signal and the second PPG signal and determine a risk of a health condition using the measurement, wherein the health condition includes hyperglycemia or hypoglycemia.

According to a second aspect, a device includes an optical circuit configured to obtain a first PPG signal at a first wavelength using light reflected from skin tissue of a patient, wherein the first wavelength has a high absorption coefficient for nitric oxide (NO) in blood flow and obtain a second PPG signal at a second wavelength using light reflected from skin tissue of the patient, wherein the second wavelength has a low absorption coefficient for NO in blood flow. The device also includes at least one processing circuit configured to determine a measurement of a level of NO in blood flow using the first PPG signal and the second PPG signal and determine a risk of a health condition using the measurement of the level of NO.

According to a third aspect, a device includes at least one processing circuit configured to process a first PPG signal at a first wavelength of light that is reflected from skin tissue of a patient, wherein the first wavelength has a high absorption coefficient for nitric oxide (NO) in blood flow and process a second PPG signal at a second wavelength of light reflected from skin tissue of the patient, wherein the second wavelength has a low absorption coefficient for NO in blood flow. The at least one processing circuit is further configured to determine a measurement of a level of NO in blood flow using the first spectral response and the second spectral response and determine a risk of a health condition using the measurement of the level of NO.

In one or more of the above aspects, the measurement determined using the first PPG signal and the second PPG signal includes an AC component of the first PPG signal.

In one or more of the above aspects, the measurement determined using the first PPG signal and the second PPG signal includes a ratio of an AC component of the first PPG signal and an AC component of the second PPG signal.

In one or more of the above aspects, the measurement determined using the first PPG signal and the second PPG signal includes a level of NO in the blood flow of the patient.

In one or more of the above aspects, the measurement determined using the first PPG signal and the second PPG signal includes a level of glucose in the blood flow of the patient.

In one or more of the above aspects, the optical circuit is configured on a patch, wrist band, finger attachment or ear piece.

In one or more of the above aspects, the optical circuit and the at least one processing circuit is configured on a patch, wrist band, finger attachment or ear piece.

In one or more of the above aspects, the at least one processing circuit is further configured to generate an alert in response to determination of the risk of the health condition.

In one or more of the above aspects, the processing circuit is configured to determine the risk of the health condition using the measurement of the level of NO by comparing the measurement of the level of NO to a predetermined normal range and determining the measurement of the level of NO is higher or lower than the predetermined normal range.

In one or more of the above aspects, the processing circuit is configured to generate an alert when the measurement of the level of NO is higher or lower than the predetermined normal range or generate a display of the measurement of the level of NO.

In one or more of the above aspects, the health condition includes one or more of: hyperglycemia, hypoglycemia, diabetic condition, insulin response, hypovolemia, vascular health, dementia, Alzheimer's disease, post-traumatic stress syndrome (PTSD), infection or sepsis. The health condition may include a presence of one or more compounds that lead to unsafe levels of NO in blood vessels, wherein the one or more compounds include one or more of: lidocaine, nitrates such as nitroglycerin, nitric oxide, nitrogen based fertilizers, dapsone, benzocaine, cyanide, or anesthesia.

In one or more of the above aspects, the first wavelength having a high absorption coefficient for NO in blood flow is in a range of approximately 380 nm to 400 nm.

In one or more of the above aspects, the device further comprises a transceiver configured to transmit data to a remote user device, wherein the data includes an alert in response to determination of the risk of the health condition.

BRIEF DESCRIPTION OF THE DRAWINGS

FIG. 3 illustrates a perspective view of another embodiment of a biosensor for detecting NO levels.

FIG. 9 illustrates a schematic diagram of a graph of actual clinical data obtained using PPG techniques at a plurality of wavelengths.

DETAILED DESCRIPTION

Figure 1A:
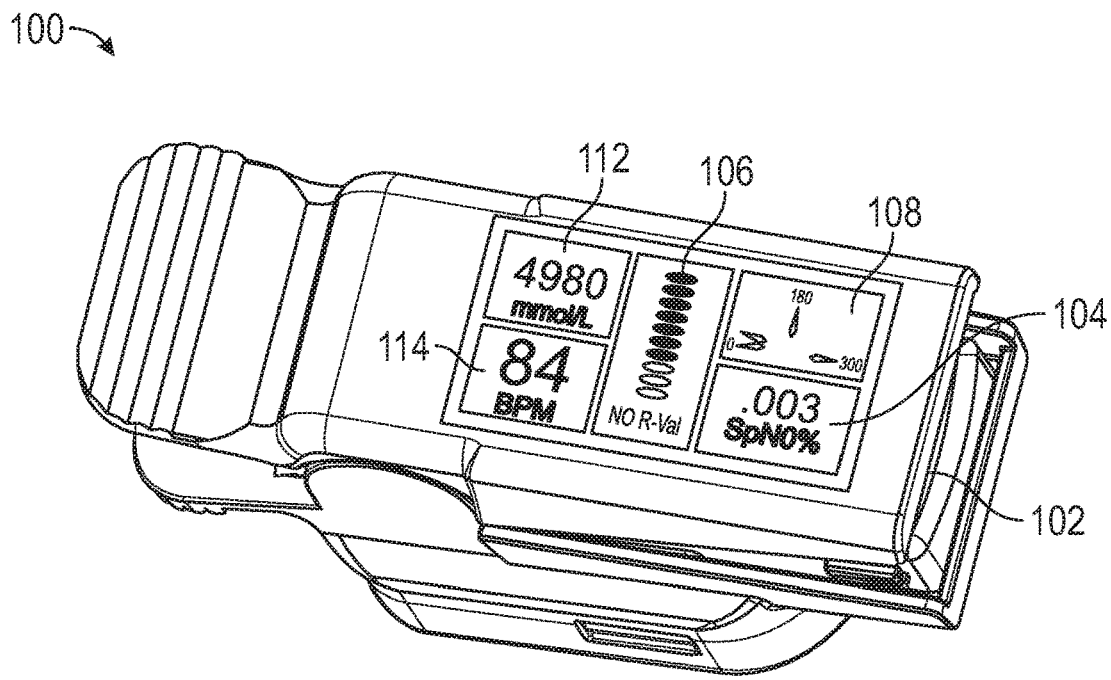
FIG. 1A and FIG. 1B illustrate a perspective view of an embodiment of a biosensor.

The word "exemplary" or "embodiment" is used herein to mean "serving as an example, instance, or illustration." Any implementation or aspect described herein as "exemplary" or as an "embodiment" is not necessarily to be construed as preferred or advantageous over other aspects of the disclosure. Likewise, the term "aspects" does not require that all aspects of the disclosure include the discussed feature, advantage, or mode of operation.

Embodiments will now be described in detail with reference to the accompanying drawings. In the following description, numerous specific details are set forth in order to provide a thorough understanding of the aspects described herein. It will be apparent, however, to one skilled in the art, that these and other aspects may be practiced without some or all of these specific details. In addition, well known steps in a method of a process may be omitted from flow diagrams presented herein in order not to obscure the aspects of the disclosure. Similarly, well known components in a device may be omitted from figures and descriptions thereof presented herein in order not to obscure the aspects of the disclosure.

Overview of Measurement of NO Levels

Embodiments described herein include a biosensor having an optical multi-band wavelength PPG sensor configured to determine NO levels in vitro in arterial blood, arteries, vessels and/or surrounding tissue. The non-invasive methods of embodiments of the biosensor may have a variety of uses, e.g., for monitoring of NO levels and diagnosis of various conditions related to NO levels. The biosensor may detect overproduction or underproduction of NO levels that have been associated with many different conditions. For example, NO production is related to endothelium-derived relaxing factor (EDRF). In addition, NO is a highly potent endogenous vasodilator. NO levels may also be used as indicator of inflammation, blood clotting, diabetes, dementia, Alzheimer's, post-traumatic stress syndrome (PTSD), and infections like sepsis.

Nitric oxide (NO) is produced by a group of enzymes called nitric oxide synthases. These enzymes convert arginine into citrulline, producing NO in the process. Oxygen and NADPH are necessary co-factors. There are three isoforms of nitric oxide synthase (NOS) named according to their activity or the tissue type in which they were first described. The isoforms of NOS are neural NOS (or nNOS, type 1), inducible NOS (or iNOS, type 2), and endothelial NOS (or eNOS, type 3). These enzymes are also sometimes referred to by number, so that nNOS is known as NOS1, iNOS is known as NOS2, and eNOS is known as NOS3. Despite the names of the enzymes, all three isoforms can be found in variety of tissues and cell types. Two of the enzymes (nNOS and eNOS) are constitutively expressed in mammalian cells and synthesize NO in response to increases in intracellular calcium levels. In some cases, however, they are able to increase NO production independently of calcium levels in response to stimuli such as shear stress.

In most cases NO production increases in proportion to the amount of calories or food consumed. Normally this is derived from the eNOS type NO production, and the body uses the NO first as a vasodilator and also as a protective oxidation layer to prevent undesired oxides from passing thru the cells in the blood vessels walls. The amount of NO released in this case is measured in small pulses and builds up as part of the normal digestion process. In the case of type 1 or type 2 diabetics, the normal levels of eNOS are abnormally low as found in recent clinical studies.

However iNOS activity is independent of the level of calcium in the cell, and all forms of the NOS isoforms are dependent on the binding of calmodulin. Increases in cellular calcium lead to increase in levels of calmodulin and the increased binding of calmodulin to eNOS and nNOS leads to a transient increase in NO production by these enzymes. By contrast iNOS is able to bind tightly to calmodulin even at extremely low concentrations of calcium. Therefore iNOS activity does not respond to changes in calcium levels in the cell. As a result of the production of NO by iNOS, it lasts much longer than other forms of isoforms of NOS and tends to produce much higher concentrations of NO in the body. This is likely the reason that iNOS levels are known to be elevated in dementia & Alzheimer's patents and have increased calcium deposits in their brain tissue.

Inducible iNOS levels are highly connected with sepsis infections which typically lead to large levels of NO in the blood stream, which in turns leads to organ failure. Lastly abnormal amounts of nNOS levels are typically associated with issues with blood pressure regulation, neurotransmission issues, and penal erection. Table 1 below summarizes the NOS isoforms.

TABLE 1

Nitric Oxide Synthesis (NOS isoforms)
Oosthuizen et al.
Table 2 NOS isoforms

| | Neural (n NOS, type 1) | Inducible (iNOS, type 2) | Endothelial (eNOS, type 3) |
|---|---|---|---|
| Cells first identified in | Neurons | Macrophages | Endothelium |
| Other cells expressing | Myocytes | Astrocytes | Neurons |
| | Astrocytes | Microglia | |
| Intracellular localization | Soluble or membrane bound | Soluble or membrane bound | Largely membrane bound |
| $Ca^{2+}$ dependency | Activity depends on elevated $Ca^{2+}$ | Activity is independent of elevated $Ca^{2+}$ | Activity depends on elevated $Ca^{2+}$ |
| Expression | Constitutive inducible under certain circumstances, eg, trauma | Inducible | Constitutive |

TABLE 1-continued

Nitric Oxide Synthesis (NOS isoforms)
Oosthuizen et al.
Table 2 NOS isoforms

|  | Neural (n NOS, type 1) | Inducible (iNOS, type 2) | Endothelial (eNOS, type 3) |
| --- | --- | --- | --- |
| Amounts of NO released | Small, pulses | Large, continuous | Small, pulses |
| Proposed function | Regulation | Host defense | Regulation |
| Activators | Glutamate Noradrenaline | Lipopoly-saccharide | Acetylcholine |

Data adapted from Yun et al (1997) and Moncada et al (1997).

Thus, the overproduction or underproduction of NO levels may be associated with many different health conditions. Embodiments of the biosensor described herein may continuously monitor NO levels non-invasively in vivo without need for blood samples. The NO levels of a patient may be continuously displayed and monitored. The NO levels may be used for diagnosis of one or more of these or other health conditions. Measuring NO or related compounds may provide early warning information about a patient's condition and allow for more immediate medical intervention. Since current measurement methods of NO do not allow health care professionals or even home care patients to measure NO continuously in blood vessels, the biosensor described herein may be potentially lifesaving for critical conditions. Very often trauma patients require frequent monitoring and invasive blood tests are the only method to sense worsening conditions prior to emergency conditions. The described non-invasive biosensor measures NO levels in blood vessels and provides efficiency to a host of current methods and treatment procedures in medical facilities around the globe. For example, the measurement of nitric oxide (NO) levels in blood vessels described herein provides a much earlier warning to care providers that intervention is needed for patient care.

Overview of Biosensor

In an embodiment, a biosensor includes a PPG circuit, a processing circuit, optional on-board display and a wireless or wired transceiver. The PPG circuit is configured to transmit light at a plurality of wavelengths directed at skin tissue of a patient. The PPG circuit is configured to detect light reflected from the skin tissue of the patient and generate spectral responses at a plurality of wavelengths. The processing circuit is configured to obtain a measurement of NO levels using the spectral responses at the plurality of wavelengths using one or more measurement techniques described herein. An indication of the NO level may then be displayed on a display of the biosensor. The biosensor may transmit the measurements of NO levels via a wireless or wired transceiver to a remote display.

Embodiments—Biosensor Form Factors

Figure 1B:
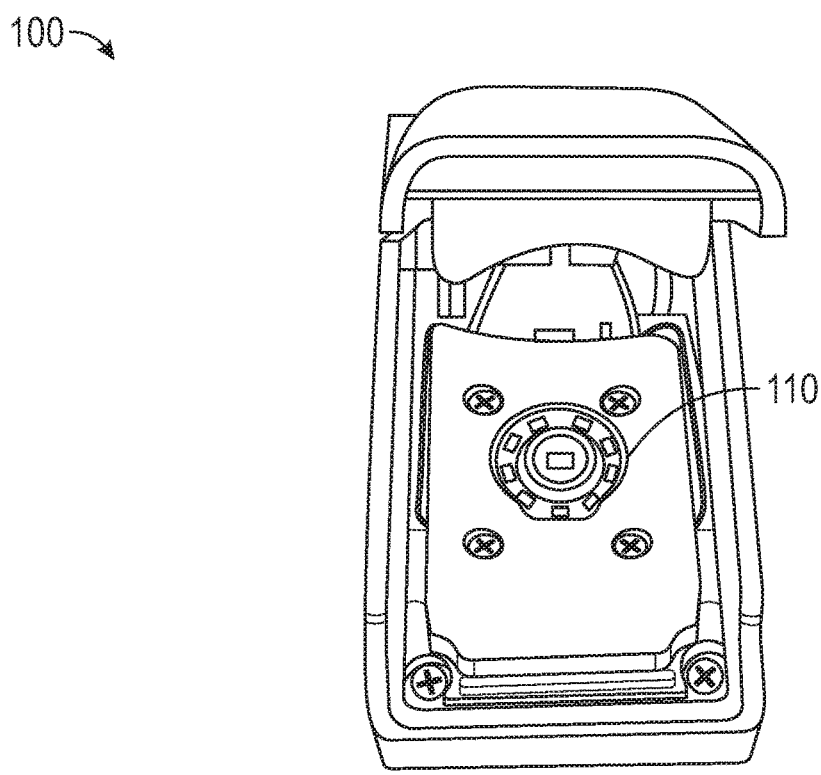

FIG. 1A and FIG. 1B illustrate a perspective view of an embodiment of a biosensor 100. In this embodiment, the biosensor 100 includes a finger attachment 102. The finger attachment 102 includes the PPG circuit 110 and is configured to securely hold a finger that is inserted into the finger attachment 102.

In use, a patient places a finger inside the finger attachment 102. The biosensor 100 is configured to monitor nitric oxide (NO) levels in the blood vessels of the patient. A PPG circuit 110 in the biosensor 100 is configured to transmit light at a plurality of wavelengths directed at skin tissue of the finger of the patient. The PPG circuit 110 is configured to detect light reflected from the skin tissue of the finger and generate spectral responses at a plurality of wavelengths. A processing circuit in the biosensor 100 is configured to obtain a measurement of NO levels from the spectral responses at the plurality of wavelengths using one or more measurement techniques described herein. The NO levels may be continuously monitored, e.g. the NO measurements may be obtained a plurality of times per minute and averaged over a predetermined time period. An indication of the NO levels may then be displayed on a display of the biosensor 100.

The biosensor 100 includes one or more types of displays of the measured nitric oxide (NO) levels. The displays may include, e.g., arterial nitric oxide saturation level 104 (such as SpNO). The display may include a bar meter 106 illustrating a relative measured nitric oxide level. The display may include a dial type display 108 that indicates a relative measured nitric oxide level. The biosensor 100 may display the measured nitric oxide level in mmol/liter units 112. These types of displays are examples only and other types of display may be employed to indicate the level of NO measured in a patient.

The biosensor 100 may also display other patient vitals such as heart rate, e.g. beats per minute (bpm) 114. The biosensor 100 may also include a power control.

The biosensor 100 may be implemented in other compact form factors, such as on a patch, wrist band or ear piece. Due to its compact form factor, the biosensor 100 may be configured for measurements on various skin surfaces of a patient, including on a forehead, arm, wrist, abdominal area, chest, leg, ear, ear lobe, finger, toe, ear canal, etc.

Figures 2A, 2B:
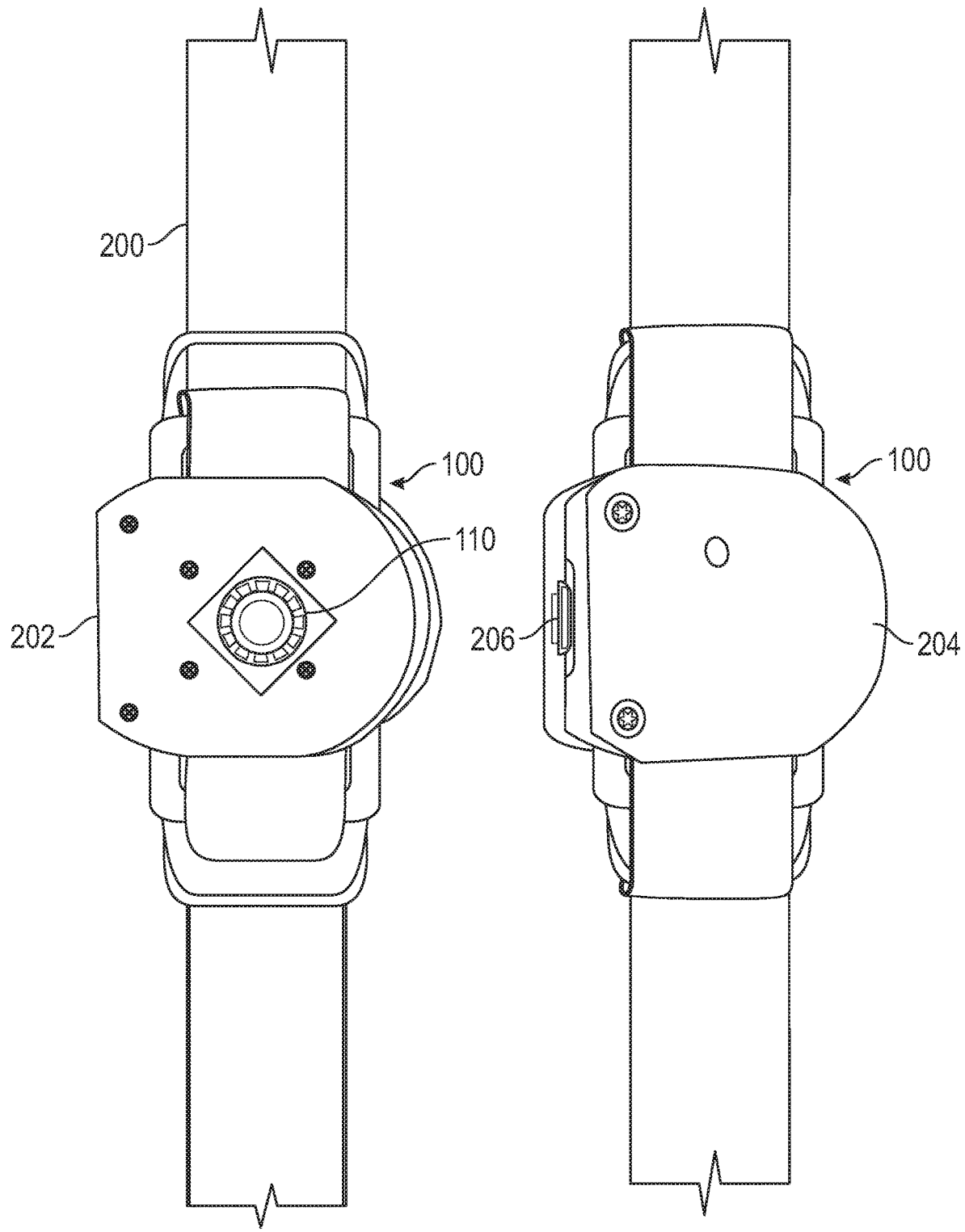
FIG. 2A and FIG. 2B illustrate a perspective view of another embodiment of a biosensor.

FIG. 2A and FIG. 2B illustrate a perspective view of another embodiment of a biosensor 100 for detecting NO levels. In this embodiment, the biosensor 100 is implemented with an adjustable band 200. The adjustable band 200 may be configured to fit around a wrist, arm, leg, ankle, etc. FIG. 2A illustrates a first side 202 of the biosensor 100 that includes at least one opening for the PPG circuit 110 to emit light directed to and detect light reflected from skin tissue of a user. FIG. 2B illustrates a second side 204 of the biosensor 100 that may include a display (not shown). A USB or other port 206 may be implemented to transmit data to and from the biosensor 100. The biosensor 100 may also include a wireless transceiver.

FIG. 3 illustrates a perspective view of another embodiment of a biosensor 100 for detecting NO levels. In this embodiment, the biosensor 100 includes a PPG circuit 110 and a wired connection 300 for communicating data with a remote device, such as a patient display or monitoring device. The biosensor 100 may be attached to different areas of tissue via an adhesive tape, adhesive backing or other means. For example, the biosensor 100 may be attached to a hand, arm, wrist, forehead, chest, abdominal area, ear, ear lobe, or other area of the skin or body or living tissue.

In another embodiment, the biosensor 100 is may be configured in an earpiece (not shown). The biosensor 100 is configured to transmit light into the ear canal from one or more optical fibers in an ear bud and detect light from the ear canal using one or more optical fibers.

In one study, a mechanical contact of glass with the subject's skin substantially increased the amplitude of the observed PPG signal. Moreover, by increasing the force of the contact, the amplitude of the PPG signal in the area is increased. As such, increased compression of the biosensor 100 against skin tissue may enhance intensity of the PPG signal. So compression of the biosensor 100 against the skin of a patient may be considered during use of biosensor 100 in its one or more form factors. The article by Kamshilin AA, Nippolainen E, Sidorov IS, et al. entitled "A new look at the essence of the imaging photoplethysmography" in Scientific Reports, May 21, 2015, 5:10494 and doi:10.1038/srep10494 includes further details on spatial distribution of PPG intensity amplitude for different forces of contact, and is hereby incorporated by reference herein.

Embodiment—Biosensor Components

Figure 4:
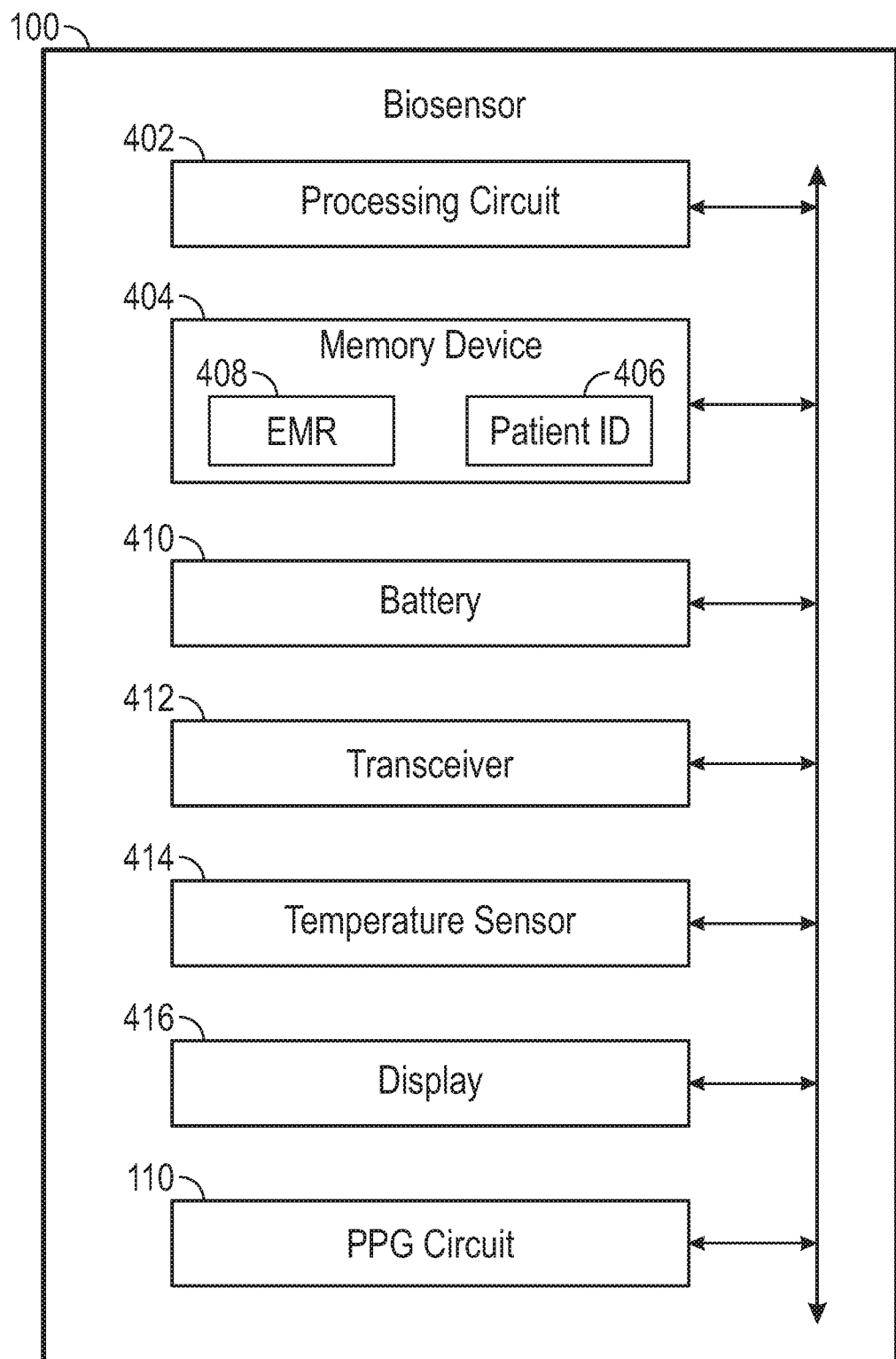
FIG. 4 illustrates a schematic block diagram of an exemplary embodiment of components of the biosensor.

FIG. 4 illustrates a schematic block diagram of an exemplary embodiment of components of the biosensor 100. The biosensor 100 includes the PPG circuit 110 as described in more detail herein. The PPG circuit 110 may be configured to detect oxygen saturation (SaO2 or SpO2) levels in blood flow, as well as heart rate and blood pressure. In addition, the PPG circuit 110 is configured to detect concentration levels or indicators of NO levels in the blood.

The biosensor 100 also includes one or more processing circuits 402 communicatively coupled to a memory device 404. In one aspect, the memory device 404 may include one or more non-transitory processor readable memories that store instructions which when executed by the one or more processing circuits 402, causes the one or more processing circuits 402 to perform one or more functions described herein. The memory device 404 may also include an EEPROM or other type of memory to store a patient identification (ID) 406 that is associated with a patient being monitored by the biosensor 100. The patient identification 406 may include a number, name, date of birth, password, etc. The memory device 404 may also store an electronic medical record (EMR) 408 or portion of the EMR 408 associated with the patient being monitored by the biosensor 100. The biosensor data obtained by the biosensor 100 may be stored in the EMR 408. The processing circuit 42 may be co-located with one or more of the other circuits in the biosensor 100 in a same physical encasement or located separately in a different physical encasement or located remotely. In an embodiment, the biosensor 100 is battery operated and includes a battery 420, such as a lithium ion battery.

The biosensor 100 further includes a transceiver 412. The transceiver 412 may include a wireless or wired transceiver configured to communicate with one or more devices over a LAN, MAN and/or WAN. In one aspect, the transceiver 412 may include a Bluetooth enabled (BLE) transceiver or IEEE 802.11ah, Zigbee, IEEE 802.15-11 or WLAN (such as an IEEE 802.11 standard protocol) compliant wireless transceiver. In another aspect, the transceiver 412 may operate using RFID, short range radio frequency, infrared link, or other short range wireless communication protocol. In another aspect, the transceiver 412 may also include or alternatively include an interface for communicating over a cellular radio access network, such as an Universal Mobile Telecommunications System (UMTS) Terrestrial Radio Access Network (UTRAN), Long Term Evolution (LTE) Evolved UTRAN (E-UTRAN), and/or LTE-Advanced (LTE-A) or other types of cellular networks. In an embodiment, the transceiver 412 may include a thin foil for an antenna that is specially cut and includes a carbon pad contact to a main printed circuit board (PCB) of the biosensor 100. This type of antenna is inexpensive to manufacture and may be printed on the inside of an enclosure for the biosensor 100 situated away from the skin of the patient to minimize absorption. The transceiver 412 may also include a wired transceiver including a port or interface, e.g., a USB port or other type of wired connection port, for communication with one or more other devices using Ethernet, IP, or other protocols over a LAN, MAN and/or WAN.

The biosensor 100 may also include a temperature sensor 414 configured to detect a temperature of a patient. For example, the temperature sensor 414 may include an array of sensors (e.g., 16×16 pixels) positioned on a side of the biosensor 100 with the PPG circuit 110 such that the array of sensors are adjacent to the skin of the patient. The array of sensors is configured to detect a temperature of the patient from the skin. The temperature sensor 414 may also be used to calibrate the PPG circuit 110.

The biosensor 100 may also include a display 416 for displaying biosensor data. Alternatively or in addition thereto, the transceiver 412 may communicate biosensor data, such as NO levels, to a remote device for display.

Embodiment-PPG Circuit

Figure 5:
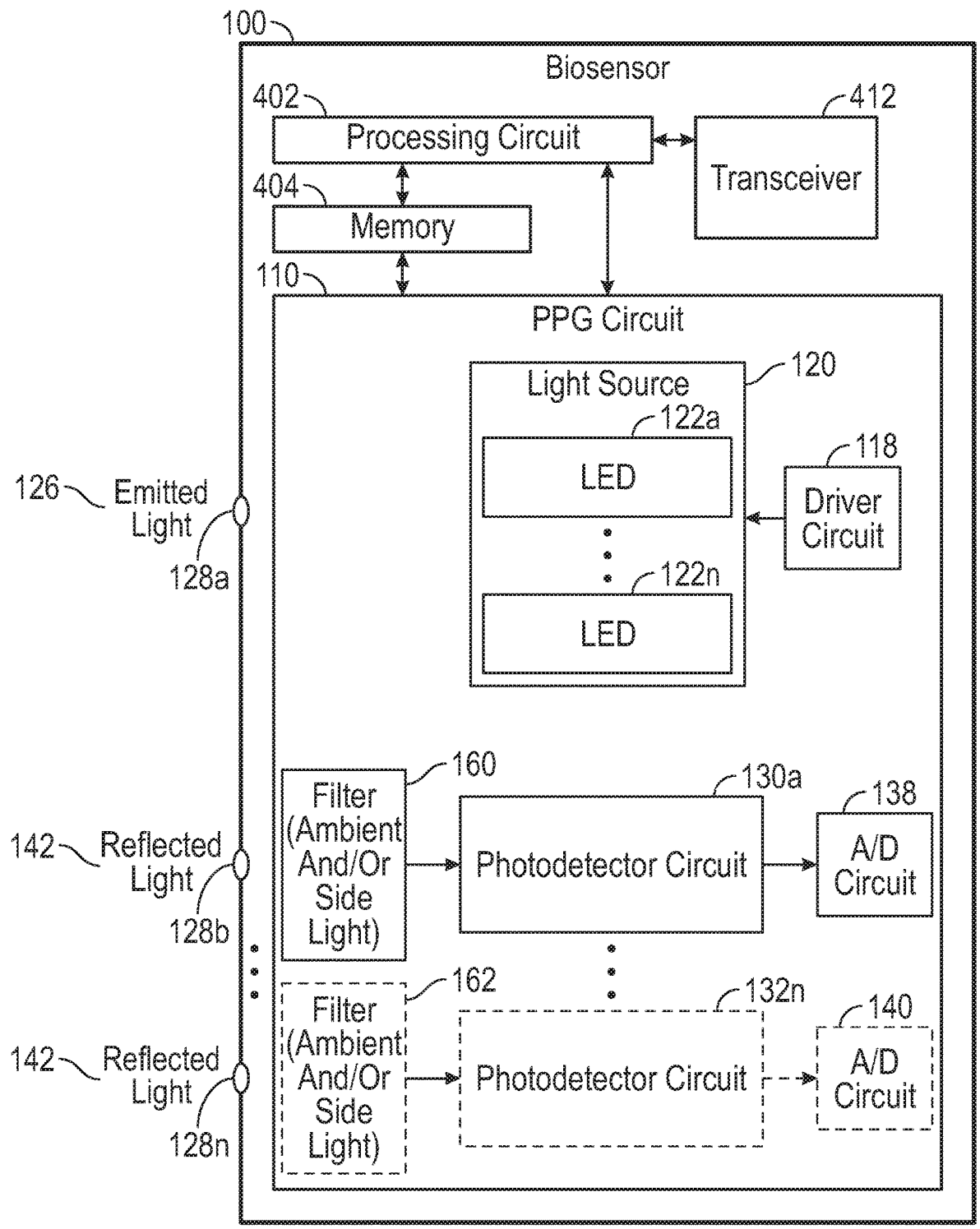
FIG. 5 illustrates a schematic block diagram illustrating an embodiment of the PPG circuit in more detail.

FIG. 5 illustrates a schematic block diagram illustrating an embodiment of the PPG circuit 110 in more detail. The PPG circuit 110 includes a light source 120 configured to emit a plurality of wavelengths of light across various spectrums. For example, the light source 120 mat include a plurality of LEDs 122a-n. The PPG circuit 110 is configured to direct the emitted light at an outer or epidermal layer of skin tissue of a patient through at least one aperture 128a. The plurality of LEDs 122 are configured to emit light in one or more spectrums, including infrared (IR) light, ultraviolet (UV) light, near IR light or visible light, in response to driver circuit 118. For example, the biosensor 100 may include a first LED 122a that emits visible light and a second LED 122b that emits infrared light and a third LED 122c that emits UV light, etc. In another embodiment, one or more of the light sources 122a-n may include tunable LEDs or lasers operable to emit light over one or more frequencies or ranges of frequencies or spectrums in response to driver circuit 118.

In an embodiment, the driver circuit 118 is configured to control the one or more LEDs 122a-n to generate light at one or more frequencies for predetermined periods of time. The driver circuit 118 may control the LEDs 122a-n to operate concurrently or consecutively. The driver circuit 118 is configured to control a power level, emission period and frequency of emission of the LEDs 122a-n. The biosensor 100 is thus configured to emit one or more wavelengths of light in one or more spectrums that is directed at the surface or epidermal layer of the skin tissue of a patient.

The PPG circuit 110 further includes one or more photodetector circuits 130a-n. For example, a first photodetector circuit 130 may be configured to detect visible light and the second photodetector circuit 130 may be configured to detect IR light. The first photodetector circuit 130 and the second photodetector circuit 130 may also include a first filter 160 and a second filter 162 configured to filter ambient light and/or scattered light. For example, in some embodiments, only light reflected at an approximately perpendicular angle to the skin surface of the patient is desired to pass through the filters. The first photodetector circuit 130 and the second photodetector circuit 132 are coupled to a first A/D circuit 138 and a second A/D circuit 140. Alternatively, a single A/D circuit may be coupled to each of the photodetector circuits 130a-n.

In another embodiment, a single photodetector circuit 130 may be implemented operable to detect light over multiple spectrums or frequency ranges. For example, the photodetector circuit 130 may include a Digital UV Index/IR/Visible Light Sensor such as Part No. Si1145 from Silicon Labs™.

The one or more photodetector circuits 130 include a spectrometer or other type of circuit configured to detect an intensity of light as a function of wavelength or frequency to obtain a spectral response. The one or more photodetector circuits 130 detect the intensity of light either transmitted through or reflected from tissue of a patient that enters one or more apertures 128b-n of the biosensor 100. For example, the light may be detected from transmissive absorption (e.g., through a fingertip or ear lobe) or from reflection (e.g., reflected from a forehead or stomach tissue). The one or more photodetector circuits 130a-n then obtain a spectral response of the reflected light by measuring the intensity of light at one or more wavelengths.

In another embodiment, the light source 120 may include a broad spectrum light source, such as a white light to infrared (IR) or near IR LED 122, that emits light with wavelengths from e.g. 350 nm to 2500 nm. Broad spectrum light sources with different ranges may be implemented. In an aspect, a broad spectrum light source is implemented with a range across 100 nm wavelengths to 2000 nm range of wavelengths in the visible, IR and/or UV frequencies. For example, a broadband tungsten light source for spectroscopy may be used. The spectral response of the reflected light is then measured across the wavelengths in the broad spectrum, e.g. from 350 nm to 2500 nm, concurrently. In an aspect, a charge coupled device (CCD) spectrometer may be configured in the photodetector circuit 130 to measure the spectral response of the detected light over the broad spectrum.

Figure 6:
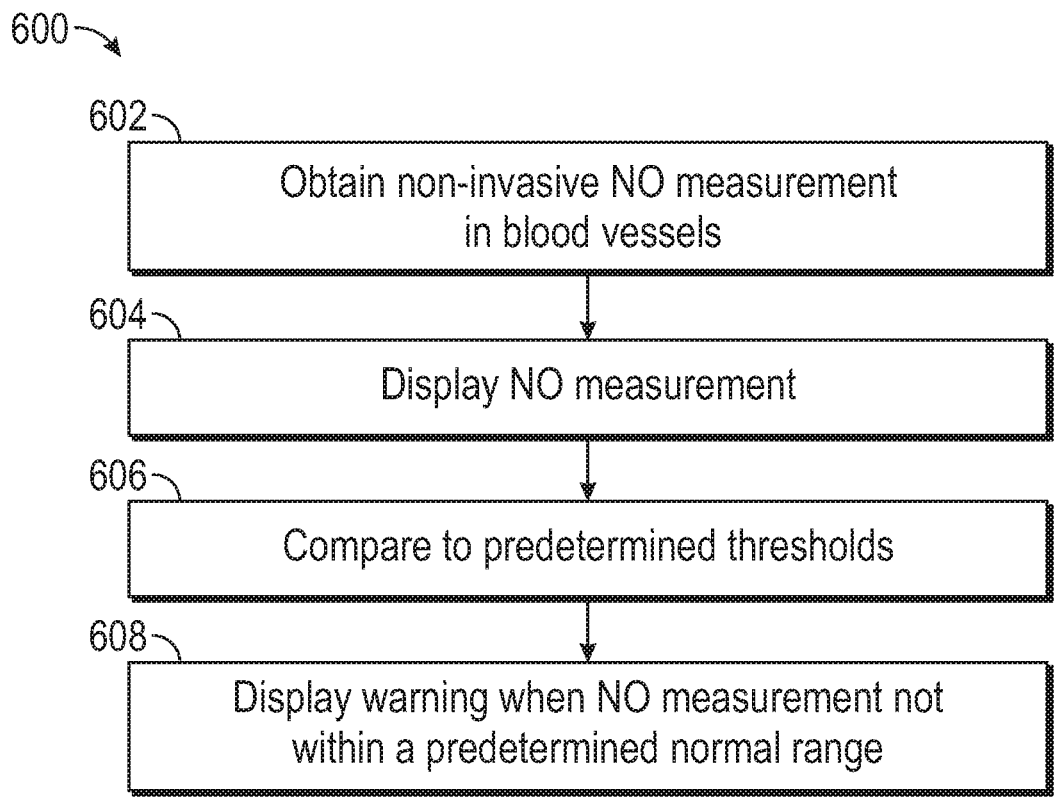
FIG. 6 illustrates a logical flow diagram of an exemplary embodiment of a method for measuring nitric oxide (NO) in blood vessels.

FIG. 6 illustrates a logical flow diagram of an exemplary embodiment of a method 600 for measuring NO in blood vessels. The biosensor 100 non-invasively obtains an NO measurement related to the concentration of NO in blood vessels at 602. The NO measurement is then displayed at 604.

A care provider may then determine health conditions or risks using the NO measurement and determine to perform additional tests or provide medical care. For example, the biosensor 100 non-invasively monitors an NO measurement, such as the NO concentration level or indicator of amount of nitric oxide, in blood vessels. The NO measurement may be represented by a saturation of nitric oxide SpNO in the blood or other values representing NO levels in the blood vessels, such as mmol/liter.

The NO measurement of a patient may be compared to predetermined levels at 606. For example, the predetermined thresholds may be a range of average or mean NO measurements of a sample healthy population. The NO measurement of an individual patient may then be compared to the normal range derived from the sample population. Depending on the comparison, the NO measurement may be determined within normal ranges. Alternatively, the NO measurement may be determined to be lower or higher than predetermined normal ranges indicating one or more health risks. For example, diabetic conditions may result in lower than normal NO levels while carbon monoxide poisoning or septic risk may result in higher than normal NO levels. Other compounds may also cause unsafe levels of NO in blood vessels, such as lidocaine and nitrates such as nitroglycerine, nitric oxide, or water sources contaminated by runoff containing nitrogen based fertilizers, anti-malaria drug dapsone, benzocaine, cyanide, anesthesia, nitroglycerin, nitrate drugs, water contaminated with nitro based fertilizers, landocaine, etc. An indication may be displayed that the NO measurement is within the predetermined normal range. In addition, a warning may be displayed when the NO measurement of the patient is not within a predetermined normal range at 608.

Embodiment—PPG Measurement of NO Levels

One or more of the embodiments of the biosensor 100 described herein is configured to detect a concentration level or indicator of one or more substances within arterial blood flow using photoplethysmography (PPG) techniques. The biosensor 100 may detect NO concentration level, insulin response, vascular health, cardiovascular sensor, cytochrome P450 proteins (e.g. one or more liver enzymes or reactions), digestion phase 1 and 2 or caloric intake. The biosensor 100 may even be configured to detect proteins or other elements or compounds associated with cancer. The biosensor 100 may also detect various electrolytes and many common blood analytic levels, such as bilirubin amount and sodium and potassium. For example, the biosensor 100 may detect sodium NACL concentration levels in the arterial blood flow to determine dehydration. The biosensor 100 may also detect blood alcohol levels in vivo in the arterial blood flow. The biosensor 100 may also detect blood pressure, peripheral oxygen ($SpO_2$ or $SaO_2$) saturation, heart rate, respiration rate or other patient vitals. Because blood flow to the skin can be modulated by multiple other physiological systems, the PPG sensor 110 may also be used to monitor breathing, hypovolemia, and other circulatory conditions.

In use, the biosensor 100 performs PPG techniques using the PPG circuit 110 to detect the concentration levels of one or more substances in blood flow. In one aspect, the biosensor 100 receives reflected light from skin tissue to obtain a spectral response. The spectral response includes a spectral curve that illustrates an intensity or power or energy at a frequency or wavelength in a spectral region of the detected light.

The ratio of the resonance absorption peaks from two different frequencies can be calculated and based on the Beer-Lambert law used to obtain various levels of substances in the blood flow. First, the spectral response of a substance or substances in the arterial blood flow is determined in a controlled environment, so that an absorption coefficient $\alpha_{g1}$ can be obtained at a first light wavelength $\lambda 1$ and at a second wavelength $\lambda 2$. According to the Beer-Lambert law, light intensity will decrease logarithmically with path length l (such as through an artery of length l). Assuming then an initial intensity $I_{in}$ of light is passed through a path length l, a concentration $C_g$ of a substance may be determined using the following equations:

At the first wavelength $\lambda_1$, $I_1 = I_{in1} * 10^{-(\alpha_{g1}C_{gw} + \alpha_{w1}C_w)*l}$ At the second wavelength $\lambda_2$, $I_2 = I_{in2} * 10^{-(\alpha_{g2}C_{gw} + \alpha_{w2}C_w)*l}$ wherein:
$I_{in1}$ is the intensity of the initial light at $\lambda_1$
$I_{in2}$ is the intensity of the initial light at $\lambda_2$
$\alpha_{g1}$ is the absorption coefficient of the substance in arterial blood at $\lambda_1$
$\alpha_{g2}$ is the absorption coefficient of the substance in arterial blood at $\lambda_2$
$\alpha_{w1}$ is the absorption coefficient of arterial blood at $\lambda_1$
$\alpha_{w2}$ is the absorption coefficient of arterial blood at $\lambda_2$
$C_{gw}$ is the concentration of the substance and arterial blood
$C_w$ is the concentration of arterial blood
Then letting R equal:

$$R = \frac{\log 10\left(\frac{I_1}{I_{in_1}}\right)}{\log 10\left(\frac{I_2}{I_{in_2}}\right)}$$

The concentration of the substance Cg may then be equal to:

$$Cg = \frac{Cgw}{Cgw + Cw} = \frac{\alpha_{w2} R - \alpha_{w1}}{(\alpha_{w2} - \alpha_{gw2}) * R - (\alpha_{w1} - \alpha_{gw1})}$$

The biosensor 100 may thus determine the concentration of various substances in arterial blood using spectroscopy of at least two different wavelengths from the Beer-Lambert principles. For example, the biosensor 100 may function as a pulse oximeter using similar principles under Beer-lambert law to determine pulse and oxygen saturation levels in pulsating arterial blood flow. For example, a first wavelength at approximately 940 nm and a second wavelength at approximately 660 nm may be used to determine oxygen saturation levels ($SpO_2$). In addition, the biosensor 100 may determine concentration levels of one or more additional substances in blood vessels.

Figure 7:
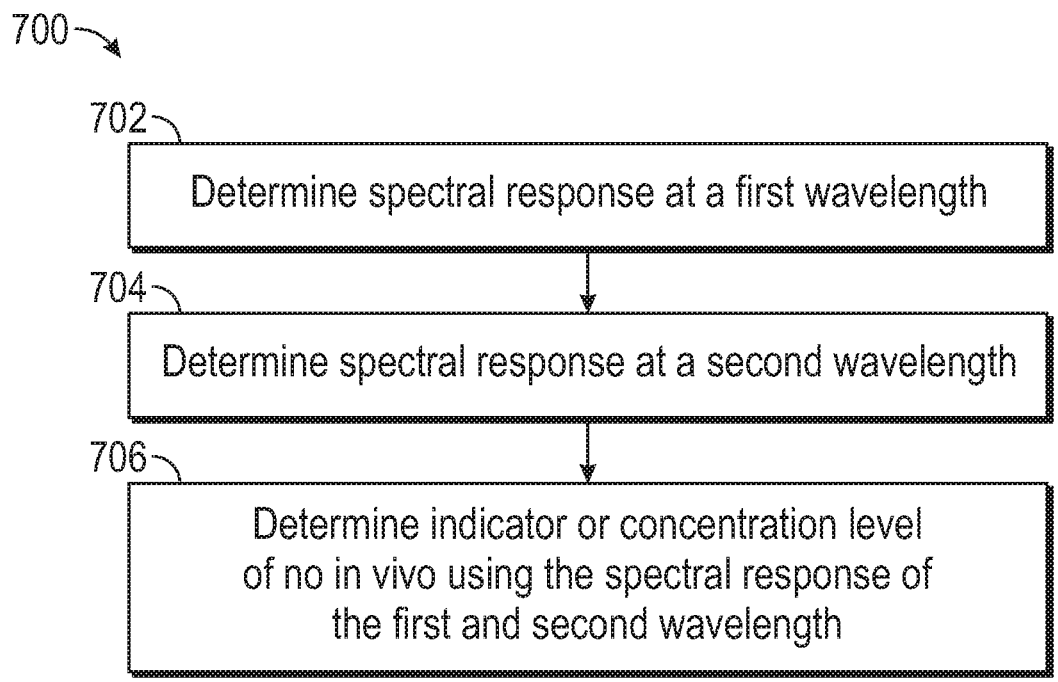
FIG. 7 illustrates a logical flow diagram of an embodiment of a method for determining concentration of one or more additional substances using Beer-Lambert principles.

FIG. 7 illustrates a logical flow diagram of an embodiment of a method 700 for determining concentration level of NO using Beer-Lambert principles. The biosensor 100 transmits light at least at a first predetermined wavelength and at a second predetermined wavelength. The biosensor 100 detects the light (reflected from the skin or transmitted through the skin) and determines the spectral response at the first wavelength at 702 and at the second wavelength at 704. The biosensor 100 then determines an indicator or concentration level of NO using the spectral responses of the first and second wavelength at 706. In general, the first predetermined wavelength is selected that has a high absorption coefficient for No while the second predetermined wavelength is selected that has a lower absorption coefficient for NO. Thus, it is generally desired that the spectral response for the first predetermined wavelength have a higher intensity level in response to NO than the spectral response for the second predetermined wavelength.

In another aspect, the biosensor 100 may transmit light at the first predetermined wavelength in a range of approximately 1 nm to 50 nm around the first predetermined wavelength. Similarly, the biosensor 100 may transmit light at the second predetermined wavelength in a range of approximately 1 nm to 50 nm around the second predetermined wavelength. The range of wavelengths is determined based on the spectral response since a spectral response may extend over a range of frequencies, not a single frequency (i.e., it has a nonzero linewidth). The light that is reflected or transmitted by NO may spread over a range of wavelengths rather than just the single predetermined wavelength. In addition, the center of the spectral response may be shifted from its nominal central wavelength or the predetermined wavelength. The range of 1 nm to 50 nm is based on the bandwidth of the spectral response line and should include wavelengths with increased light intensity detected for the targeted substance around the predetermined wavelength.

The first spectral response of the light over the first range of wavelengths including the first predetermined wavelength and the second spectral response of the light over the second range of wavelengths including the second predetermined wavelengths is then generated at 702 and 704. The biosensor 100 analyzes the first and second spectral responses to detect an indicator or concentration level of NO in the arterial blood flow at 706.

Figure 8A:
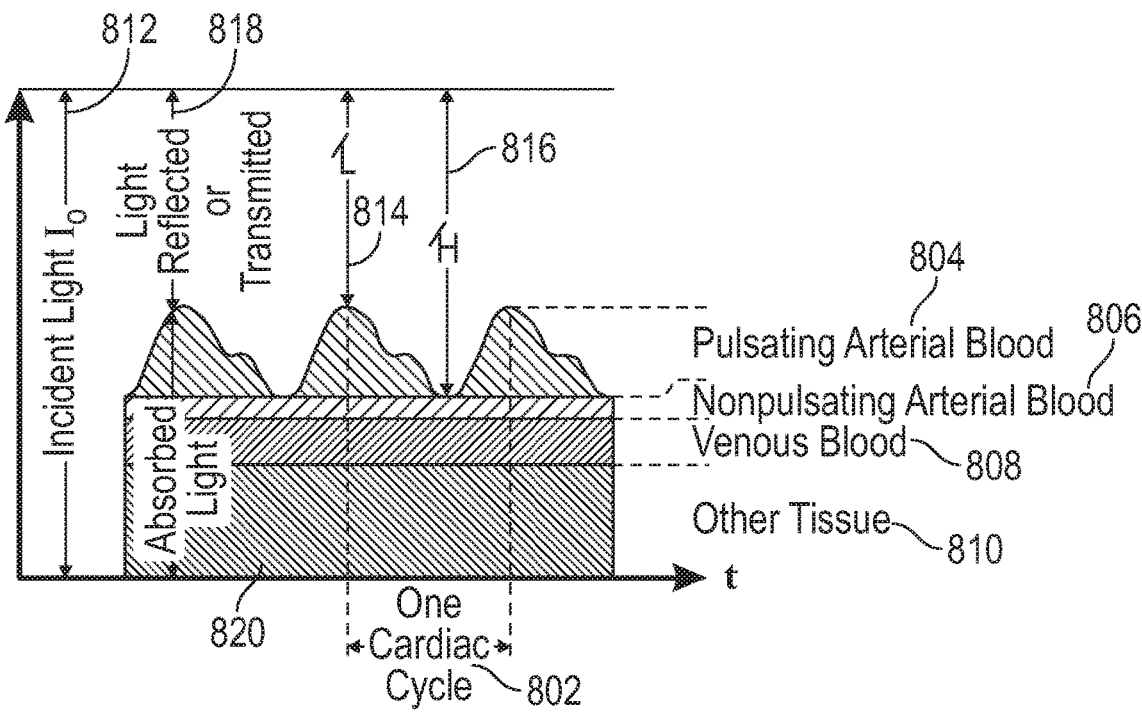
FIG. 8A and FIG. 8B illustrate schematic block diagrams of an embodiment of a method for photoplethysmography (PPG) techniques in more detail.
Figure 8B:
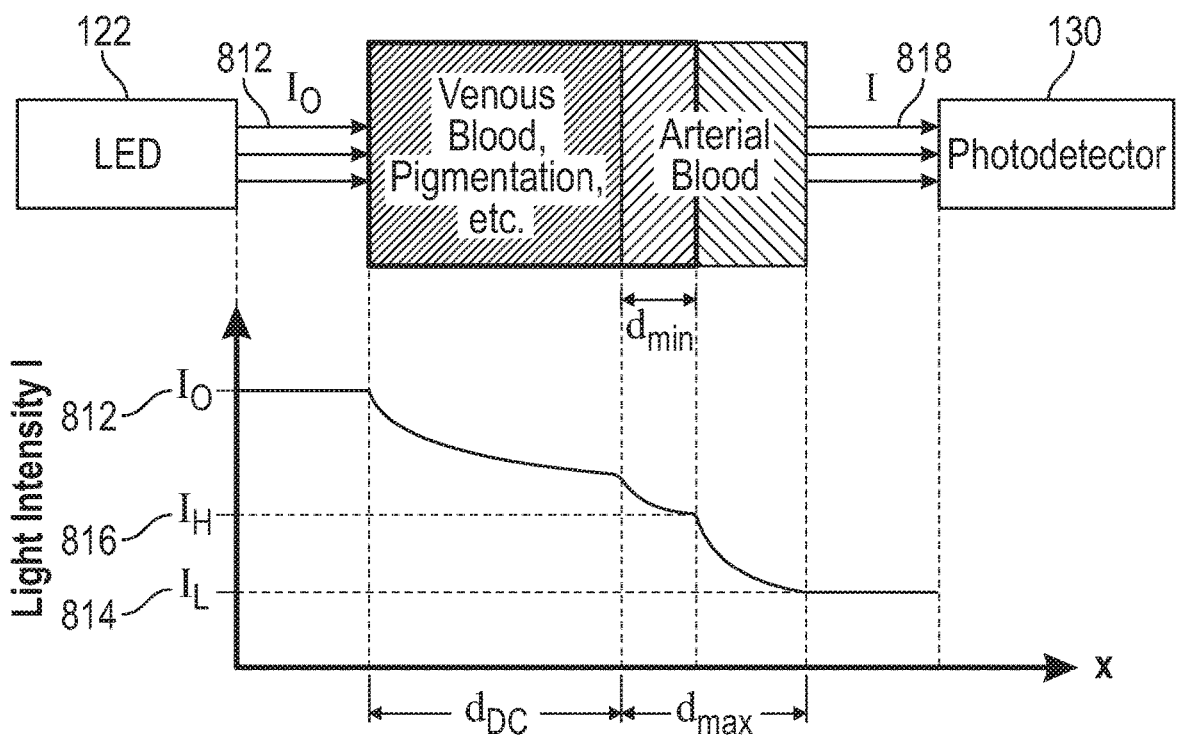

FIG. 8A and FIG. 8B illustrate schematic block diagrams of an embodiment of a method for photoplethysmography (PPG) techniques in more detail. Photoplethysmography (PPG) is used to measure time-dependent volumetric properties of blood in blood vessels due to the cardiac cycle. For example, the heartbeat affects volume of arterial blood flow and the concentration of absorption levels being measured in the arterial blood flow. As shown in FIG. 8A, over a cardiac cycle 802, pulsating arterial blood 804 changes the volume of blood flow in an artery.

Incident light $I_O$ 812 is directed at a tissue site and a certain amount of light is reflected or transmitted 818 and a certain amount of light is absorbed 820. At a peak of arterial blood flow or arterial volume, the reflected/transmitted light $I_L$ 814 is at a minimum due to absorption by the venous blood 808, nonpulsating arterial blood 806, pulsating arterial blood 804, other tissue 810, etc. At a minimum of arterial blood flow or arterial volume during the cardiac cycle, the transmitted/reflected light $I_H$ 816 is at a maximum due to lack of absorption from the pulsating arterial blood 804.

The biosensor 100 is configured to filter the reflected/transmitted light $I_L$ 814 of the pulsating arterial blood 804 from the transmitted/reflected light $I_H$ 816. This filtering isolates the light due to reflection/transmission of substances in the pulsating arterial blood 804 from the light due to reflection/transmission from venous (or capillary) blood 808, other tissues 810, etc. The biosensor 100 may then measure the concentration levels of one or more substances from the reflected/transmitted light $I_L$ 814 in the pulsating arterial blood 804.

For example, as shown in FIG. 8B, incident light $I_O$ 812 is directed at a tissue site by an LED 122 at one or more wavelengths. The reflected/transmitted light I 818 is detected by photodetector 130. At a peak of arterial blood flow or arterial volume, the reflected light $I_L$ 814 is at a minimum due to absorption by venous blood 808, non-pulsating arterial blood 806, pulsating arterial blood 804, other tissue 810, etc. At a minimum of arterial blood flow or arterial volume during the cardiac cycle, the Incident or reflected light $I_H$ 816 is at a maximum due to lack of absorption from the pulsating arterial blood 804. Since the light I 818 is reflected or traverses through a different volume of blood at the two measurement times, the measurement provided by a PPG sensor is said to be a 'volumetric measurement' descriptive of the differential volumes of blood present at a certain location within the patient's arteriolar bed at different times. Though the above has been described with respect to arterial blood flow, the same principles described herein may be applied to venous blood flow.

In general, the relative magnitudes of the AC and DC contributions to the reflected/transmitted light signal I 818 may be used to substantially determine the differences between the diastolic time and the systolic points. In this case, the difference between the reflected light $I_L$ 814 and reflected light $I_H$ 816 corresponds to the AC contribution of the reflected light 818 (e.g. due to the pulsating arterial blood flow). A difference function may thus be computed to determine the relative magnitudes of the AC and DC components of the reflected light I 818 to determine the magnitude of the reflected light $I_L$ 814 due to the pulsating arterial blood 804. The described techniques herein for determining the relative magnitudes of the AC and DC contributions is not intended as limiting. It will be appreciated that other methods may be employed to isolate or otherwise determine the relative magnitude of the light $I_L$ 814 due to pulsating arterial blood flow.

FIG. 9 illustrates a schematic diagram of a graph of actual clinical data obtained using an embodiment of the biosensor 100 and PPG techniques at a plurality of wavelengths. In one aspect, the biosensor 100 is configured to emit light having a plurality of wavelengths during a measurement period. The light at each wavelength (or range of wavelengths) may be transmitted concurrently or sequentially. The intensity of the reflected light at each of the wavelengths (or range of wavelengths) is detected and the spectral response is measured over the measurement period. The spectral response 908 for the plurality of wavelengths obtained using an embodiment of the biosensor in clinical trials is shown in FIG. 9. In this clinical trial, two biosensors 100 attached to two separate fingertips of a patient were used to obtain the spectral responses 908. The first biosensor 100 obtained the spectral response for a wavelength at 940 nm 610, a wavelength at 660 nm 612 and a wavelength at 390 nm 614. The second biosensor 100 obtained the spectral response for a wavelength at 940 nm 616, a wavelength at 592 nm 618 and a wavelength at 468 nm 620.

In one aspect, the spectral response of each wavelength may be aligned based on the systolic 602 and diastolic 604 points in their spectral responses. This alignment is useful to associate each spectral response with a particular stage or phase of the pulse-induced local pressure wave within the blood vessel (which may mimic the cardiac cycle 906 and thus include systolic and diastolic stages and sub-stages thereof). This temporal alignment helps to determine the absorption measurements acquired near a systolic point in time of the cardiac cycle and near the diastolic point in time of the cardiac cycle 906 associated with the local pressure wave within the patient's blood vessels. This measured local pulse timing information may be useful for properly interpreting the absorption measurements in order to determine the relative contributions of the AC and DC components measured by the biosensor 100. So for one or more wavelengths, the systolic points 902 and diastolic points 904 in the spectral response are determined. These systolic points 902 and diastolic points 904 for the one or more wavelengths may then be aligned as a method to discern concurrent responses across the one or more wavelengths.

In another embodiment, the the systolic points 902 and diastolic points 904 in the absorbance measurements are temporally correlated to the pulse-driven pressure wave within the arterial blood vessels—which may differ from the cardiac cycle. In another embodiment, the biosensor 100 may concurrently measure the intensity reflected at each the plurality of wavelengths. Since the measurements are concurrent, no alignment of the spectral responses of the plurality of wavelengths may be necessary. FIG. 9 illustrates the spectral response of the plurality of wavelengths with the systolic points 902 and diastolic points 904 aligned.

Figure 10:
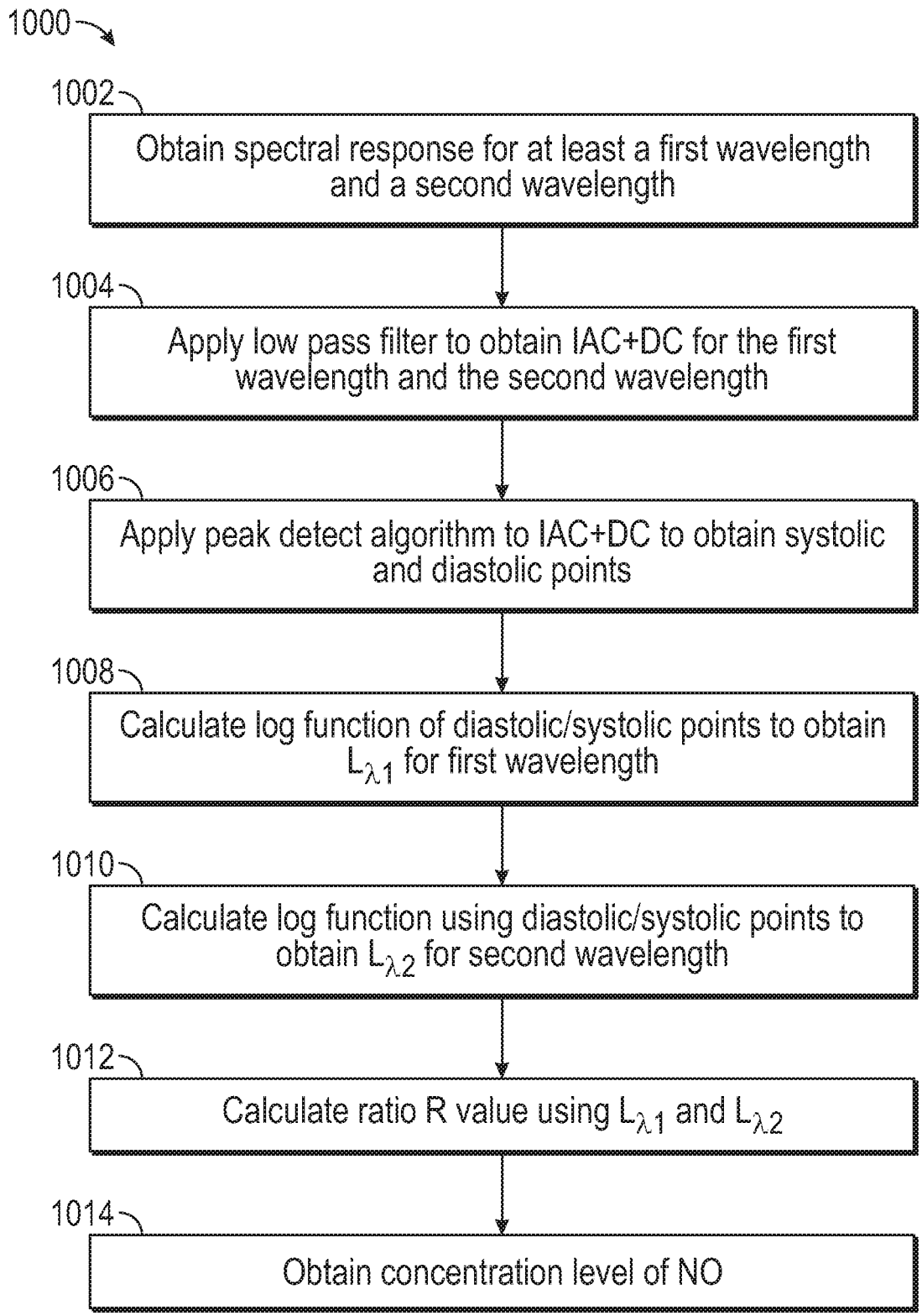
FIG. 10 illustrates a logical flow diagram of an embodiment of a method of the biosensor.

FIG. 10 illustrates a logical flow diagram of an embodiment of a method 1000 of the biosensor 100. In one aspect, the biosensor 100 emits and detects light at a plurality of predetermined frequencies or wavelengths, such as approximately 940 nm, 660 nm, 390 nm, 592 nm, and 468 nm. The light is pulsed for a predetermined period of time (such as 100 usec or 200 Hz) sequentially or simultaneously at each predetermined wavelength. In another aspect, light may be pulsed in a wavelength range of 1 nm to 50 nm around each of the predetermined wavelengths. For example, for the predetermined wavelength 390 nm, the biosensor 100 may transmit light directed at skin tissue of the patient in a range of 360 nm to 410 nm including the predetermined wavelength 390 nm. For the predetermined wavelength of 940 nm, the biosensor 100 may transmit light directed at the skin tissue of the patient in a range of 920 nm to 975 nm. In another embodiment, the light is pulsed simultaneously at least at each of the predetermined wavelengths (and in a range around the wavelengths).

The spectral responses are obtained around the plurality of wavelengths, including at least a first wavelength and a second wavelength at 1002. The spectral responses may be measured over a predetermined period (such as 300 usec.). This measurement process is repeated continuously, e.g., pulsing the light at 10-100 Hz and obtaining spectral responses over a desired measurement period, e.g. from 1-2 seconds to 1-2 minutes or from 2-3 hours to continuously over days or weeks. The absorption levels are measured over one or more cardiac cycles and systolic and diastolic points of the spectral response are determined. Because the human pulse is typically on the order of magnitude of one 1 Hz, typically the time differences between the systolic and diastolic points are on the order of magnitude of milliseconds or tens of milliseconds or hundreds of milliseconds. Thus, spectral response measurements may be obtained at a frequency of around 10-100 Hz over the desired measurement period. The spectral responses are obtained over one or more cardiac cycles and systolic and diastolic points of the spectral responses are determined.

A low pass filter (such as a 5 Hz low pass filter) is applied to the spectral response signal at 1004. The relative contributions of the AC and DC components are obtained $I_{AC+DC}$ and $I_{AC}$. A peak detection algorithm is applied to determine the systolic and diastolic points at 1006. The systolic and diastolic points of the spectral response for each of the wavelengths may be aligned and may also be aligned with systolic and diastolic points of an arterial pulse waveform or cardiac cycle.

Beer Lambert equations are then applied as described herein at 1008. For example, the $L_\lambda$ values are then calculated for the wavelengths λ, wherein the $L_\lambda$ values for a wavelength equals:

$$L_\lambda = \text{Log}10\left(\frac{IAC + DC}{IDC}\right)$$

wherein $I_{AC+DC}$ is the intensity of the detected light with AC and DC components and $I_{DC}$ is the intensity of the detected light with the AC filtered by the low pass filter. The value $L_\lambda$ isolates the spectral response due to pulsating arterial blood flow, e.g. the AC component of the spectral response.

A ratio R of the $L_\lambda$ values at two wavelengths may then be determined. For example, $$\text{Ratio } R = \frac{L\lambda 1}{L\lambda 2}$$

The spectral responses may be measured and the $L_\lambda$ values and Ratio R determined continuously, e.g. every 1-2 seconds, and the obtained $L_\lambda$ values and/or Ratio R averaged over a predetermined time period, such as over 1-2 minutes. The NO concentration levels may then be obtained from the averaged R values and a calibration database. The NO level measurements are then displayed. The biosensor 100 may continuously monitor a patient over 2-3 hours or continuously over days or weeks.

The $R_{390,940}$ value with $L_{\lambda 1=390\ nm}$ and $L_{\lambda 2=940}$ may be non-invasively and quickly and easily obtained using the biosensor 100 in a physician's office or other clinical setting or at home. In particular, in unexpected results, it is believed that nitric oxide NO levels in the arterial blood flow is being measured at least in part by the biosensor 100 at $\lambda_1$=390 nm. The wavelengths around 390 nm may also be used, e.g. 395 nm or a range from 370 nm to 410 nm. Since NO is partly in a gaseous form in blood vessels (prior to adhesion to hemoglobin), the total NO concentration levels of in vitro blood samples, e.g. from a finger prick, are not detected as the NO gas dissipates. Thus, the biosensor 100 measurements to determine the $L_{390\ nm}$ values are the first time NO concentration levels in arterial blood flow have been measured directly in vivo. These and other aspects of the biosensor 100 are described in more detail herein with clinical trial results.

Figure 11:
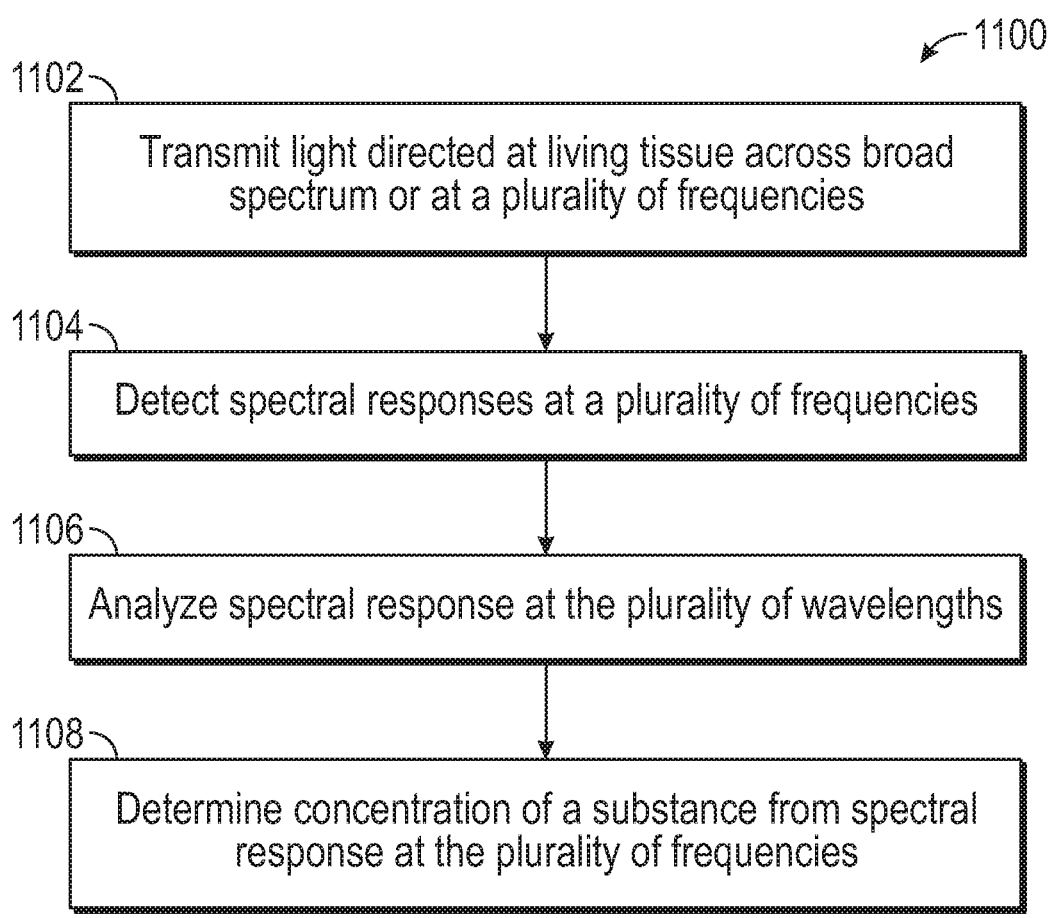
FIG. 11 illustrates a logical flow diagram of an exemplary method to determine levels of NO using the spectral response at a plurality of wavelengths.

Embodiment—Determination of NO Concentration Levels at a Plurality of Wavelengths FIG. 11 illustrates a logical flow diagram of an exemplary method 1100 to determine levels of NO using the spectral response at a plurality of wavelengths. The absorption coefficient may be higher at other wavelengths due to NO or NO isoforms or NO compounds. For example, the increased intensity of light at a plurality of wavelengths may be due to reflectance by NO or NO isoforms or other NO compounds in the arterial blood flow. Another method for determining NO levels may then be used by measuring the spectral response and determining L and R values at a plurality of different wavelengths of light. In this example then, NO concentration level is determined over multiple wavelengths. An example for calculating the concentration of one or more substances over multiple wavelengths may be performed using a linear function, such as is illustrated herein below.

$$LN(I_{1-n}) = \Sigma_{i=0}^{n} \mu i * Ci$$

wherein, $I_{1-n}$=intensity of light at wavelengths $\lambda_{1-n}$ $\mu_n$=absorption coefficient of substance 1, 2, . . . n at wavelengths $\lambda_{1-n}$ $C_n$=Concentration level of substance 1, 2, . . . n When the absorption coefficients $\mu_{1-n}$ of NO or NOS isoforms or other NO compounds are known at the wavelengths $\lambda_{1-n}$, then the concentration level C of the substances may be determined from the spectral responses at the wavelengths $\lambda_{1-n}$ (and e.g., including a range of 1 nm to 50 nm around each of the wavelengths). The concentration level of NO may be isolated from the NOS isoforms or other NO compounds by compensating for the concentration of the hemoglobin compounds. Thus, using the spectral responses at multiple frequencies provides a more robust determination of the concentration level of NO.

In use, the biosensor 100 transmits light directed at skin tissue at a plurality of wavelengths or over a broad spectrum at 1102. The spectral response of light from the skin tissue is detected at 1104, and the spectral response is analyzed for a plurality of wavelengths (and in one aspect including a range of +/− 10 to 50 nm around each of the wavelengths) at 1106. Then, the concentration level C of the substance may be determined using the spectral response at the plurality of wavelengths at 1108.

Figure 12:
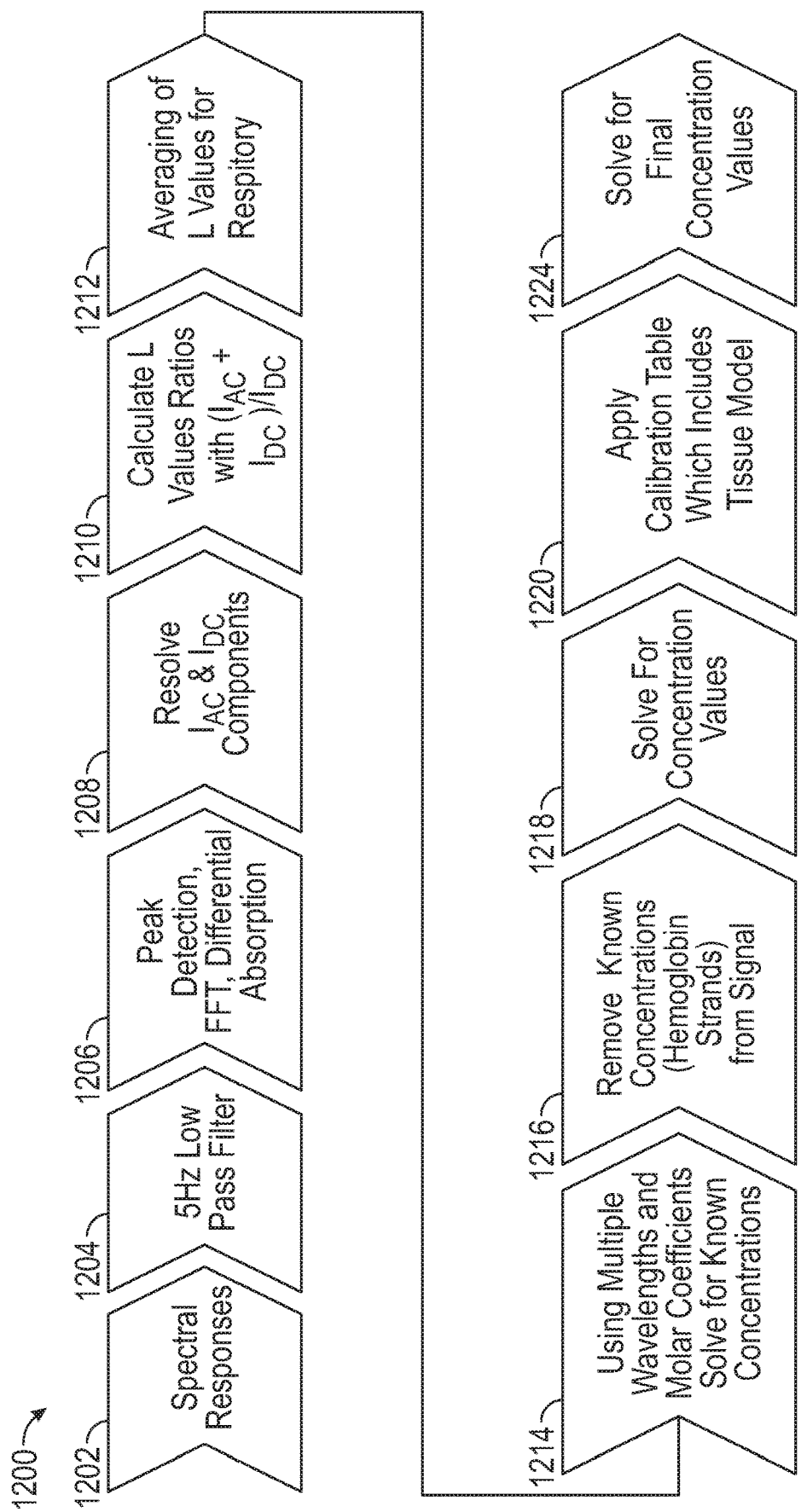
FIG. 12 illustrates a logical flow diagram of an exemplary method to determine levels of NO using the spectral response at a plurality of wavelengths in more detail.

FIG. 12 illustrates a logical flow diagram of an exemplary method 1200 to determine levels of NO using the spectral response at a plurality of wavelengths in more detail. The spectral responses are obtained at 1202. The spectral response signals include AC and DC components $I_{AC+DC}$. A low pass filter (such as a 5 Hz low pass filter) is applied to each of the spectral response signals $I_{AC+DC}$ to isolate the DC component of each of the spectral response signals $I_{DC}$ at 1204. The AC fluctuation is due to the pulsatile expansion of the arteriolar bed due to the volume increase in arterial blood. In order to measure the AC fluctuation, measurements are taken at different times and a peak detection algorithm is used to determine the diastolic point and the systolic point of the spectral responses at 1206. Fast Fourier transform (FFT) or differential absorption techniques may also be used to isolate the DC component of each spectral response signal. The various methods include one or more of: Peak & Valley (e.g., peak detection), FFT, and differential absorption. Each of the methods require different amounts of computational time which affects overall embedded computing time for each signal, and therefore can be optimized and selectively validated with empirical data through large clinical sample studies.

The $I_{AC+DC}$ and $I_{DC}$ components are then used to compute the L values at 1210. For example, a logarithmic function may be applied to the ratio of $I_{AC+DC}$ and $I_{DC}$ to obtain an L value for each of the wavelengths $L_{\lambda 1-n}$. Since the respiratory cycle affects the PPG signals, the L values may be averaged over a respiratory cycle and/or over another predetermined time period (such as over a 1-2 minute time period).

In an embodiment, NO isoforms may be attached in the blood stream to one or more hemoglobin compounds. The concentration level of the hemoglobin compounds may then need to be accounted for to isolate the concentration level of NO from the hemoglobin compounds. For example, nitric oxide (NO) is found in the blood stream in a gaseous form and also attached to hemoglobin compounds as described herein. Thus, the spectral responses obtained around 390 nm may include a concentration level of the hemoglobin compounds as well as nitric oxide. The hemoglobin compound concentration levels must thus be compensated for to isolate the nitric oxide concentration levels. Multiple wavelengths and absorption coefficients for hemoglobin are used to determine a concentration of the hemoglobin compounds at 1214. This process is discussed in more detail herein below. Other methods may also be used to obtain a concentration level of hemoglobin in the arterial blood flow as explained herein. The concentration of the hemoglobin compounds is then adjusted from the concentration level of NO at 1216. The R values are then determined at 1218.

To determine a concentration level of NO, a calibration database is used that associates R values to concentration levels of NO at 1220. The calibration database correlates the R value with an NO concentration level. The calibration database may be generated for a specific patient or may be generated from clinical data of a large sample population. It is determined that the R values should correlate to similar NO concentration levels across a large sample population. Thus, the calibration database may be generated from testing of a large sample of a general population.

In addition, the R values may vary depending on various factors, such as underlying skin tissue. For example, the R values may vary for spectral responses obtained from an abdominal area versus measurements from a wrist or finger due to the varying tissue characteristics. The calibration database may thus provide different correlations between the R values and NO concentration levels depending on the underlying skin tissue characteristics.

The NO concentration level is then obtained at 1224. The NO concentration level may be expressed as mmol/liter, as a saturation level percentage, as a relative level on a scale, etc. In order to remove the hemoglobin concentration(s) from the original PPG signals, a mapping function may be created which is constructed through clinical data and tissue modeling. For example, known $SpO_2$ values in the infrared region and the same signals at the UV side of the spectrum are obtained. Then a linear inversion map can be constructed where the R values are input into a function and the desired concentration(s) can be determined. For example, a curve that correlates R values to concentration levels (similar to FIG. 33 for $SpO_2$) may be tabulated. A polynomial equation with multiple factors can also be used to account for different R values to represent the linear inversion map. This correlation may be derived from validated clinical data.

Figure 33:
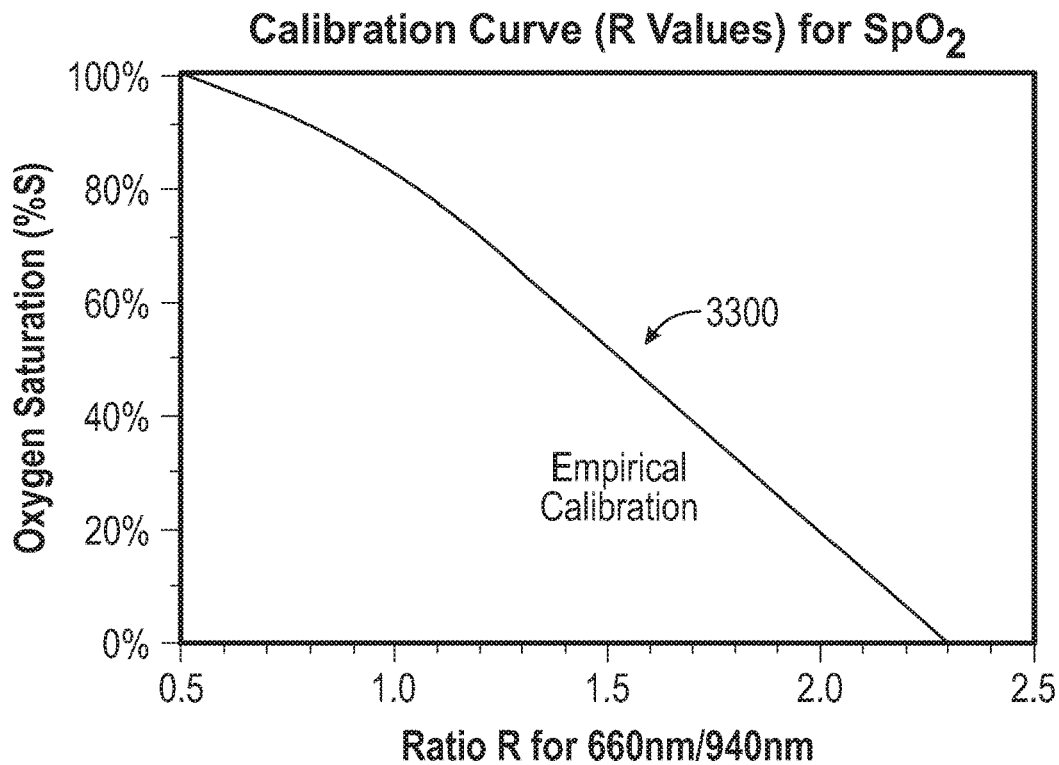
FIG. 33 illustrates a schematic drawing of an exemplary embodiment of a calibration curve for correlating oxygen saturation levels (SpO2) with R values.

For example, a regression curve similar to the curve in FIG. 33 that correlates R values and $SpO_2$ may be generated for each substance based on clinical data from a large general population. A polynomial may be derived from the curve and used to solve for a concentration level from the R value. The polynomial is stored in the calibration database and may be used rather than using a calibration look-up table or curve.

Embodiment—Determination of a Concentration of Hemoglobin Compounds

The Beer-Lambert theory may be generalized for a multi-wavelength system to determine a concentration of known hemoglobin species using the following matrix notation:

$$\begin{bmatrix} dA_{\lambda 1}^{LB} \\ \vdots \\ dA_{\lambda n}^{LB} \end{bmatrix} = \begin{bmatrix} \Delta l_{\lambda 1} & \cdots & 0 \\ \vdots & \ddots & \vdots \\ 0 & \cdots & \Delta l_{\lambda n} \end{bmatrix} \begin{bmatrix} \varepsilon_{\lambda 1, HbX_1} & \cdots & \varepsilon_{\lambda 1, HbX_m} \\ \vdots & \ddots & \vdots \\ \varepsilon_{\lambda n, HbX_1} & \cdots & \varepsilon_{\lambda n, HbX_m} \end{bmatrix} \cdot \begin{bmatrix} HbX_1 \\ \vdots \\ HbX_m \end{bmatrix} \cdot c(Hb),$$

wherein $dA_\lambda^{LB}$ is a differential absorption within the Beer-Lambert model $\varepsilon_{\lambda n, HbX_1}$ is an extinction coefficient HbX are hemoglobin fractions $\Delta l\lambda$ is the optical path-length for wavelength $\lambda$ c(Hb) is the hemoglobin concentration This matrix equation for determining hemoglobin concentration levels may be solved when m is equal or greater than n, e.g., which means that at least four wavelengths are needed to solve for four hemoglobin species.

Figure 13:
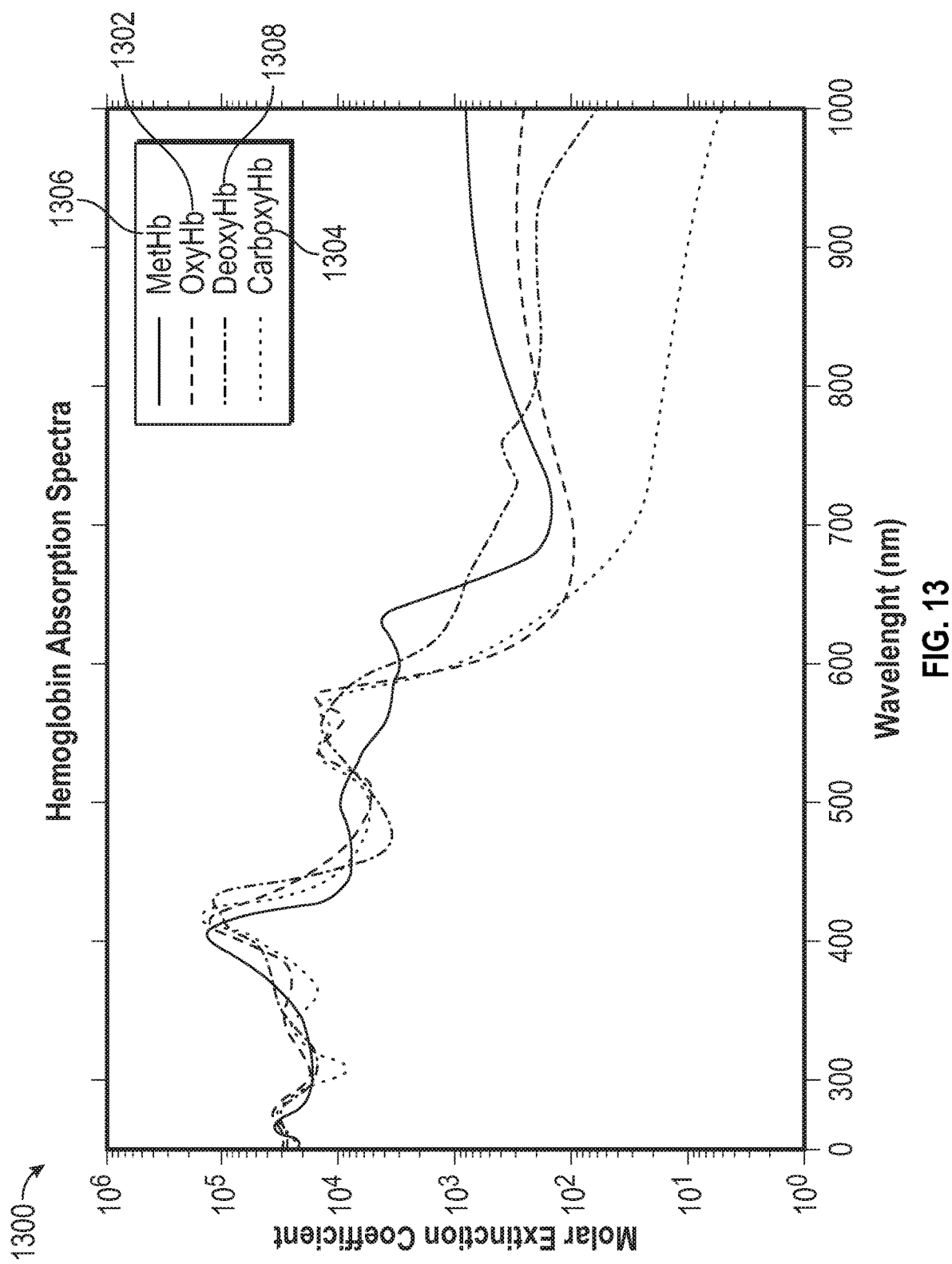
FIG. 13 illustrates a schematic block diagram of an exemplary embodiment of a graph illustrating the extinction coefficients over a range of frequencies for a plurality of hemoglobin species.

FIG. 13 illustrates a schematic block diagram of an exemplary embodiment of a graph 1300 illustrating the extinction coefficients over a range of frequencies for a plurality of hemoglobin species. The hemoglobin species include, e.g., Oxyhemoglobin [$HbO_2$ or OxyHb] 1302, Carboxyhemoglobin [HbCO or CarboxyHb] 1304, Methemoglobin [HbMet or MetHb] 1306, and deoxygenated hemoglobin (DeoxyHb or RHb) 1308. A method for determining the relative concentration or composition of hemoglobin species included in blood is described in more detail in U.S. Pat. No. 6,104,938 issued on Aug. 15, 2000, which is hereby incorporated by reference herein.

A direct calibration method for calculating hemoglobin species may be implemented by the biosensor 100. Using four wavelengths and applying a direct model for four hemoglobin species in the blood, the following equation results:

$$HbX = \frac{a_1 * dA_1 + a_2 * dA_2 + a_3 * dA_3 + a_4 * dA_4}{b_1 * dA_1 + b_2 * dA_2 + b_3 * dA_3 + b_4 * dA_4}$$

wherein $dA_\lambda$ is the differential absorption signal $a_n$ and $b_n$ are calibration coefficients The calibration coefficients $a_n$ and $b_n$ may be experimentally determined over a large population average. The biosensor 100 may include a calibration database to account for variances in the calibration coefficients $a_1$ and $b_1$ (or extinction coefficients) for the hemoglobin species for various underlying tissue characteristics.

A two-stage statistical calibration and measurement method for performing PPG measurement of blood analyte concentrations may also be implemented by the biosensor 100. Concentrations of MetHb, $HbO_2$, RHb and HbCO are estimated by first estimating a concentration of MetHb (in a first stage) and subsequently, if the concentration of MetHb is within a predetermined range, then the estimated concentration of MetHb is assumed to be accurate and this estimated concentration of MetHb is utilized as a "known value" in determining the concentrations of the remaining analytes $HbO_2$, RHb and HbCO (in a second stage). This method for determining a concentration of hemoglobin species using a two stage calibration and analyte measurement method is described in more detail in U.S. Pat. No. 5,891,024 issued on Apr. 6, 1999, which is hereby incorporated by reference herein.

The concentration of the hemoglobin compounds may thus be determined and then the hemoglobin concentration removed when determining the concentration level of NO by the biosensor 100. Though several methods are described herein for obtaining a concentration of hemoglobin analytes, other methods or processes may be used by the biosensor 100 to determine the concentration of hemoglobin analytes or otherwise adjusting the obtained measurements to account for a hemoglobin concentration when determining the concentration levels of NO in a blood stream.

Embodiment—Determination of NO Concentration Levels using Shifts in Absorbance Peaks In another embodiment, a concentration level of NO may be obtained from measuring a characteristic shift in an absorbance peak of hemoglobin. For example, the absorbance peak for methemoglobin shifts from around 433 nm to 406 nm in the presence of NO. The advantage of the measurement of NO by monitoring methemoglobin production includes the wide availability of spectrophotometers, avoidance of sample acidification, and the relative stability of methemoglobin. Furthermore, as the reduced hemoglobin is present from the beginning of an experiment, NO synthesis can be measured continuously, removing the uncertainty as to when to sample for NO.

Figure 14:
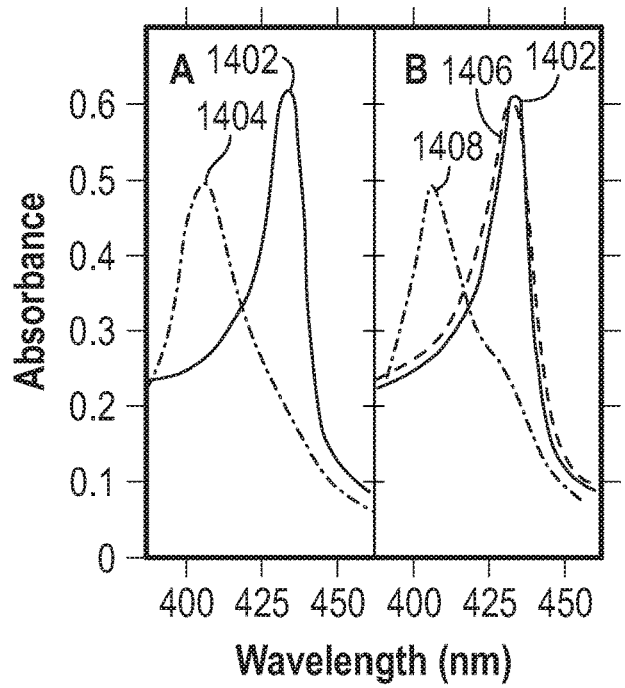
FIG. 14 illustrates a schematic block diagram of an exemplary embodiment of a graph illustrating a shift in absorbance peaks of hemoglobin in the presence of NO.

FIG. 14 illustrates a schematic block diagram of an exemplary embodiment of a graph 1400 illustrating a shift in absorbance peaks of hemoglobin in the presence of NO. In graph A, the curve 1402 illustrates the absorbance spectra of reduced hemoglobin. The addition of nitric oxide (NO) shifts the absorbance spectra curve 1404 to a lower wavelength due to the production of methemoglobin. In graph B, the absorbance spectra curve of reduced hemoglobin 1402 is again illustrated. Endothelial cells are then added and the absorbance spectra measured again. The curve 1406 illustrates that little change occurs in the absorbance spectra curve 1402 of reduced hemoglobin in the presence of unstimulated endothelial cells. The curve 1408 illustrates the production of methemoglobin when the same dose of endothelial cells was given after stimulation of EDRF synthesis by the ionophore.

Though the absorbance spectrums shown in the graph 1400 were measured using in vitro assays, the biosensor 100 may detect nitric oxide in vivo using PPG techniques by measuring the shift in the absorbance spectra curve of reduced hemoglobin 1402 in tissue and/or arterial blood flow. The absorbance spectra curve 1402 shifts with a peak from around 430 nm to a peak around 411 nm depending on the production of methemoglobin. The greater the degree of the shift of the peak of the curve 1402, the higher the production of methemoglobin and NO concentration level. Correlations may be determined between the degree of the measured shift in the absorbance spectra curve 1402 of reduced hemoglobin to an NO concentration level. The correlations may be determined from a large sample population or for a particular patient and stored in a calibration database. The biosensor 100 may thus obtain an NO concentration level by measuring the shift of the absorbance spectra curve 1402 of reduced hemoglobin.

Figure 15:
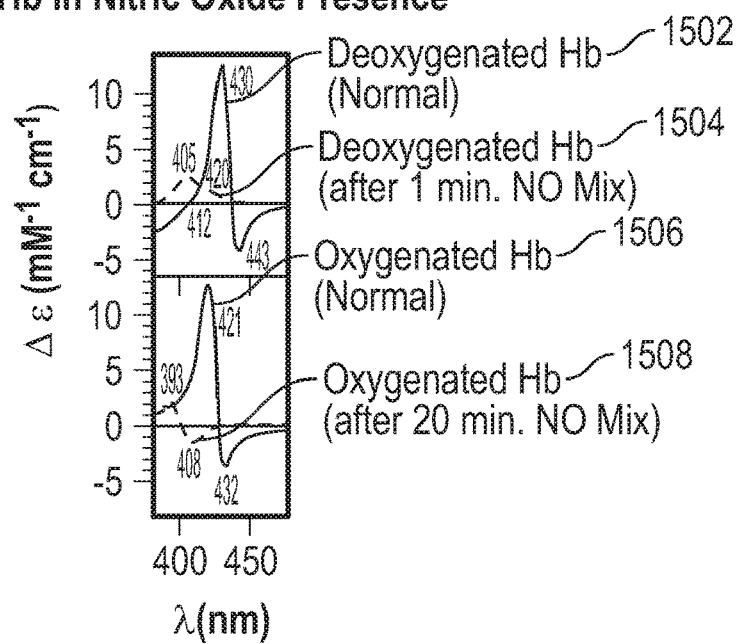
FIG. 15 illustrates a schematic block diagram of an exemplary embodiment of a graph illustrating a shift in absorbance peaks of oxygenated and deoxygenated hemoglobin (HB) in the presence of NO.

FIG. 15 illustrates a schematic block diagram of an exemplary embodiment of a graph 1500 illustrating a shift in absorbance peaks of oxygenated and deoxygenated hemoglobin (HB) in the presence of nitric oxide NO. The absorbance spectra curve 1502 of deoxygenated HB has a peak of around 430 nm in an absence of NO. After a one minute time period of exposure to a nitric oxide mixture, the absorbance spectra curve 1504 of deoxygenated HB shifted to a peak of around 405 nm in an absence of NO. In addition, the absorbance spectra curve 1506 of oxygenated HB has a peak around 421 nm. After a twenty minute time period of exposure to a nitric oxide mixture, the absorbance spectra curve 1508 of oxygenated HB shifted to a peak of around 393 nm. The Deoxygenated Hb has an absorption peak at 430 nm (1502) and in the presence of NO has a peak shift to 405 nm (1504). The Oxygenated Hb has absorption peak at 421 nm (1506) in an absence of NO and in the presence of NO has peak shift to 393 nm (1508).

Though the absorbance spectrums shown in the graph 1500 were measured using in vitro assays, the biosensor 100 may obtain an NO concentration level by measuring the shift of the absorbance spectra curve 1502 of deoxygenated hemoglobin and/or by measuring the shift of the absorbance spectra curve 1506 of oxygenated hemoglobin in vivo. The biosensor 100 may then access a calibration database that correlates the measured shift in the absorbance spectra curve 1502 of deoxygenated hemoglobin to an NO concentration level. Similarly, the biosensor may access a calibration database that correlates the measured shift in the absorbance spectra curve 1506 of oxygenated hemoglobin to an NO concentration level.

Figure 16:
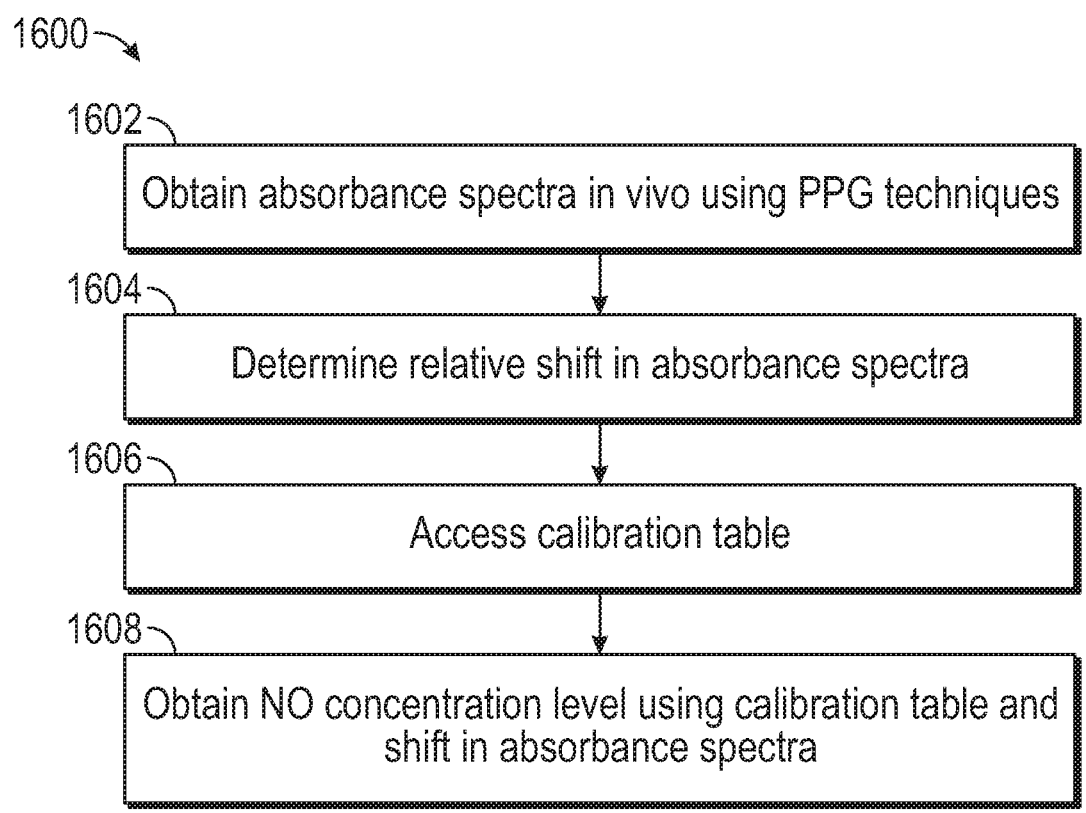
FIG. 16 illustrates a logical flow diagram of an exemplary embodiment of a method for measuring NO concentration levels in vivo using shifts in absorbance spectra.

FIG. 16 illustrates a logical flow diagram of an exemplary embodiment of a method 1600 for measuring NO concentration levels in vivo using shifts in absorbance spectra. The biosensor 100 may obtain a concentration of NO by measuring shifts in absorbance spectra of one or more substances that interact with NO. For example, the one or more substances may include oxygenated and deoxygenated hemoglobin (HB). The PPG circuit 110 detects a spectral response at a plurality of wavelengths of the one or more substances that interact with NO at 1602. The biosensor 100 determines the relative shift in the absorbance spectra for the substance at 1604. For example, the biosensor 100 may measure the absorbance spectra curve 1502 of deoxygenated HB and determine its relative shift or peak between the range of approximately 430 nm and 405 nm. In another example, the biosensor 100 may measure the absorbance spectra curve of oxygenated HB and determine its relative shift or peak between 421 nm and 393 nm.

The biosensor 100 accesses a calibration database that correlates the relative shift in the absorbance spectra of the substance with a concentration level of NO at 1606. The biosensor 100 may thus obtain an NO concentration level using calibration database and the measured relative shift in absorbance spectra of the spectrum at 1608.

Figure 17:
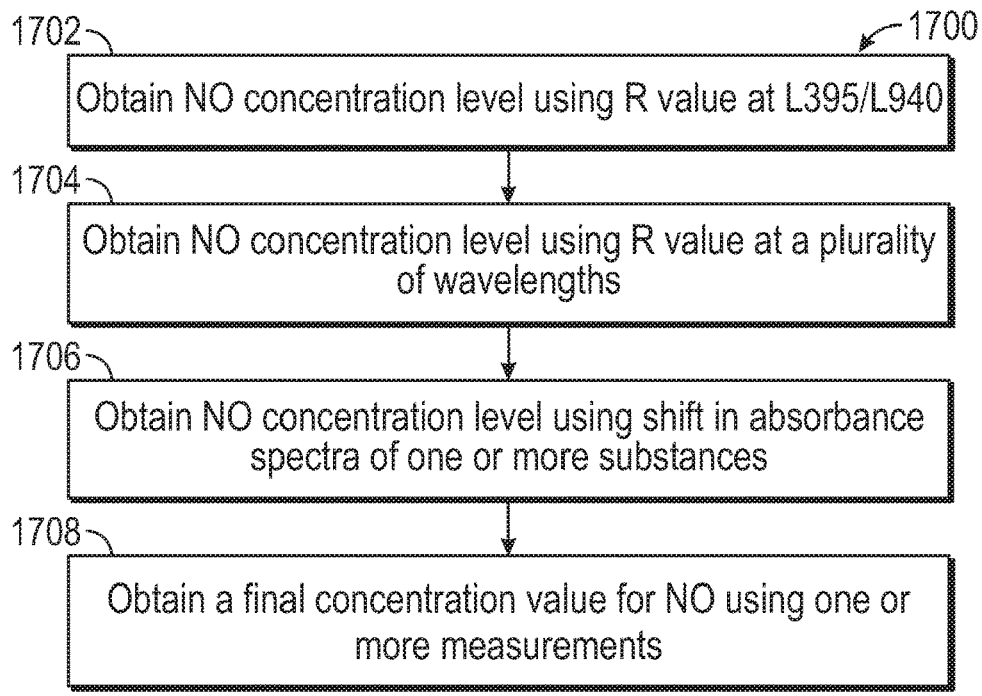
FIG. 17 illustrates a logical flow diagram of an exemplary embodiment of a method for measuring NO concentration levels using one or more measurement techniques.

FIG. 17 illustrates a logical flow diagram of an exemplary embodiment of a method 1700 for measuring NO concentration levels using one or more measurement techniques. In an embodiment, the biosensor 100 is configured to determine a concentration level of NO in vivo using PPG technology and one or more measurement techniques described herein. For example, the biosensor 100 may determine an R value at $L_{390}/L_{940}$ at 1702 and accessing a calibration database that maps the R value to an NO concentration level. In another example, the biosensor may determine NO concentration level using absorption spectrum over a plurality of wavelengths and subtract or compensate for hemoglobin concentrations at 1704. In another example, the biosensor 100 may determine the relative shift in the absorbance spectra for the substance and access a calibration database that correlates the relative shift in the absorbance spectra of the substance with a concentration level of NO at 1706.

The biosensor 100 may use a plurality of these methods to determine a plurality of values for the concentration level of NO at 1708. The biosensor 100 may determine a final concentration value using the plurality of values. For example, the biosensor 100 may average the values, obtain a mean of the values, etc.

Figure 18:
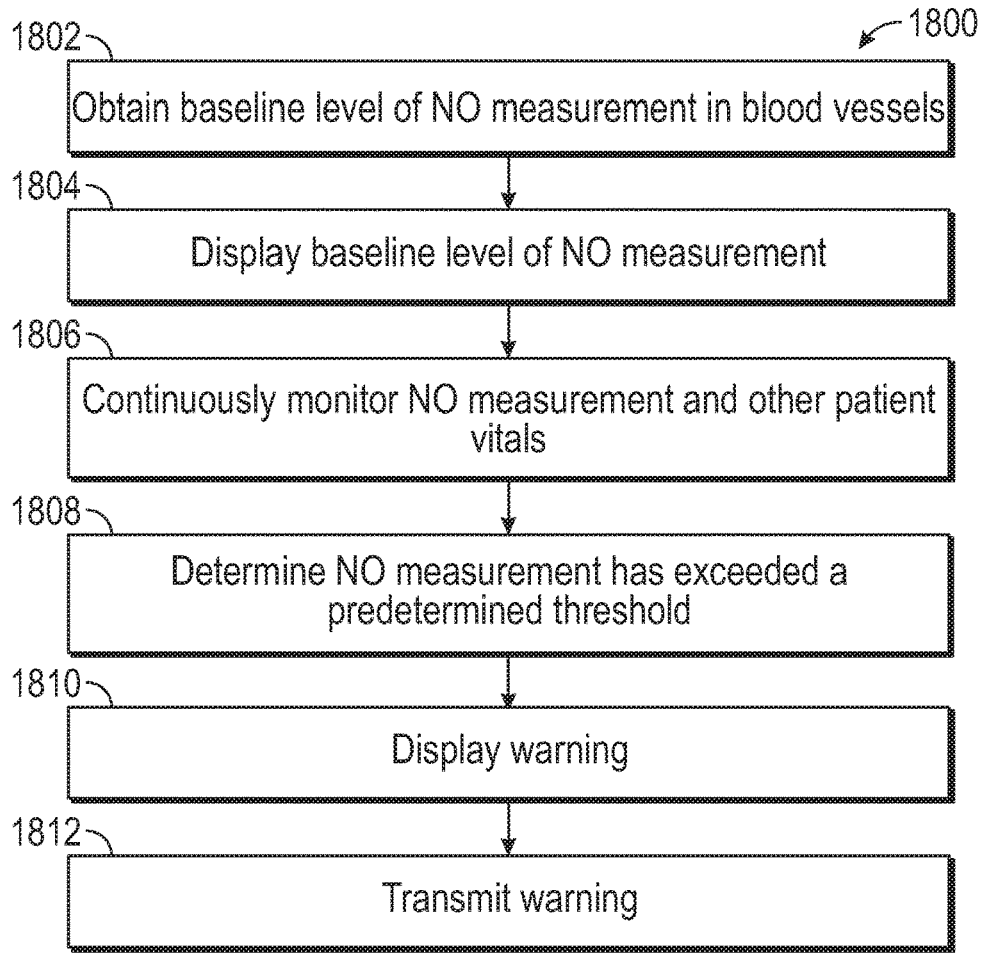
FIG. 18 illustrates a logical flow diagram of an embodiment of a method for monitoring NO measurements in vivo.

FIG. 18 illustrates a logical flow diagram of an embodiment of a method 1800 for monitoring NO measurements in vivo. In 1802, a baseline of an NO measurement in blood vessels is obtained. For example, the NO measurement may be the R value at $L\lambda 1=390$ nm and $L\lambda 2=940$ nm. In another embodiment, the NO measurement may be a SpNO measurement of a concentration level of NO in the blood. In another embodiment, the NO measurement may be obtained using a value of $L_{\lambda 1}=380$ nm-400 nm and $L\lambda 2 \geq 660$ nm.

The biosensor 100 displays the baseline NO measurement in 1804 and then non-invasively and continuously monitors the NO measurement in blood vessels in 1806. For example, the biosensor 100 may obtain the NO measurement at least once per minute or more frequently, such as every 10 seconds or 30 seconds, and continues to display the NO concentration level. The biosensor 100 may average the obtained L values and/or R values over one or more respiratory cycles or over a predetermined time period (such as one minute) to obtain the NO concentration level.

One or more of the NO measurements (Such as $L\lambda 1=390$ nm, R value, NO concentration level) may be compared to predetermined thresholds at 1808. For example, normal ranges of the NO measurement from the baseline measurement are determined. Depending on the comparison, one or more health risks may be determined. For example, diabetic risk or potential carbon monoxide poisoning or septic risk may be determined. The one or more health risks or a general warning of abnormal NO measurements may then be displayed at 1810. In addition, the NO measurements or warnings may be transmitted by the biosensor either wirelessly or over a wired connection over a LAN or WAN to a user device or monitoring station or physician's office or other third party in 1812. For example, the warning may be transmitted to a nursing station, an emergency alert service or physician's office to provide emergency services to the patient.

Embodiment—Adjustments in Response to Positioning of the Biosensor

Figure 19:
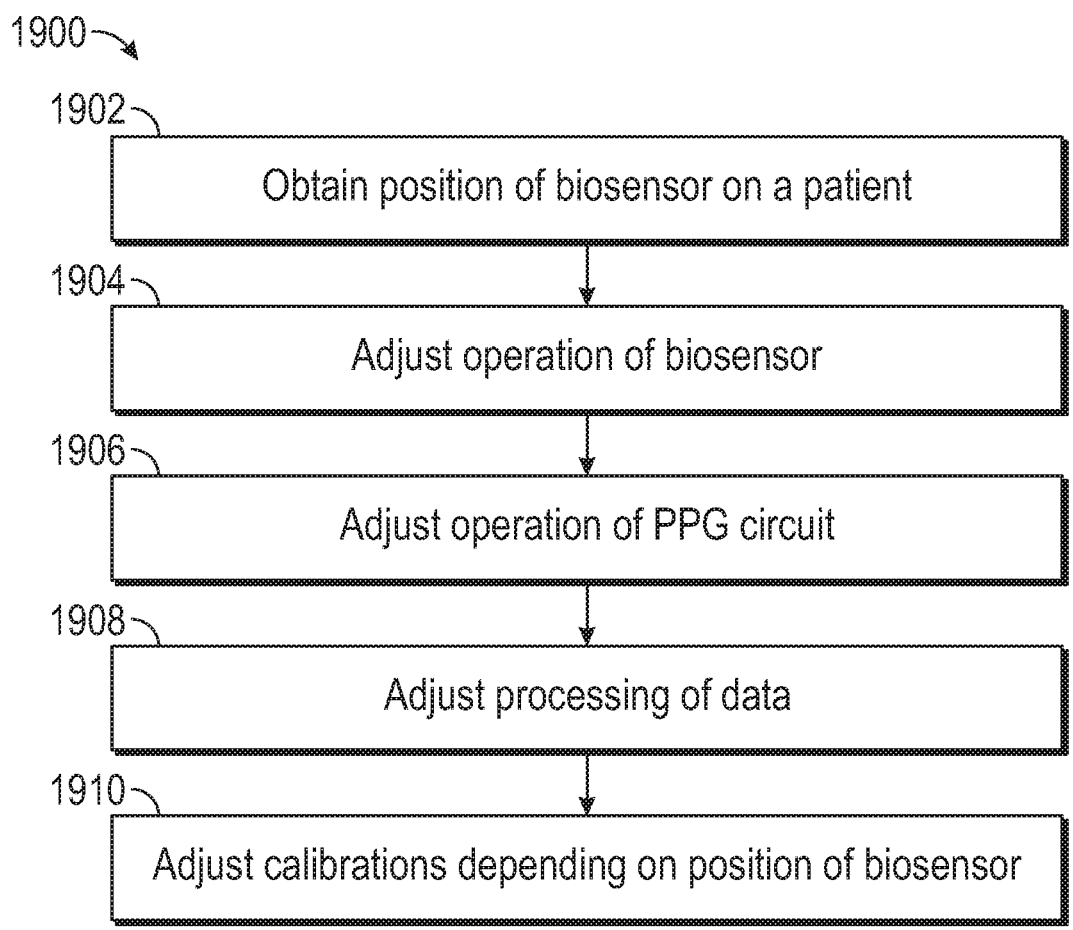
FIG. 19 illustrates a logical flow diagram of an embodiment of a method for adjusting operation of the biosensor in response to a position of the biosensor.

FIG. 19 illustrates a logical flow diagram of an embodiment of a method 1900 for adjusting operation of the biosensor 100 in response to a position of the biosensor 100. The biosensor 100 may be positioned over different parts of a patient that exhibit different underlying tissue characteristics. For example, the biosensor 100 may be positioned on or attached to various areas of the body, e.g. a hand, a wrist, an arm, forehead, chest, abdominal area, ear lobe, fingertip or other area of the skin or body or living tissue. The characteristics of underlying tissue vary depending on the area of the body, e.g. the underlying tissue of an abdominal area has different characteristics than the underlying tissue at a wrist. The operation of the biosensor 100 may need to be adjusted in response to its positioning due to such varying characteristics of the underlying tissue.

The biosensor 100 is configured to obtain position information on a patient at 1902. The position information may be input from a user interface. In another aspect, the biosensor 100 may determine its own positioning. For example, the PPG circuit 110 may be configured to detect characteristics of underlying tissue. The biosensor 100 then correlates the detected characteristics of the underlying tissue with known or predetermined characteristics of underlying tissue (e.g. measured from an abdominal area, wrist, forearm, leg, etc.) to determine its positioning. Information of amount and types of movement from an activity monitoring circuit implemented within the biosensor 100 may also be used in the determination of position.

In response to the determined position and/or detected characteristics of the underlying tissue, the operation of the biosensor 100 is adjusted at 1904. For example, the biosensor 100 may adjust operation of the PPG circuit 110 at 1906. The article, "Optical Properties of Biological Tissues: A Review," by Steven L. Jacques, Phys. Med. Biol. 58 (2013), which is hereby incorporated by reference herein, describes wavelength-dependent behavior of scattering and absorption of different tissues. The PPG circuit 110 may adjust a power of the LEDs or a frequency or wavelength of the LEDs based on the underlying tissue. The biosensor 100 may adjust processing of the data at 1908. For example, an absorption coefficient may be adjusted when determining a concentration level of a substance based on Beer-Lambert principles due to the characteristics of the underlying tissue.

In addition, the calibrations utilized by the biosensor 100 may vary depending on the positioning of the biosensor at 1908. For example, the calibration database may include different table or other correlations between R values and NO concentration level depending on position of the biosensor. Due to the different density of tissue and vessels, the R value obtained from measurements over an abdominal area may be different than measurements over a wrist or forehead. The calibration database may thus include different correlations of the R value and NO concentration level depending on the underlying tissue. Other adjustments may also be implemented by the biosensor 100 depending on predetermined or measured characteristics of the underlying tissue.

The biosensor 100 is thus configured to obtain position information and perform adjustments to its operation in response to the position information.

Embodiment—EMR Network

Figure 20:
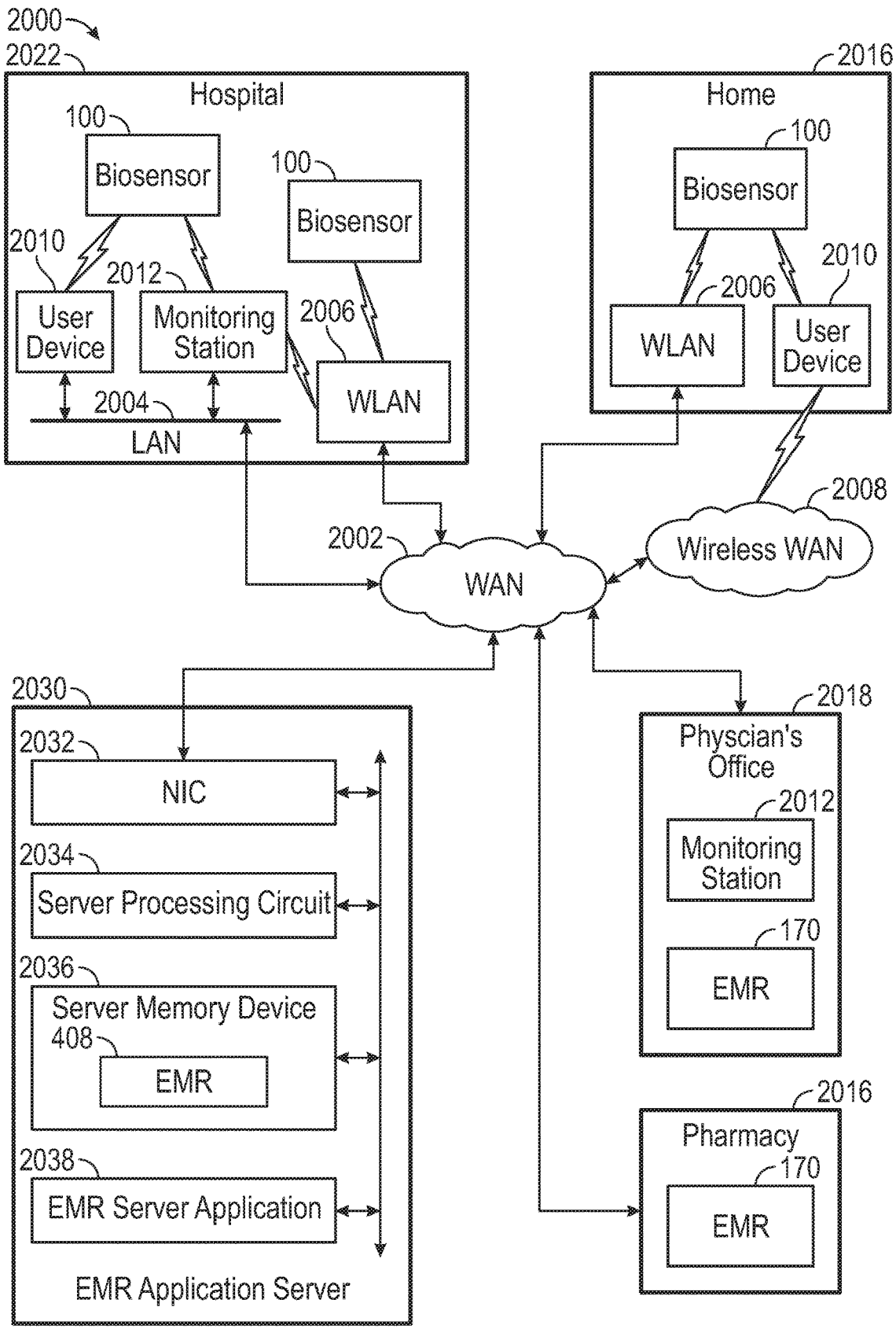
FIG. 20 illustrates a schematic block diagram of an embodiment of an exemplary network in which the the biosensor described herein may operate.

FIG. 20 illustrates a schematic block diagram of an embodiment of an exemplary network 2000 in which the the biosensor 100 described herein may operate. The exemplary network 2000 may include a combination of one or more networks that are communicatively coupled, e.g., such as a wide area network (WAN) 2002, a wired local area network (LAN) 2004, a wireless local area network (WLAN) 2006, or a wireless wide area network (WAN) 2008. The wireless WAN 1228 may include, for example, a 3G or 4G cellular network, a GSM network, a WIMAX network, an EDGE network, a GERAN network, etc. or a satellite network or a combination thereof. The WAN 1222 includes the Internet, service provider network, other type of WAN, or a combination of one or more thereof. The LAN 2004 and the WLANs 2006 may operate inside a home 2016 or enterprise environment, such as a physician's office 2018, pharmacy 2020 or hospital 2022 or other caregiver.

The biosensor 100 may communicate to one or more user devices 2010, such as a smart phone, laptop, desktop, smart tablet, smart watch, or any other processing device. In one aspect, the user device 2010 or biosensor 100 may communicate the patient's vitals to a local or remote monitoring station 2012 of a caregiver or physician.

One or more biosensors 100 are communicatively coupled to an EMR application server 2030 through one or more user devices 2010 and/or networks in the EMR network 2000. The EMR server 2030 includes a network interface card (NIC) 2032, a server processing circuit 2034, a server memory device 2036 and EMR server application 2038. The network interface circuit (NIC) 2032 includes an interface for wireless and/or wired network communications with one or more of the exemplary networks in the EMR network 2000. The network interface circuit 2032 may also include authentication capability that provides authentication prior to allowing access to some or all of the resources of the EMR application server 2030. The network interface circuit 2032 may also include firewall, gateway and proxy server functions.

The EMR application server 2030 also includes a server processing circuit 2034 and a memory device 2036. For example, the memory device 2036 is a non-transitory, processor readable medium that stores instructions which when executed by the server processing circuit 2034, causes the server processing circuit 2034 to perform one or more functions described herein. In an embodiment, the memory device 2036 stores a patient EMR 408 that includes biosensor data and historical data of a patient associated with the patient ID 406.

The EMR application server 2030 includes an EMR server application 2038. The EMR server application 2038 is operable to communicate with the biosensors 100 and/or user devices 2010 and monitoring stations 2012. The EMR server application 2038 may be a web-based application supported by the EMR application server 2030. For example, the EMR application server 2030 may be a web server and support the EMR server application 2038 via a website. In another embodiment, the EMR server application 2038 is a stand-alone application that is downloaded to the user devices 2010 by the EMR application server 2030 and is operable on the user devices 2010 without access to the EMR application server 2030 or only needs to accesses the EMR application server 2030 for additional information and updates.

In use, the biosensors 100 may communicate patient's biosensor data (such as NO concentration level, heart rate, temperature, respiratory cycle, etc.) to the EMR application server 2030. A biosensor 100 may be programmed with a patient identification 406 that is associated with a patient's EMR 408. The biosensor 100 measures the patient's vitals, such as heart rate, pulse, blood oxygen levels, NO levels, etc. and may also communicate information to a drug delivery system to administer medications to the patient. The biosensor 100 is configured to transmit the patient vitals to the EMR application server 2030. The EMR server application 2038 updates an EMR 408 associated with the patient identification 406 with the patient vitals.

The EMR application server 2030 may also be operable to communicate with a physician's office 2018 or pharmacy 2020 or other third party health care provider over the EMR network 2000 to provide biosensor data and receive instructions on dosages of medication. For example, the EMR server application 2038 may transmit NO level information, heart rate information or pulse rate information or medication dosages or blood concentration levels of one or more relevant substances to a physician's office 2018. The EMR server application 2038 may also be configured to provide medical alerts to notify a user, physician or other caregiver when vitals are critical or reach a certain predetermined threshold.

The EMR server application 2030 may also receive instructions from a physician's office 2018, pharmacy 2020 or hospital 2022 or other caregiver regarding a prescription or administration of a dosage of medication. The EMR server application 2038 may then transmit the instructions to the biosensor 100. The instructions may include a dosage amount, rate of administration or frequency of dosages of a medication. The biosensor 100 may then control a drug delivery system to administer the medication automatically as per the transmitted instructions.

Embodiment—Interoperability of Biosensors and Other Devices

Figure 21:
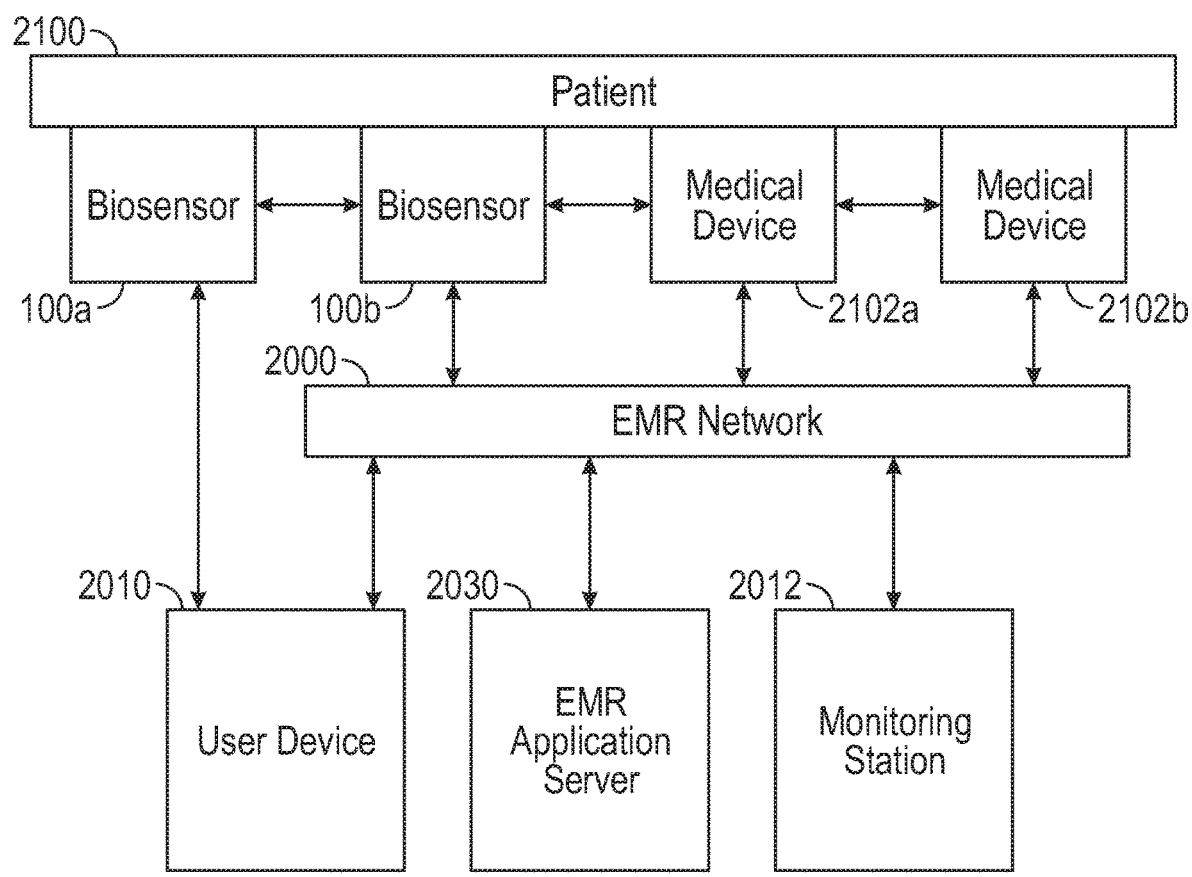
FIG. 21 illustrates a schematic block diagram of an embodiment of a network illustrating interoperability of a plurality of biosensors.

FIG. 21 illustrates a schematic block diagram of an embodiment of a network illustrating interoperability of a plurality of biosensors 100. A plurality of biosensors 100 may interface with a patient and communicate with one or more of the other biosensors 100. The biosensors 100 may communicate directly or communicate indirectly through a WLAN or other type of network as illustrated in the EMR network 2000 of FIG. 20. For example, a first biosensor 100a may include a PPG circuit 110 configured to detect a NO concentration level. For better detection, the biosensor 100a is positioned on a wrist. A second biosensor 100b may be positioned on a chest area of the patient 2100. In use, the first biosensor 100a continuously monitors NO concentration levels and then communicates either directly or indirectly the detected levels to the user device 2010 or network 2000 or second biosensor 100b or to one or more medical devices 2102a-b. For example, the first biosensor 100a may transmit NO concentration levels to a medical device 2102a that delivers medicine to the patient 2100. The second biosensor 100b may detect heart rate or respiratory cycle and communicates either directly or indirectly the detected levels to the user device 2010 or network 2000 or first biosensor 100a or medical devices 2102a-b.

In another example, a plurality of biosensors 100, such as the first biosensor 100a and the second biosensor 100b, may be positioned on a patient to monitor an ECG of the patient. The biosensors 100 may communicate the ECG measurements directly or indirectly to each other to generate an electrocardiogram. The electrocardiogram is transmitted to an EMR application server 2030 or monitoring station 2012 or to a user device 2010. Based on the electrocardiogram, a doctor or user may provide instructions to one of the medical devices 2102a-b. For example, one of the medical devices 2102a-b may include a pacemaker.

Figure 22A:
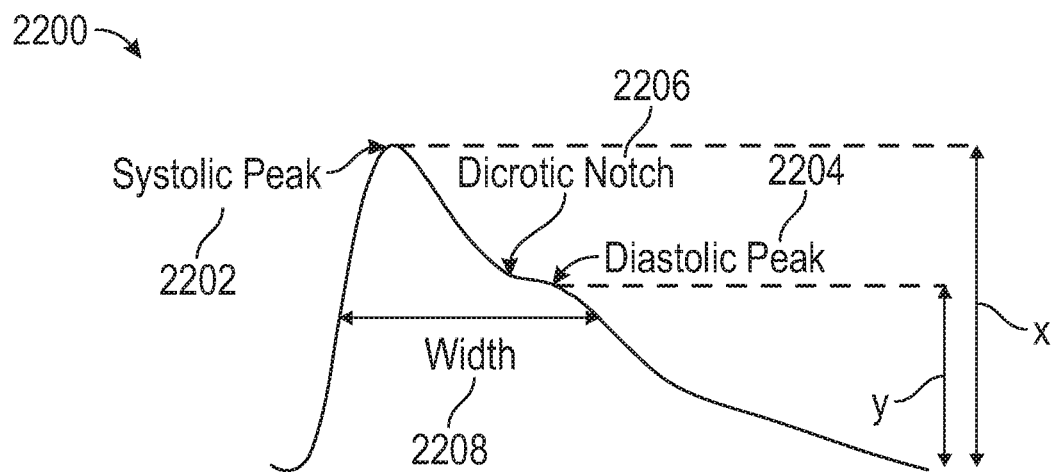
FIG. 22A and FIG. 22B illustrate an embodiment of a typical waveform of a PPG signal reflecting an arterial pressure waveform.
Figure 22B:
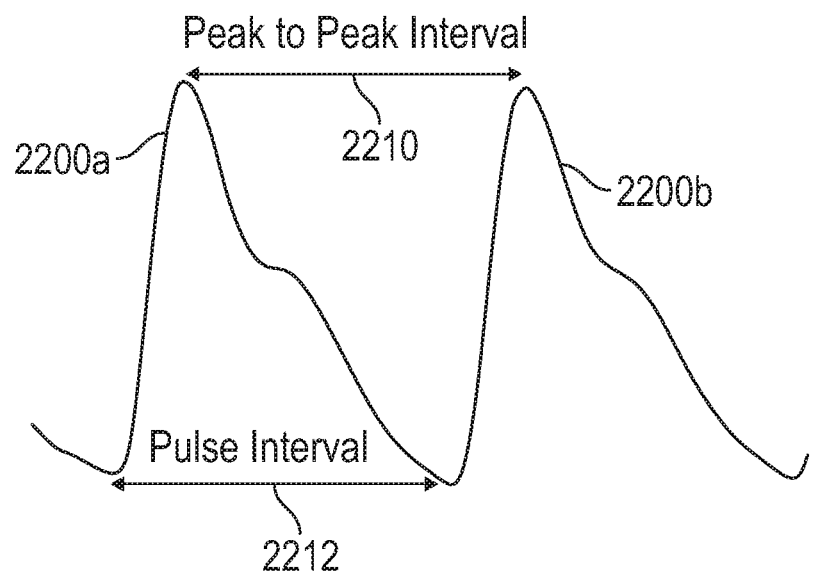

FIG. 22A and FIG. 22B illustrate an embodiment of a typical waveform of a PPG signal 2200 reflecting an arterial pressure waveform. In FIG. 22A, the PPG signal 2200 includes characteristic parameters such as systolic peak 2202 with an amplitude x and a diastolic peak 2204 of amplitude y. A width 2208 of the pulse is measured at a half the amplitude x. A dicrotic notch 2206 is also typically exhibited. The dicrotic notch 2206 is a secondary upstroke in the descending part of the arterial pressure pulse curve corresponding to the transient increase in aortic pressure upon closure of the aortic valve. It may be used as a marker for the end of the_systole period of the cardiac cycle. FIG. 22B illustrates a first PPG signal 2200a and a second PPG signal 2200b. The distance between the systolic peak of the first PPG signal 2200a and the second PPG signal 2200b is known as the peak to peak interval 2210. A pulse interval 2212 is the distance between the beginning of one pulse to the beginning of the next pulse.

Embodiment—Clinical Data

Clinical data obtained using an embodiment of the biosensor 100 is now described herein. The biosensor 100 was used to monitor concentration levels or indicators of Nitric Oxide in the blood flow of a patient in clinical trials over a measurement time period.

Figure 23:
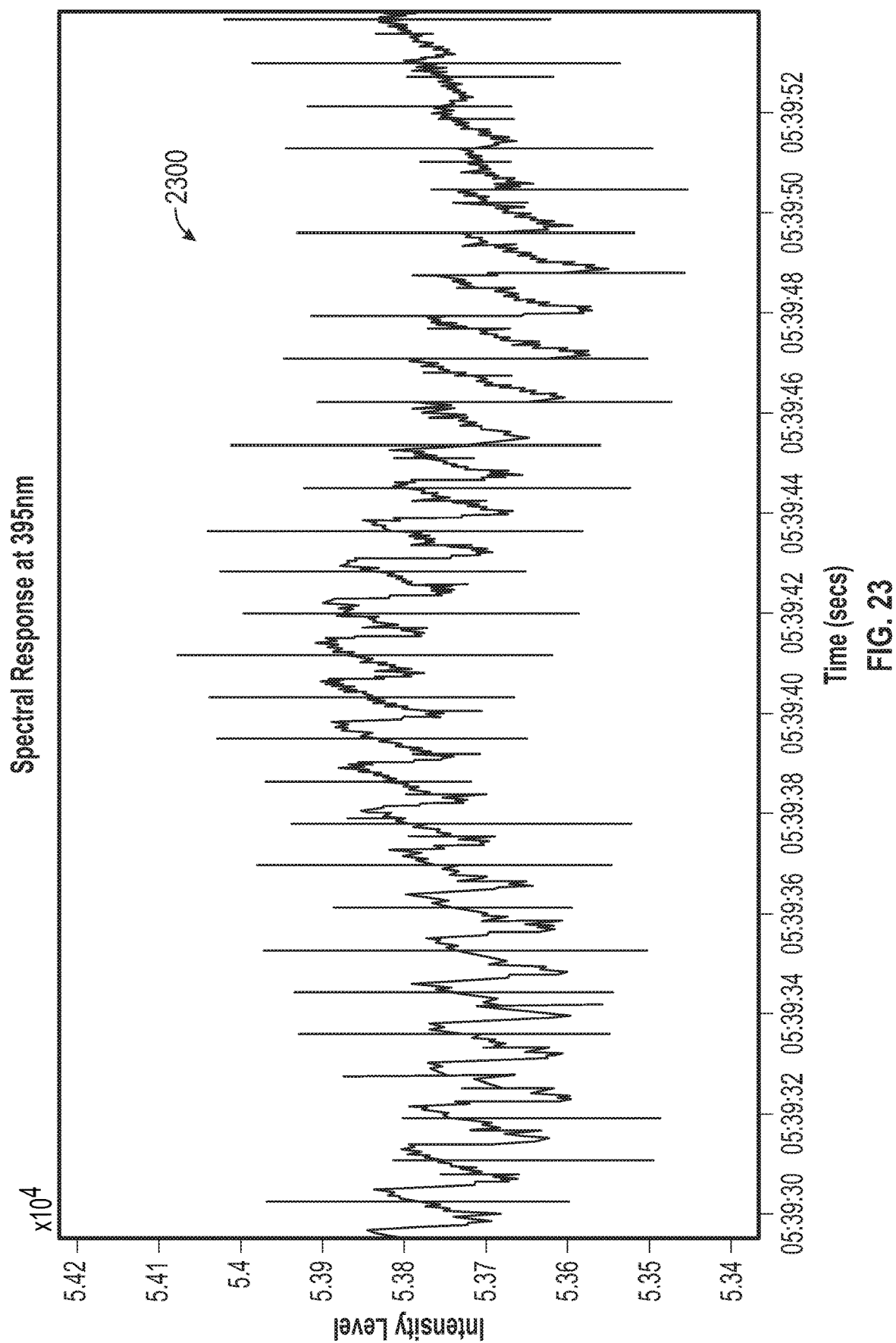
FIG. 23 illustrates a schematic drawing of an exemplary embodiment of results of a spectral response obtained using an embodiment of the biosensor from a first patient.

FIG. 23 illustrates a schematic drawing of an exemplary embodiment of results of a spectral response 2300 obtained using an embodiment of the biosensor 100 from a first patient. The spectral response 2300 was obtained at a wavelength of around 395 nm and is illustrated for a time period of about 40 seconds.

Figure 24:
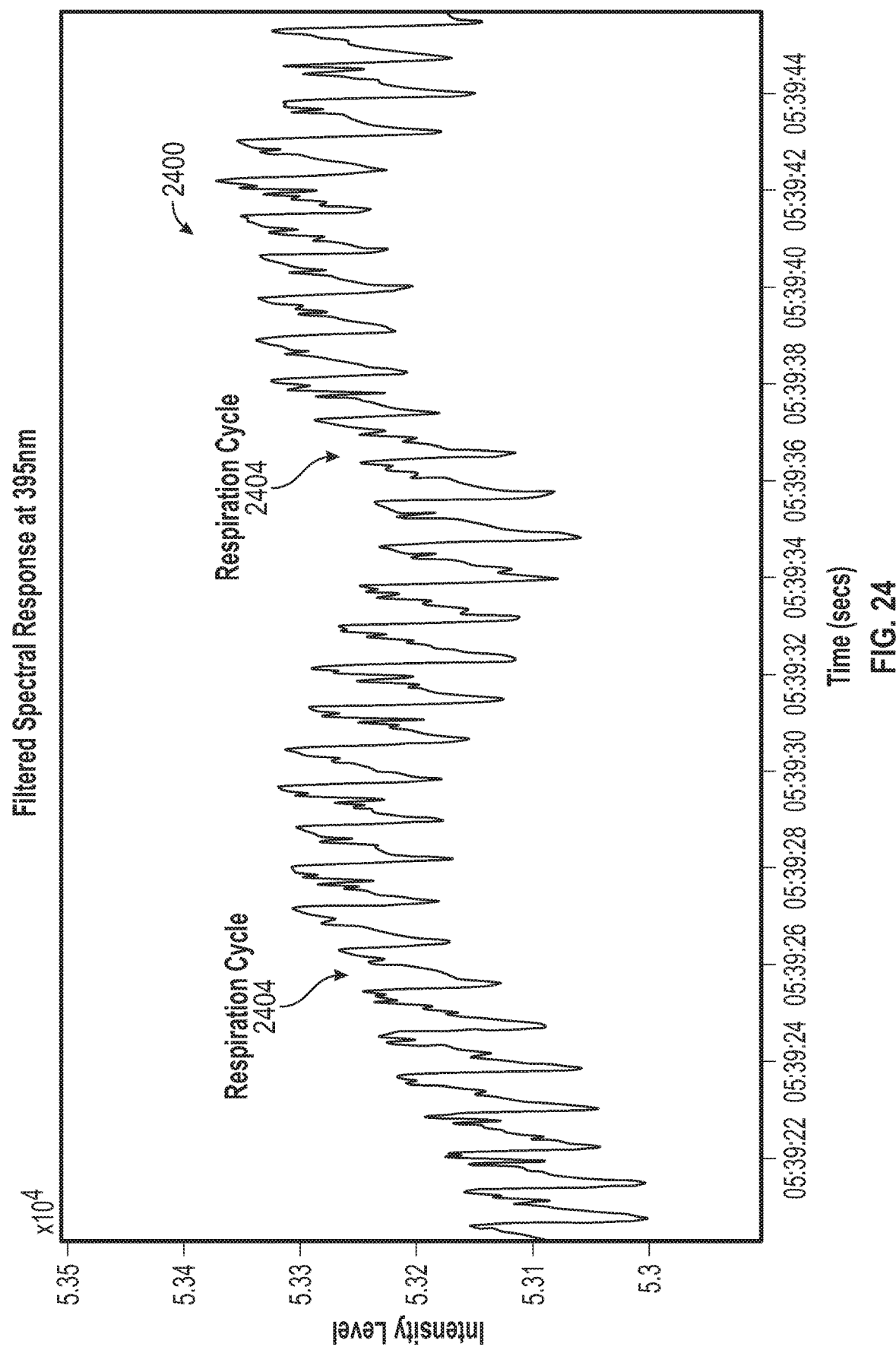
FIG. 24 illustrates a schematic drawing of an exemplary embodiment of results of a filtered spectral response.

FIG. 24 illustrates a schematic drawing of an exemplary embodiment of results of a filtered spectral response 2400. The spectral response 2300 in FIG. 23 is filtered using digital signal processing techniques by the biosensor 100 to eliminate noise and background interference to obtain the filtered spectral response 2400. A first respiration cycle 2402 and a second respiration cycle 2404 may be seen in the slow fluctuation of the filtered spectral response 2400. Due to this fluctuation over respiratory cycles, the obtained L values are averaged over a plurality of respiratory cycles or over a predetermined time period such as 1-2 minutes.

Figure 25:
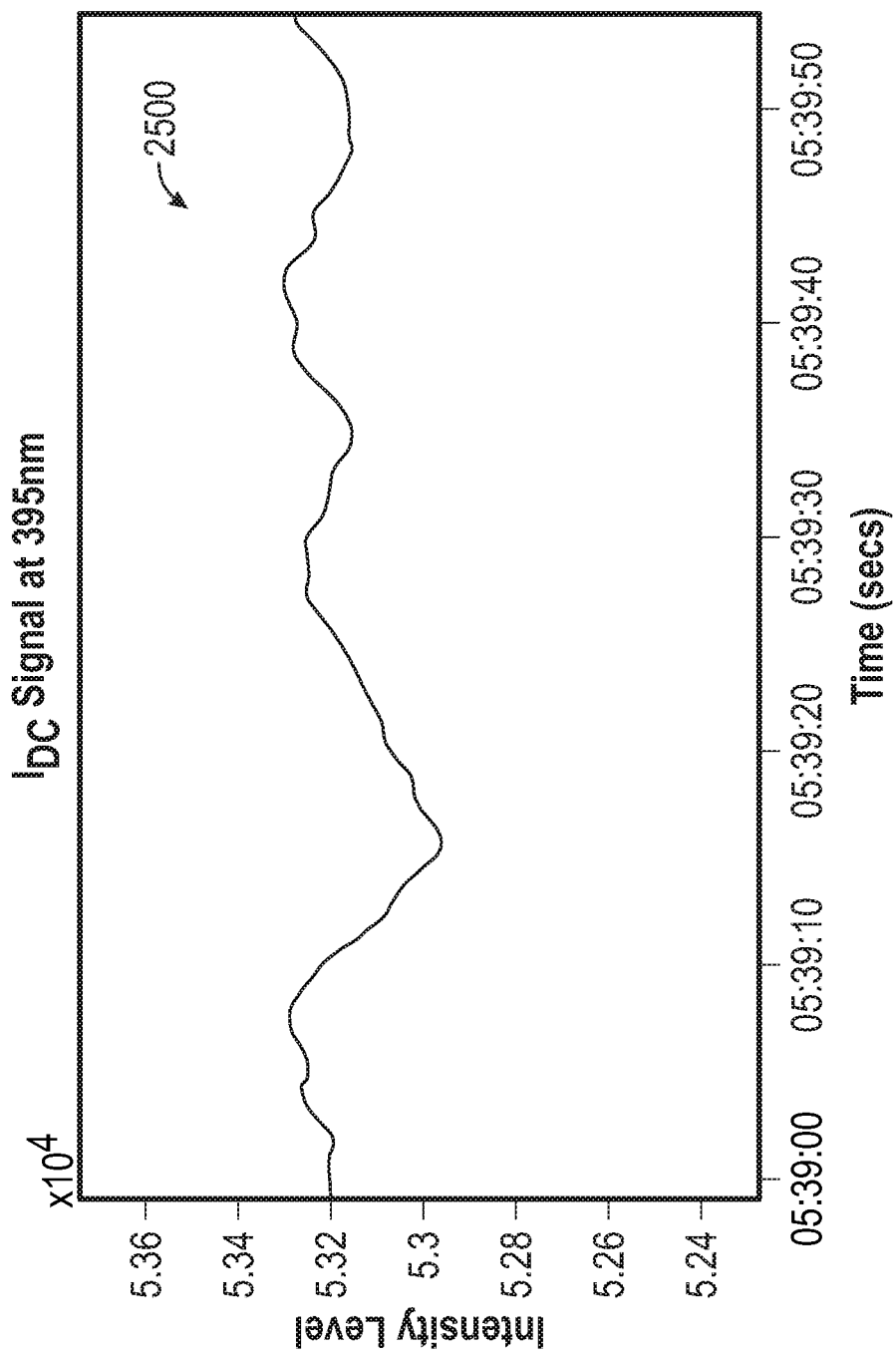
FIG. 25 illustrates a schematic drawing of an exemplary embodiment of results of an $I_{DC}$ signal generated using the filtered spectral response.

FIG. 25 illustrates a schematic drawing of an exemplary embodiment of results of an $I_{DC}$ signal 2500 generated using the filtered spectral response 2400. A low pass filter (such as a 5 Hz low pass filter) is applied to the filtered spectral response 2400 ($I_{AC+DC}$) to obtain the DC component of the spectral response $I_{DC}$.

Figure 26:
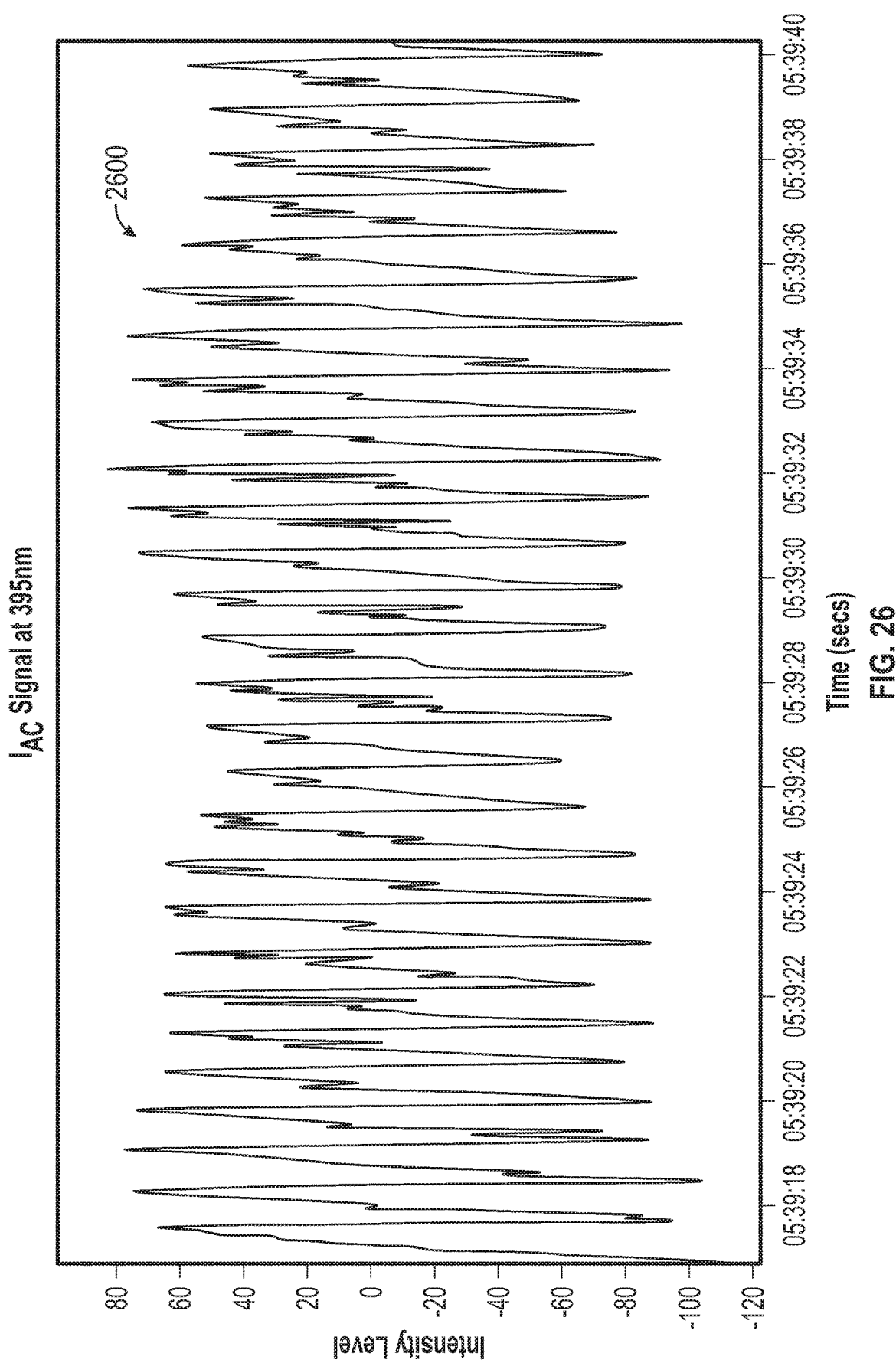
FIG. 26 illustrates a schematic drawing of an exemplary embodiment of results of an $I_{AC}$ signal.

FIG. 26 illustrates a schematic drawing of an exemplary embodiment of results of an $I_{AC}$ signal 2600. The $I_{AC}$ signal 2600 is generated from the the filtered spectral response 2400 and the signal $I_{DC}$ 2500. The AC component is the fluctuation due to the pulsatile expansion of the arteriolar bed as the volume of arterial blood increases. In order to measure the AC fluctuation, measurements are taken at different times and a peak detection algorithm is used to determine the diastolic point and the systolic point of the filtered spectral response. Rather than using a low pass filter, fast Fourier transform or other functions may also be used to isolate the DC component of the filtered spectral response to obtain $I_{AC}$.

Figure 27:
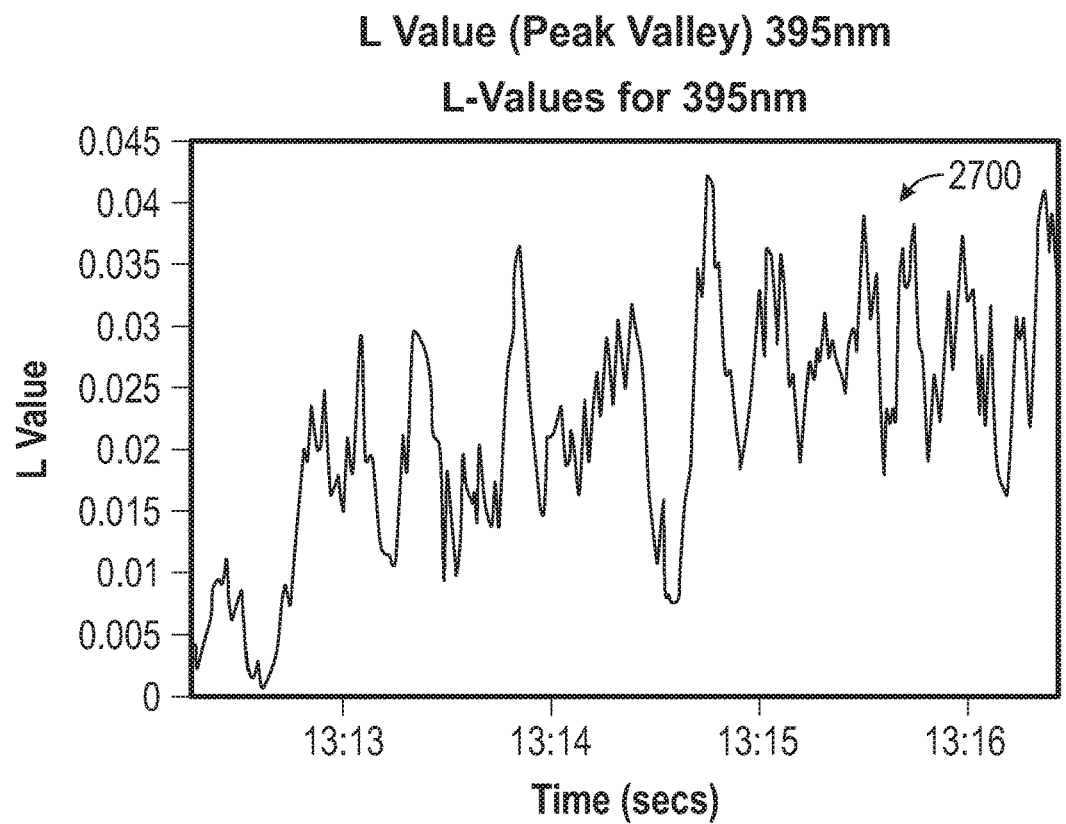
FIG. 27 illustrates a schematic drawing of an exemplary embodiment of results of L values obtained over a time period.

FIG. 27 illustrates a schematic drawing of an exemplary embodiment of results of L values 2700 obtained over a time period. The filtered spectral response $I_{AC+DC}$ 2400 and $I_{DC}$ signal 2500 components are used to compute L values 2700. A logarithmic function is applied to the ratio of the signal IAC+DC and the signal IDC:

$$L_{395} = \mathrm{Log}10\left(\frac{IAC + DC}{IDC}\right)$$

The L values 2700 fluctuate between 0.005 and 0.045 over the four second time period illustrated in the graph.

Figure 28:
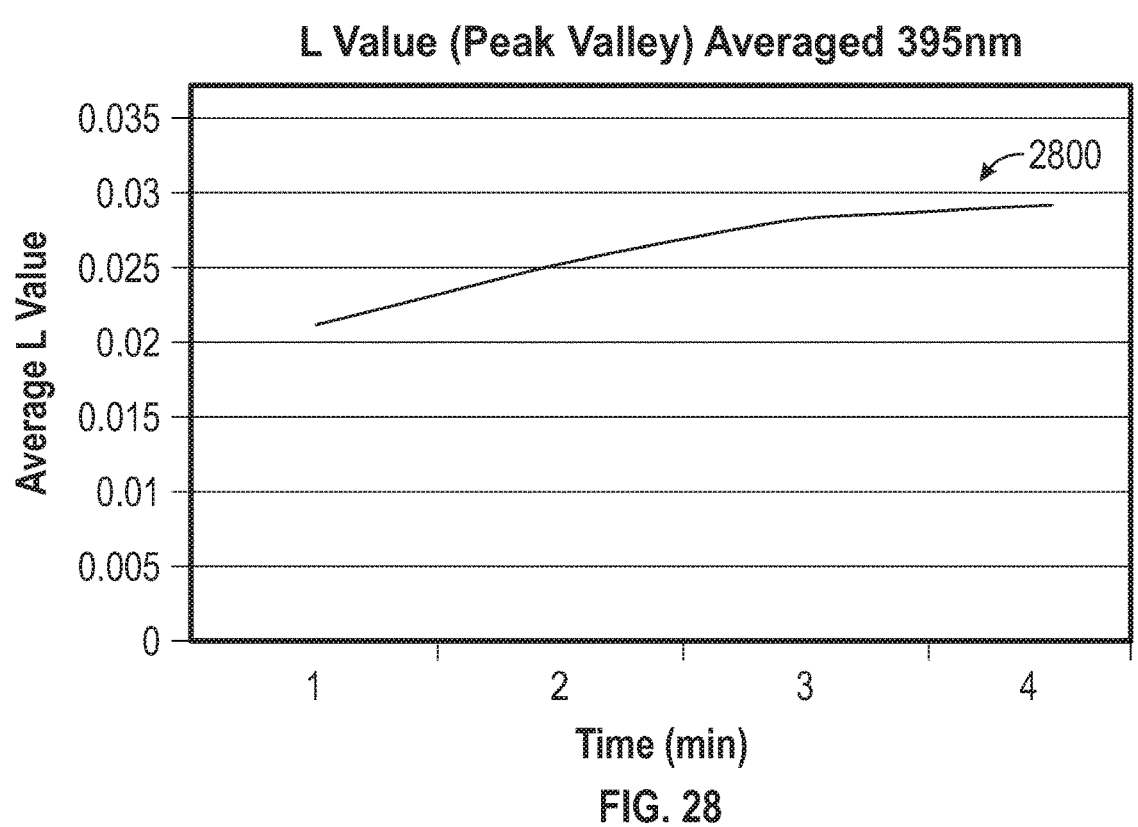
FIG. 28 illustrates a schematic drawing of an exemplary embodiment of results of averaged L values.

FIG. 28 illustrates a schematic drawing of an exemplary embodiment of results of averaged L values 2800. The L values are affected by the respiratory cycle as previously described. Thus, the L values 2700 shown in FIG. 27 are averaged over two or more respiratory cycles. Alternatively, the L values 2700 may be averaged over a predetermined time period (such as a 1-2 minute time period). As shown in FIG. 28, the averaged L values 2800 fluctuate between 0.2 and 0.3 over a three minute time period.

Figure 29:
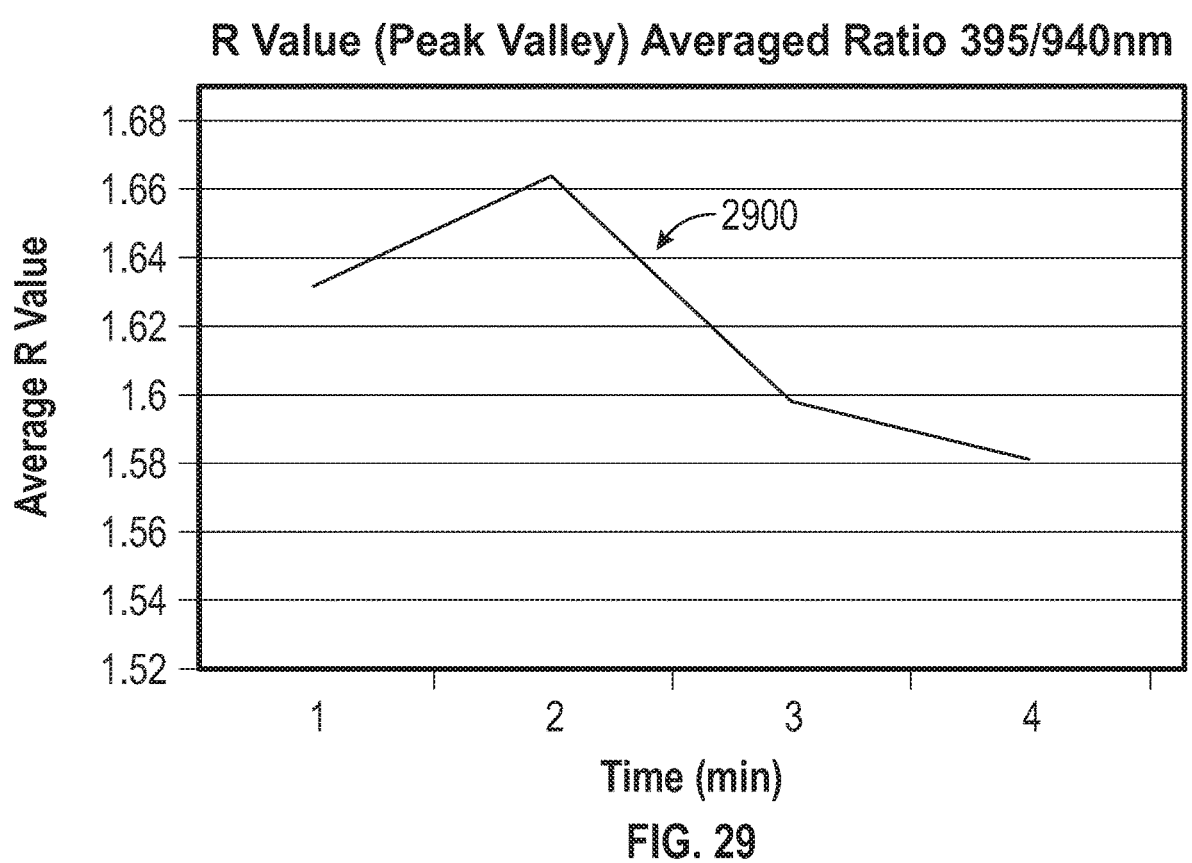
FIG. 29 illustrates a schematic drawing of an exemplary embodiment of results of averaged R values.

FIG. 29 illustrates a schematic drawing of an exemplary embodiment of results of averaged R values 2900. A ratio R of the $L_{395\ nm}$ values and $L_{940\ nm}$ are obtained from:

$$\text{Ratio } R = \frac{L395}{L940}$$

The averaged R values 2900 may be obtained from averaging the Ratio R over a predetermined time period or may be calculated from the averaged L values. As shown in FIG. 29, the averaged R values 2900 fluctuate between 1.68 and 1.58 over a three minute time period.

Figure 30:
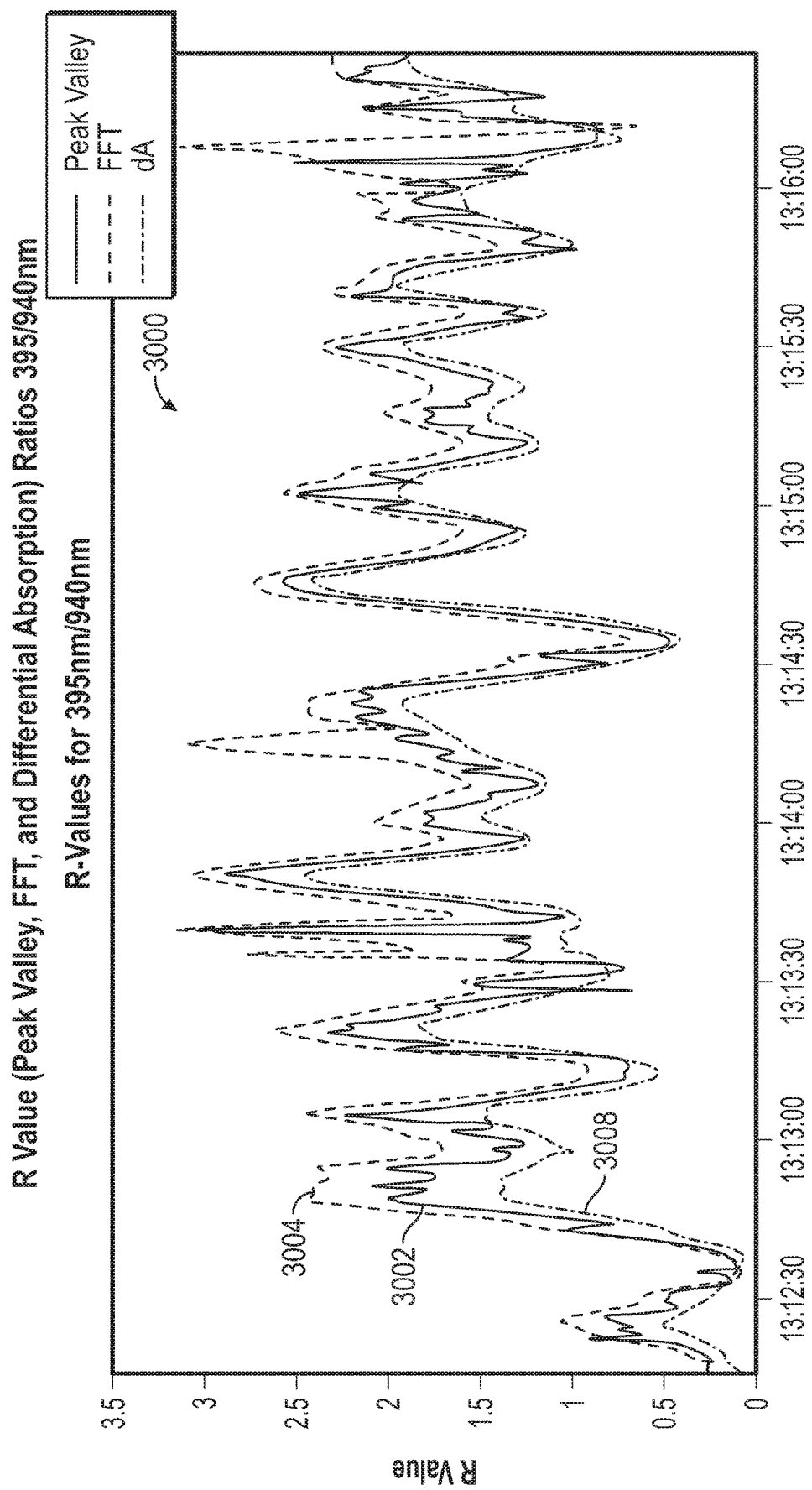
FIG. 30 illustrates a schematic drawing of an exemplary embodiment of results of R values determined using a plurality of methods.

FIG. 30 illustrates a schematic drawing of an exemplary embodiment of results of R values 3000 determined using a plurality of methods. The R values 3000 corresponding to the wavelengths of 395 nm/940 nm is determined using three methods. The R Peak Valley curve 3002 is determined using the Ratio $$R = \frac{L395}{L940}$$

as described hereinabove. The R FFT curve 3004 is determined using FFT techniques. The R differential absorption curve 3008 is determined using the shift in absorbance spectra as described hereinabove with respect to FIGS. 14-16. As seen in FIG. 30, the determination of the R values using the three methods provides similar results, especially when averaged over a period of time. A mean or average of the R values 3002, 3004 and 3008 may be calculated to obtain a final R value or one of the methods may be preferred depending on the positioning of the biosensor or underlying tissue characteristics.

Figure 31:
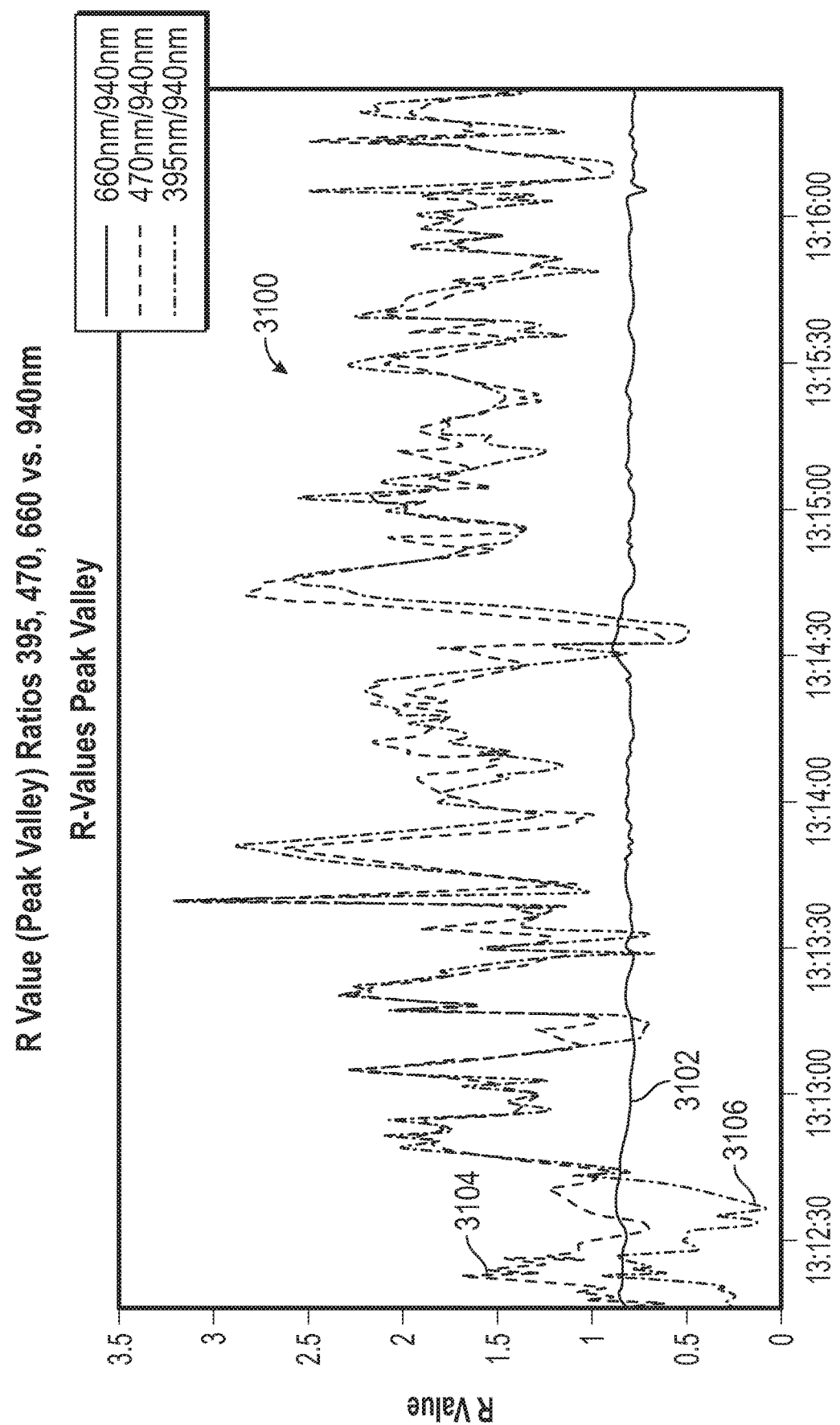
FIG. 31 illustrates a schematic drawing of an exemplary embodiment of results of R values for a plurality of wavelength ratios.

FIG. 31 illustrates a schematic drawing of an exemplary embodiment of results of R values 3100 for a plurality of wavelength ratios. The R values for 395 nm/940 nm 3106, the R values for 470 nm/940 nm 3104 and the R values for 660 nm/940 nm 3106 are shown over a time period of about 4 seconds.

Figure 32:
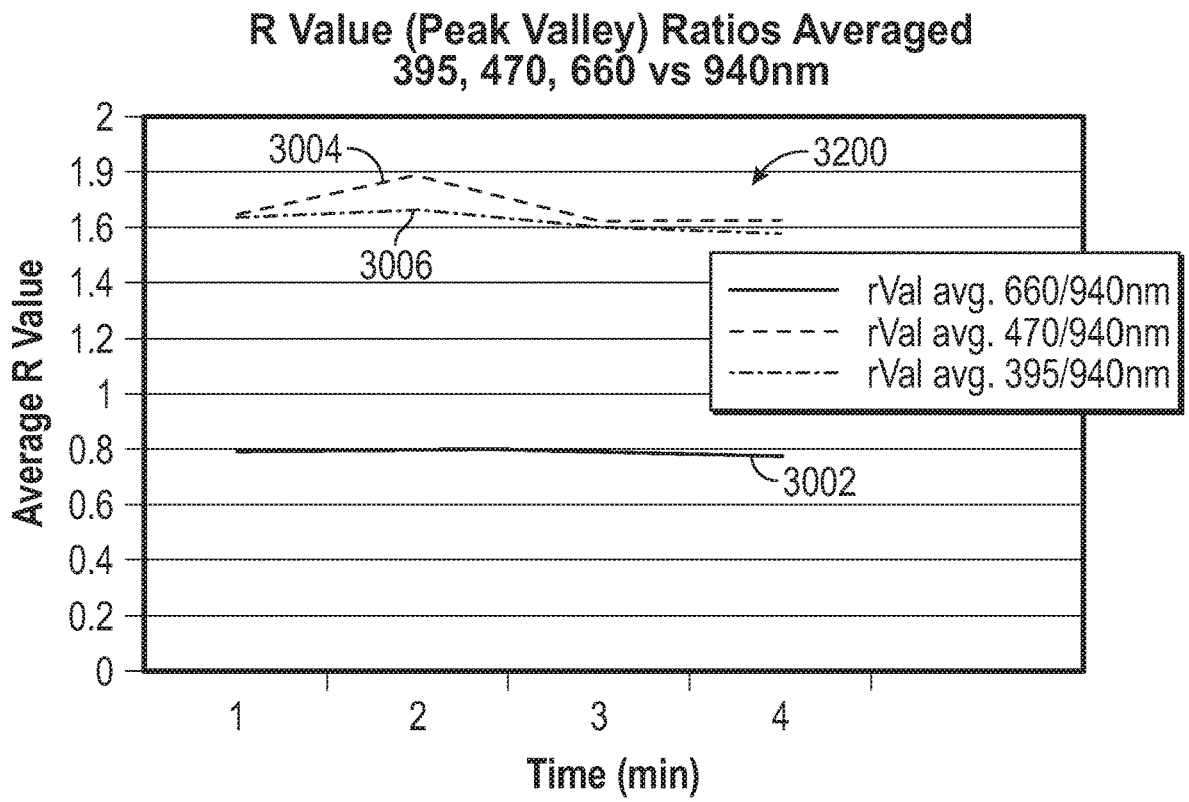
FIG. 32 illustrates a schematic drawing of an exemplary embodiment of results of averaged R values for a plurality of wavelength ratios.

FIG. 32 illustrates a schematic drawing of an exemplary embodiment of results of averaged R values 3200 for a plurality of wavelength ratios. The averaged R values for 395 nm/940 nm 3206, the averaged R values for 470 nm/940 nm 3204 and the averaged R values for 660 nm/940 nm 3206 are shown over a time period of about 4 minutes.

FIG. 33 illustrates a schematic drawing of an exemplary embodiment of a calibration curve 3300 for correlating oxygen saturation levels ($SpO_2$) with R values. For example, the R values may be obtained for $L_{660\ nm}/L_{940\ nm}$. The calibration curve 3300 may be included as part of the calibration database for the biosensor 100. In an embodiment, the biosensor 100 may use the 660 nm wavelength to determine SpO2 levels, e.g. rather than IR wavelength range.

From the clinical trials, the $L_{390}$ values are measuring NO levels in the arterial blood flow. The R value for $L_{390}/L_{940\ nm}$ may thus be used to provide NO concentration levels in the pulsating arterial blood flow. From the clinical trials, it seems that the NO levels are reflected in the R values obtained from $L_{390\ nm}/L_{940\ nm}$. The NO concentration level may be obtained from the R values and a calibration database that correlates the R value with known concentration level of NO for the patient or for a large general population.

In other embodiments, rather than $L_{\lambda 1}=390$ nm, the L value may be measured at wavelengths in a range around 390 nm such as from 400 nm to 380 nm, e.g., as seen in the graphs wherein $L_{\lambda 1}=395$ nm is used to obtain a concentration level of NO. In addition, $L_{\lambda 2}$ may be obtained at any wavelength at approximately 660 nm or above. Thus, R obtained at approximately $L\lambda 1=380$ nm-400 nm and $L\lambda 2 \geq 660$ nm may also be used to determine concentration levels of NO.

Figure 34A:
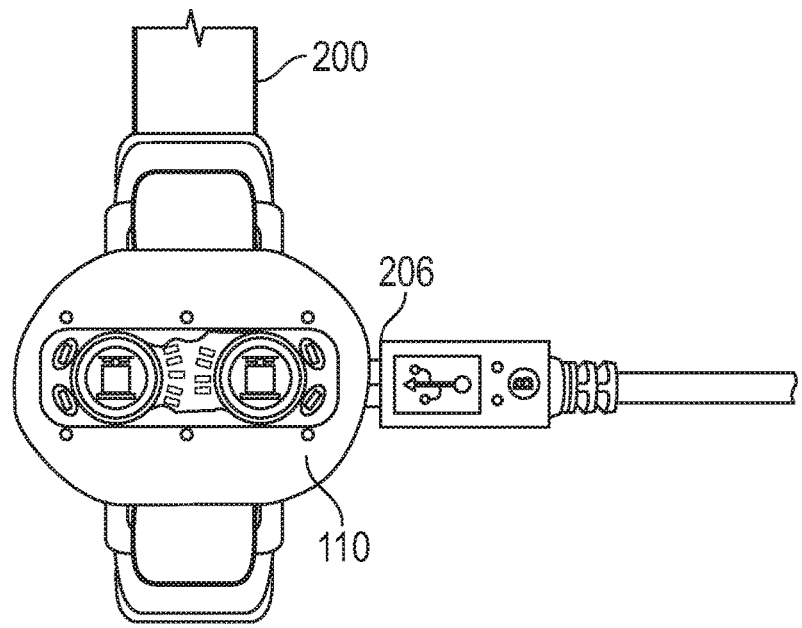
FIG. 34A illustrates a perspective view of an exemplary embodiment of a biosensor with a PPG circuit.

FIG. 34A illustrates a perspective view of an exemplary embodiment of a biosensor 100 with PPG circuit 110. In this embodiment, the biosensor 100 is implemented with the adjustable band 200. The adjustable band 200 may be configured to fit around a wrist, arm, leg, ankle, etc. A USB or other port 206 may be implemented to transmit data to and from the biosensor 100. The biosensor 100 may also include a wireless transceiver.

Figure 34B:
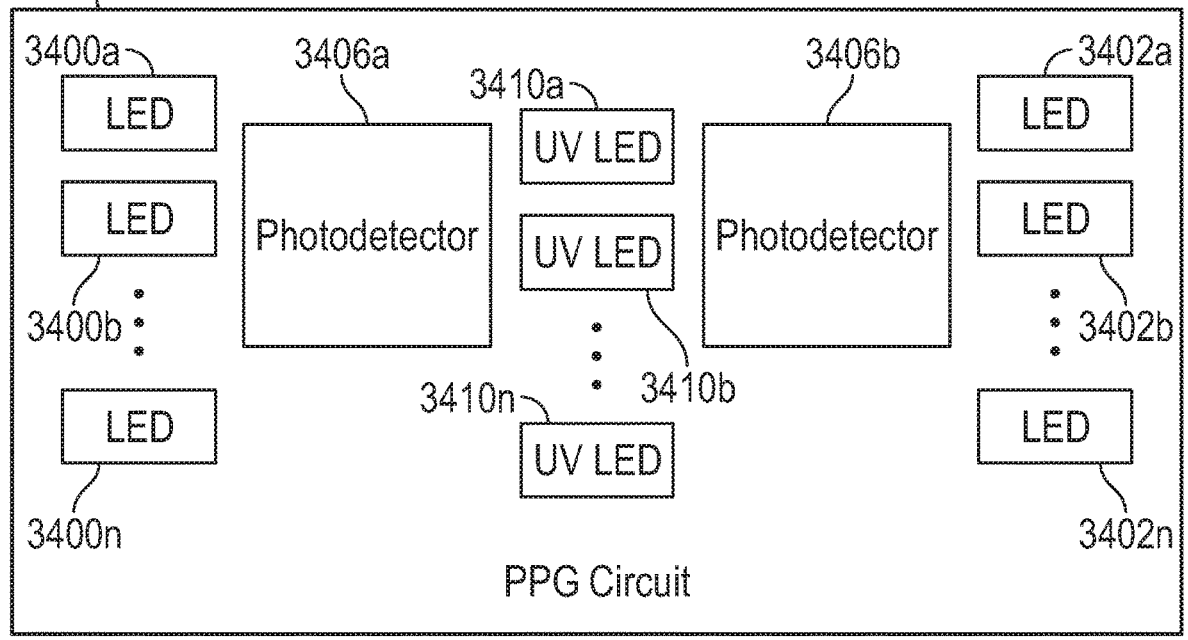
FIG. 34B illustrates a schematic block drawing of an exemplary embodiment of the PPG circuit in more detail.

FIG. 34B illustrates a schematic block drawing of an exemplary embodiment of the PPG circuit 110 in more detail. In this embodiment, the PPG circuit 110 includes a first photodetector 3406a and a second photodetector 3406b. A first set of light sources, LEDs 3400a-n are on a first side of the first photodetector 3406. A second set of light sources, LEDs 3402a-n are on a second side of the second photodetector 3406b. A third set of light sources, LEDs 3410a-n, are arranged between the first photodetector 3406a and the second photodetector 3406b. In an embodiment, the third set of light sources emits light in the UV range. For example, the UV LEDs 3410a-n emit light at a plurality of different wavelengths in the UV range. The first set of LEDs 3400 and the second set of LEDs 3402 may each include an LED in the IR range and visible light range.

Figure 35:
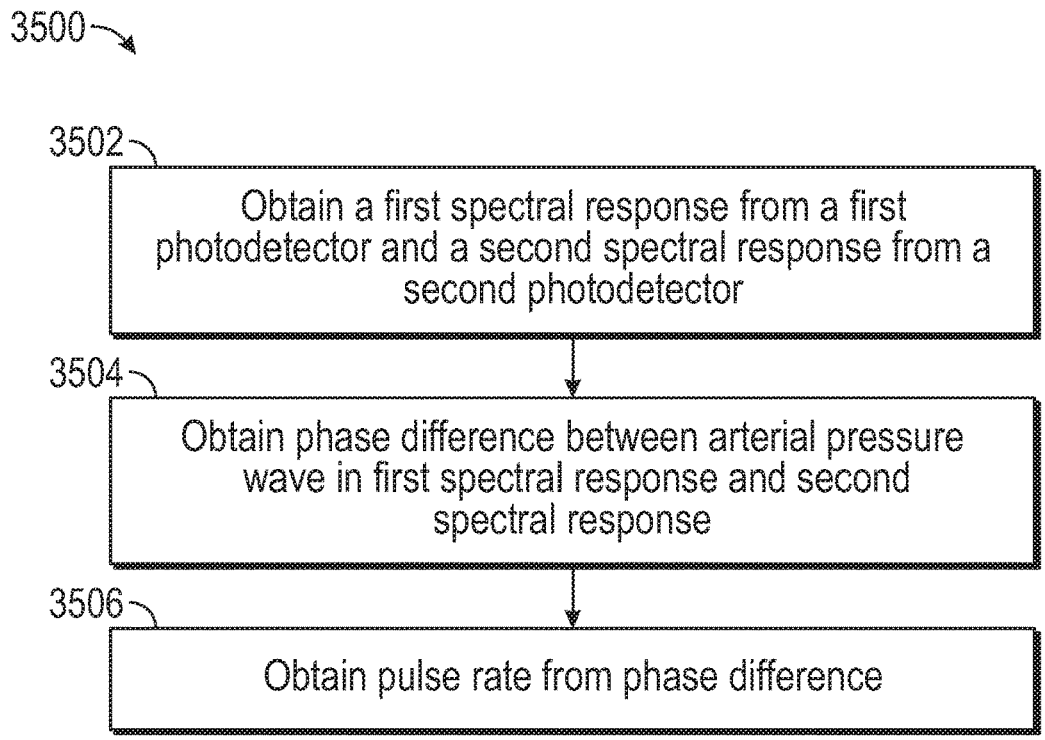
FIG. 35 illustrates a logical flow diagram of an exemplary embodiment of a method for determining heart rate.

FIG. 35 illustrates a logical flow diagram of an exemplary embodiment of a method 3500 for determining heart rate. A first spectral response is obtained from the first photodetector and a second spectral response is detected from the second photodetector using a high speed sample rate, such as 400 Hz. The two different photodetectors detect a small phase difference in subsequent spectral responses due to movement of the arterial pressure wave through the arteries. The phase difference may be correlated to a pulse rate. In general, the shorter the phase difference, the higher the pulse rate. A calibration table or curve may be generated to correlate the phase difference to the pulse rate and stored in the calibration database for the biosensor 100.

A first spectral response is obtained from the first photodetector and a second spectral response is obtained from the second photodetector at 3502. A phase difference is obtained between the arterial pressure wave in the first spectral response and the second spectral response at 3504. A pulse rate is then obtained using a calibration database at 3506.

Figure 36:
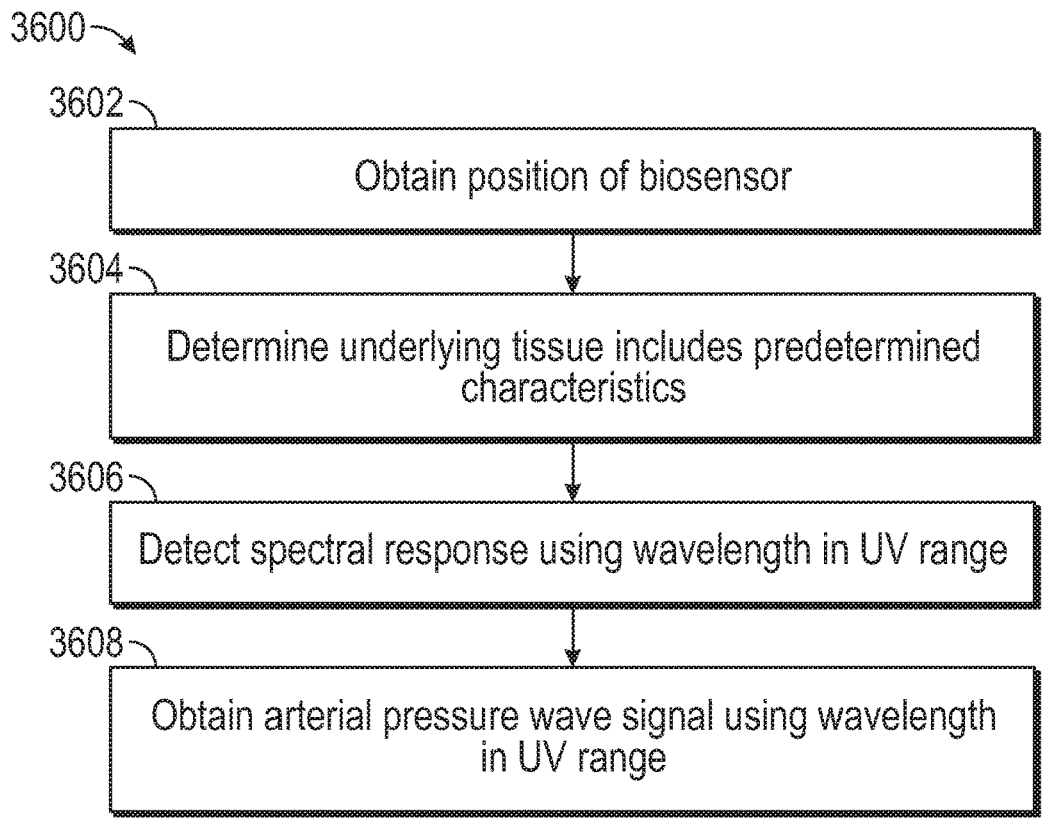
FIG. 36 illustrates a logical flow diagram of an exemplary embodiment of a method for determining cardiac cycle.

FIG. 36 illustrates a logical flow diagram of an exemplary embodiment of a method 3600 for determining a cardiac cycle. In an embodiment, a spectral response of a wavelength in the UV range of 400 nm or a wavelength of 500 nm or less may be used to determine a cardiac cycle signal. It has been determined in unexpected results that a cardiac cycle signal may be more easily detected using a wavelength of 500 nm or less over certain types of skin tissue, e.g., especially in abdominal area, upper arm, thigh, calf or other skin areas including fatty tissue or deposits wherein blood vessels may not be prevalent or near the skin surface. In an embodiment, the biosensor 100 obtains a position on the skin surface at 3602 or determines the underlying skin tissues includes a predetermined characteristic, e.g. fatty tissue or deposits wherein major arterial blood vessels may not be prevalent or near the skin surface at 3604. The biosensor 100 then transmits a wavelength in the UV range (e.g., 400 nm or less) or a wavelength of 500 nm or less directed at the skin tissue. The biosensor 100 detects the spectral response at 3606 and obtains a signal indicating a cardiac cycle from the spectral response at 3608. Heart rate and other information may be more easily obtained from the spectral response of a wavelength in the UV range or a wavelength of 500 nm or less due to the deeper penetration of these wavelengths in the skin tissue.

Figure 37:
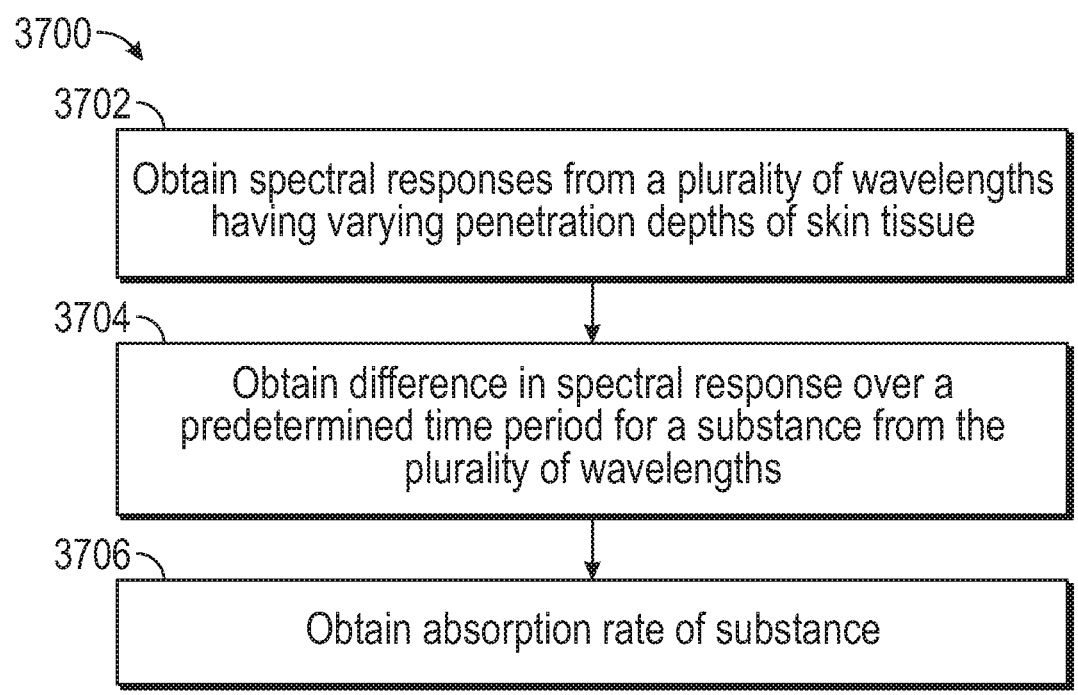
FIG. 37 illustrates a logical flow diagram of an exemplary embodiment of a method for determining an absorption rate of a substance

FIG. 37 illustrates a logical flow diagram of an exemplary embodiment of a method 3700 for determining an absorption rate of a substance. In an embodiment, the PPG circuit 110 includes one or more light sources configured to emit a plurality of different wavelengths of UV light. The UV light has different ability to penetrate skin tissue depending on its wavelength.

The higher the UV wavelength, the less the penetration depth in the skin tissue. Thus, by projecting a plurality of different UV wavelengths at the skin tissue, the biosensor 100 may determine absorption rate of a substance into the skin tissue.

The biosensor 100 obtains the spectral responses from a plurality of different wavelengths, wherein the different wavelengths have varying penetration depths of skin tissue at 3702. The absorption spectra of a substance at different depths in the skin tissue may be determined from the different spectral responses. The biosensor 100 determines the difference in absorption spectra of a substance from the plurality of different spectral responses at 3704. The biosensor 100 may continue to obtain and monitor the difference in absorption spectra of a substance at different depths in the skin tissue over a period of time. The biosensor 100 may then obtain an absorption rate of the substance into the skin tissue from the difference in absorption spectra of a substance at the plurality of different wavelengths at 3706.

Figure 38:
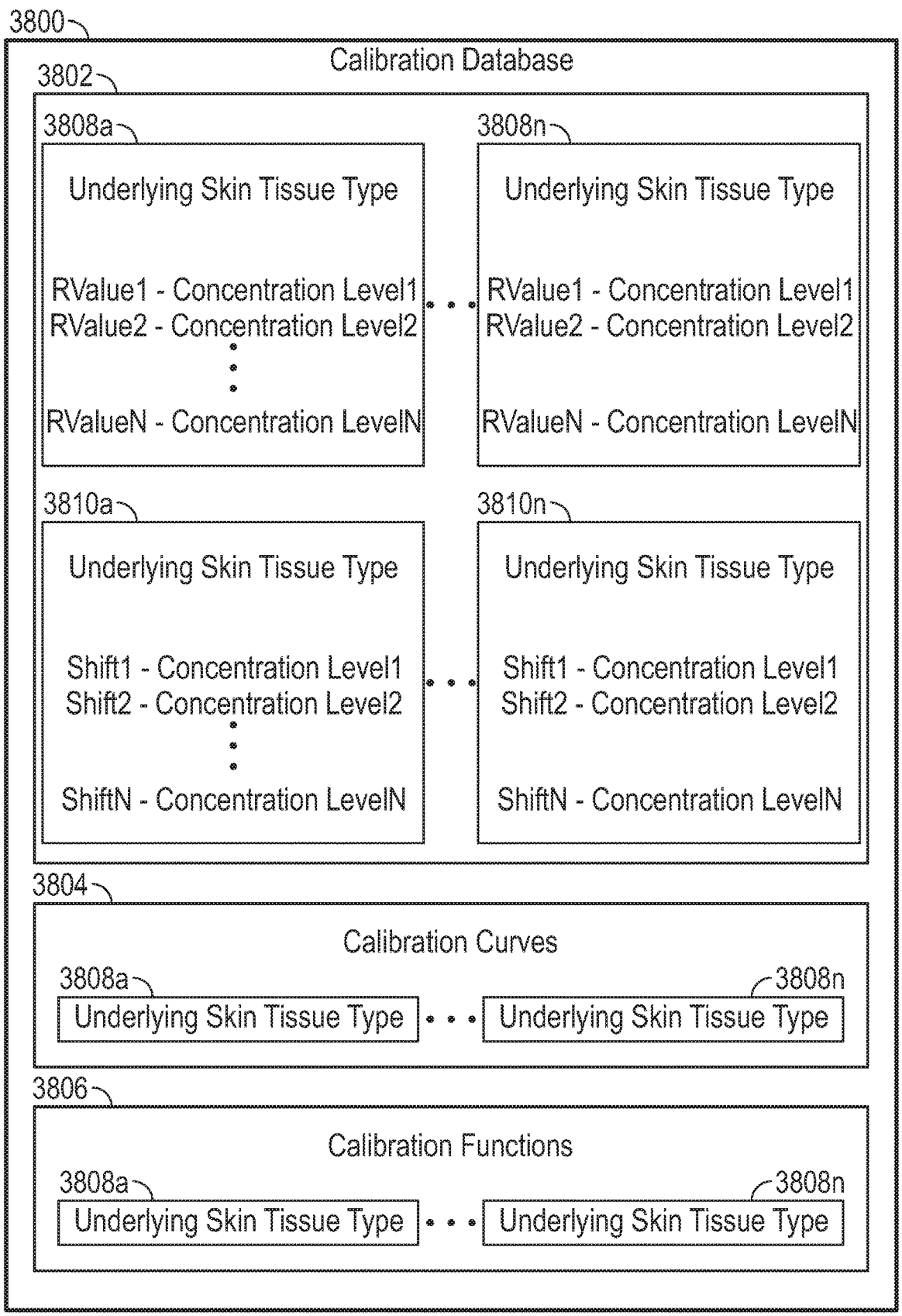
FIG. 38 illustrates a schematic block diagram of an embodiment of a calibration database.

FIG. 38 illustrates a schematic block diagram of an embodiment of a calibration database 3800. The calibration database 3800 includes one or more calibration tables 3802, calibration curves 3804 or calibration functions 3806 for correlating obtained values to concentration levels of NO. The concentration level of NO may be expressed in the calibration tables 3802 as units of mmol/liter, as a saturation level percentage (SpNO %), as a relative level on a scale (e.g., 0-10), etc.

The calibration tables 3802 include one or more calibration tables for one or more underlying skin tissue type 3808a-n. In one aspect, the calibration tables 3808 correlate an R value to a concentration level of NO for a plurality of underlying skin tissue types. For example, a first set of tables 3808a-n may correlate R values to NO concentration levels for a wrist area, a second table for an abdominal area, a third table for a forehead area, etc.

In another aspect, a set of calibration tables 3810a-n correlate an absorption spectra shift to a concentration level of NO for a plurality of underlying skin tissue types. For example, a first table 3810 may correlate a degree of absorption spectra shift of oxygenated hemoglobin to NO concentration levels for a wrist area, a second table 3810 for an abdominal area, a third table 3810 for a forehead area, etc. The degree of shift may be for the peak of the absorbance spectra curve of oxygenated hemoglobin from around 421 nm. In another example, the set of table 3810s may correlate a degree of absorption spectra shift of deoxygenated hemoglobin to NO concentration levels for a wrist area, a second table for an abdominal area, a third table for a forehead area, etc. The degree of shift may be for the peak of the absorbance spectra curve of deoxygenated hemoglobin from around 430 nm.

The calibration database 3802 may also include a set of calibration curves 3804 for a plurality of underlying skin tissue types. The calibration curves may correlate R values or degree of shifts to concentration levels of NO.

The calibration database 3802 may also include calibration functions 3806. The calibration functions 3806 may be derived (e.g., using regressive functions) from the correlation data from the calibration curves 3804 or the calibration tables 3802. The calibration functions 3806 may correlate R values or degree of shifts to concentration levels of NO for a plurality of underlying skin tissue types.

Based on these unexpected results, in one aspect, the biosensor 100 may determine non-invasively an indicator of the NO concentration level in vivo of a patient. The biosensor 100 detects a plurality of spectral responses from light directed at skin tissue of a patient. The spectral responses are used to determine an R value from $L_{\lambda 1}/L_{\lambda 2}$, wherein $\lambda 1$ has a high absorption coefficient for NO and is in a range from 370 nm to 410 nm and preferably in a range from 390-395 nm. The second wavelength $\lambda 2$ has a lower absorption coefficient for NO than the first wavelength $\lambda 1$ and may be in a range equal to or greater than 660 nm.

In the clinical trials herein, the R value was in a range of 0-8. Other ranges, weights or functions derived using the R value described herein may be implemented that changes the numerical value of the R values described herein or the range of the R values described herein. A calibration database may then correlate the R value to a concentration level of NO.

The R value may be non-invasively and quickly and easily obtained using the biosensor 100 in a physician's office or other clinical setting or at home. In one aspect, the R value may be used to determine whether further testing for health conditions need to be performed. For example, upon detection of a low R value of less than 1, a clinician may then determine to perform further testing and monitoring, e.g. for diabetes.

A wide range of conditions require frequent monitoring such as diabetes, hypotension, hypertension, cardiac arrest, carbon monoxide poisoning, seizures, strokes, respiratory arrest, dyspnea, and sepsis. The biosensor 100 may be used to continuously monitor patients with one or more of these conditions. The biosensor 100 may monitor NO levels, as well as other patient vitals such as heart rate, blood pressure, and/or SpO2.

Embodiment-Measurements of Other Substances

Using similar principles described herein, the biosensor 100 may measure concentration levels or indicators of other substances in pulsating blood flow. For example, absorption coefficients for one or more frequencies that have an intensity level responsive to concentration level of substance may be determined. The biosensor 100 may then detect the substance at the determined one or more frequencies as described herein and determine the concentration levels using the Beer-Lambert principles and the absorption coefficients. The L values and R values may be calculated based on the obtained spectral response. In one aspect, the biosensor 100 may detect various electrolyte concentration levels or blood analyte levels, such as bilirubin and sodium and potassium. In another aspect, the biosensor 100 may detect sodium NACL concentration levels in the arterial blood flow to determine dehydration. In yet another aspect, the biosensor 100 may be configured to detect proteins or abnormal cells or other elements or compounds associated with cancer. In another aspect, the PPG sensor may detect white blood cell counts. In another aspect, the biosensor may detect blood alcohol levels.

For example, the biosensor 100 may also determine alcohol levels in the blood using wavelengths at approximately 390 nm and/or 468 nm. In another embodiment, an R468,940 value for at least L468 nm/L940 nm may be used as a liver enzyme indicator, e.g. P450 enzyme indicator. In another embodiment, an R592,940 value for at least L592 nm/L940 nm may be used as a digestive indicator to measure digestive responses, such as phase 1 and phase 2 digestive stages. In another aspect, the biosensor 100 may detect white blood cell counts or concentration levels in arterial blood flow using similar PPG techniques. The presence of white blood cell counts may indicate the presence of infection.

In another aspect, abnormal cells or proteins or compounds that are present or have higher concentrations in the blood with persons having cancer, may be detected using similar PPG techniques described herein at one or more other wavelengths. Thus, cancer risk may then be obtained through non-invasive testing by the biosensor 100. Since the biosensor 100 may operate in multiple frequencies, various health monitoring tests may be performed concurrently.

One or more embodiments have been described herein for the non-invasive and continuous biosensor 100. Due to its compact form factor, the biosensor 100 may be configured for measurements on various skin surfaces of a patient, including on a forehead, arm, wrist, abdominal area, chest, leg, ear lobe, finger, toe, ear canal, etc. The biosensor includes one or more sensors for detecting biosensor data, such as a patient's vitals, activity levels, or concentrations of substances in the blood flow of the patient. In particular, the PPG sensor is configured to monitor concentration levels or indicators of one or more substances in the blood flow of the patient. In one aspect, the PPG sensor may non-invasively and continuously detect nitric oxide (NO) levels in pulsatile arterial blood flow.

In one or more aspects herein, a processing module or circuit includes at least one processing device, such as a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. A memory is a non-transitory memory device and may be an internal memory or an external memory, and the memory may be a single memory device or a plurality of memory devices. The memory may be a read-only memory, random access memory, volatile memory, non-volatile memory, static memory, dynamic memory, flash memory, cache memory, and/or any non-transitory memory device that stores digital information.

As may be used herein, the term "operable to" or "configurable to" indicates that an element includes one or more of circuits, instructions, modules, data, input(s), output(s), etc., to perform one or more of the described or necessary corresponding functions and may further include inferred coupling to one or more other items to perform the described or necessary corresponding functions. As may also be used herein, the term(s) "coupled", "coupled to", "connected to" and/or "connecting" or "interconnecting" includes direct connection or link between nodes/devices and/or indirect connection between nodes/devices via an intervening item (e.g., an item includes, but is not limited to, a component, an element, a circuit, a module, a node, device, network element, etc.). As may further be used herein, inferred connections (i.e., where one element is connected to another element by inference) includes direct and indirect connection between two items in the same manner as "connected to".

As may be used herein, the terms "substantially" and "approximately" provides an industry-accepted tolerance for its corresponding term and/or relativity between items. Such an industry-accepted tolerance ranges from less than one percent to fifty percent and corresponds to, but is not limited to, frequencies, wavelengths, component values, integrated circuit process variations, temperature variations, rise and fall times, and/or thermal noise. Such relativity between items ranges from a difference of a few percent to magnitude differences.

Note that the aspects of the present disclosure may be described herein as a process that is depicted as a schematic, a flowchart, a flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed. A process may correspond to a method, a function, a procedure, a subroutine, a subprogram, etc. When a process corresponds to a function, its termination corresponds to a return of the function to the calling function or the main function.

The various features of the disclosure described herein can be implemented in different systems and devices without departing from the disclosure. It should be noted that the foregoing aspects of the disclosure are merely examples and are not to be construed as limiting the disclosure. The description of the aspects of the present disclosure is intended to be illustrative, and not to limit the scope of the claims. As such, the present teachings can be readily applied to other types of apparatuses and many alternatives, modifications, and variations will be apparent to those skilled in the art.

In the foregoing specification, certain representative aspects of the invention have been described with reference to specific examples. Various modifications and changes may be made, however, without departing from the scope of the present invention as set forth in the claims. The specification and figures are illustrative, rather than restrictive, and modifications are intended to be included within the scope of the present invention. Accordingly, the scope of the invention should be determined by the claims and their legal equivalents rather than by merely the examples described. For example, the components and/or elements recited in any apparatus claims may be assembled or otherwise operationally configured in a variety of permutations and are accordingly not limited to the specific configuration recited in the claims.

Furthermore, certain benefits, other advantages and solutions to problems have been described above with regard to particular embodiments; however, any benefit, advantage, solution to a problem, or any element that may cause any particular benefit, advantage, or solution to occur or to become more pronounced are not to be construed as critical, required, or essential features or components of any or all the claims.

As used herein, the terms "comprise," "comprises," "comprising," "having," "including," "includes" or any variation thereof, are intended to reference a nonexclusive inclusion, such that a process, method, article, composition or apparatus that comprises a list of elements does not include only those elements recited, but may also include other elements not expressly listed or inherent to such process, method, article, composition, or apparatus. Other combinations and/or modifications of the above-described structures, arrangements, applications, proportions, elements, materials, or components used in the practice of the present invention, in addition to those not specifically recited, may be varied or otherwise particularly adapted to specific environments, manufacturing specifications, design parameters, or other operating requirements without departing from the general principles of the same.

Moreover, reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is intended to be construed under the provisions of 35 U.S.C. § 112(f) as a "means-plus-function" type element, unless the element is expressly recited using the phrase "means for" or, in the case of a method claim, the element is recited using the phrase "step for."

The invention claimed is:

1. A device, comprising:
    an optical circuit including a light source and a photodetector, the optical circuit configured to:
        emit light using the light source at each of a first wavelength having a high absorption coefficient for nitric oxide (NO) in blood flow and a second wavelength having a low absorption coefficient for NO in blood flow;
        measure reflections of the light emitted by the light source from skin tissue of a patient to obtain each of a first photoplethysmography (PPG) signal corresponding to reflected light at the first wavelength and a second PPG signal corresponding to reflected light at the second wavelength; and
    at least one processing circuit configured to:
        determine a measurement using the first PPG signal and the second PPG signal, the measurement corresponding to an indication for hyperglycemia or hypoglycemia;
        compare the measurement to a predetermined normal range for the measurement; and
        determine whether the measurement is outside of the predetermined normal range.

2. The device of claim 1, wherein the measurement includes an AC component of the first PPG signal.

3. The device of claim 1, wherein the measurement includes a ratio of an AC component of the first PPG signal and an AC component of the second PPG signal.

4. The device of claim 1, wherein the measurement includes a level of NO in the blood flow of the patient.

5. The device of claim 1, wherein the measurement includes a level of glucose in the blood flow of the patient.

6. The device of claim 1, wherein the optical circuit is configured on a patch, wrist band, finger attachment or ear piece.

7. The device of claim 1, wherein the optical circuit and the at least one processing circuit is configured on a patch, wrist band or ear piece.

8. The device of claim 1, wherein the at least one processing circuit is further configured to generate an alert in response to the measurement being outside of the predetermined normal range.

9. A device, comprising:
    an optical circuit including a light source and a photodetector, the optical circuit configured to:
        emit light using the light source at each of a first wavelength having a high absorption coefficient for nitric oxide (NO) in blood flow and a second wavelength having a low absorption coefficient for NO in blood flow;
        measure reflections of the light emitted by the light source from skin tissue of a patient to obtain each of a first photoplethysmography (PPG) signal corresponding to reflected light at the first wavelength and a second PPG signal corresponding to reflected light at the second wavelength; and
    at least one processing circuit configured to:
        determine a measurement of a level of NO in blood flow using the first PPG signal and the second PPG signal;
        compare the measurement of the level of NO to a predetermined normal range for NO for a health condition; and
        determine the measurement of the level of NO is outside of the predetermined normal range.

10. The device of claim 9, wherein the processing circuit is configured to generate an alert when the measurement of the level of NO is outside of the predetermined normal range.

11. The device of claim 9, wherein the processing circuit is configured to generate a display of the measurement of the level of NO.

12. The device of claim 9, wherein the measurement of the level of NO includes an AC component of the first PPG signal.

13. The device of claim 9, wherein the measurement of the level of NO includes a ratio of an AC component of the first PPG signal and an AC component of the second PPG signal.

14. The device of claim 9, wherein the health condition includes one or more of:
    hyperglycemia, hypoglycemia, diabetic condition, insulin response, hypovolemia, vascular health, dementia, Alzheimer's disease, post-traumatic stress syndrome (PTSD), infection or sepsis.

15. The device of claim 9, wherein the health condition includes a presence of one or more compounds that lead to unsafe levels of NO in blood vessels, wherein the one or more compounds include one or more of: lidocaine, nitrates such as nitroglycerin, nitric oxide, nitrogen based fertilizers, dapsone, benzocaine, cyanide, or anesthesia.

16. The device of claim 9, further comprising a transceiver configured to transmit data to a remote user device.

17. The device of claim 9, wherein the first wavelength having a high absorption coefficient for NO in blood flow is in a range of approximately 380 nm to 400 nm.

18. A device, comprising:
    at least one processing circuit configured to:
        obtain a plurality of PPG signals from at least one photodetector circuit, the plurality of PPG signals including:

a first PPG signal corresponding to a first wavelength of light reflected from skin tissue of a patient, wherein the first wavelength has a high absorption coefficient for nitric oxide (NO) in blood flow; and a second PPG signal corresponding to a second wavelength of light reflected from skin tissue of the patient, wherein the second wavelength has a low absorption coefficient for NO in blood flow;

determine a measurement of a level of NO in blood flow using the first PPG signal and the second PPG signal;

compare the measurement of the level of NO to a predetermined normal range for NO for a health condition; and determine the measurement of the level of NO is outside of the predetermined normal range.

* * * * *